United States Patent
Lim et al.

(10) Patent No.: US 10,454,044 B2
(45) Date of Patent: Oct. 22, 2019

(54) PLURALITY OF HOST MATERIALS AND ORGANIC ELECTROLUMINESCENT DEVICE COMPRISING THE SAME

(71) Applicant: Rohm and Haas Electronic Materials Korea Ltd., Cheonan (KR)

(72) Inventors: Young-Mook Lim, Yongin (KR); Bitnari Kim, Suwon (KR)

(73) Assignee: Rohm and Haas Electronic Materials Korea Ltd., Cheonan (KR)

( * ) Notice: Subject to any disclaimer, the term of this patent is extended or adjusted under 35 U.S.C. 154(b) by 0 days.

(21) Appl. No.: 15/774,288

(22) PCT Filed: Nov. 1, 2016

(86) PCT No.: PCT/KR2016/012455
§ 371 (c)(1),
(2) Date: May 8, 2018

(87) PCT Pub. No.: WO2017/086629
PCT Pub. Date: May 26, 2017

(65) Prior Publication Data
US 2019/0074448 A1    Mar. 7, 2019

(30) Foreign Application Priority Data

Nov. 17, 2015 (KR) .................. 10-2015-0161209
Sep. 20, 2016 (KR) .................. 10-2016-0120026

(51) Int. Cl.
| | | |
|---|---|---|
| *H01L 51/00* | (2006.01) | |
| *C07D 209/86* | (2006.01) | |
| *C07D 403/10* | (2006.01) | |
| *C07D 495/04* | (2006.01) | |
| *C07D 491/048* | (2006.01) | |
| *C07D 209/08* | (2006.01) | |
| *H01L 51/50* | (2006.01) | |

(52) U.S. Cl.
CPC ........ *H01L 51/0072* (2013.01); *C07D 209/08* (2013.01); *C07D 209/86* (2013.01); *C07D 403/10* (2013.01); *C07D 491/048* (2013.01); *C07D 495/04* (2013.01); *H01L 51/0059* (2013.01); *H01L 51/0067* (2013.01); *H01L 51/5016* (2013.01); *H01L 2251/5384* (2013.01)

(58) Field of Classification Search
CPC ............. H01L 51/0072; H01L 51/5016; H01L 51/0067; H01L 51/0059; C07D 209/86; C07D 403/10; C07D 495/04; C07D 491/048
See application file for complete search history.

(56) References Cited

U.S. PATENT DOCUMENTS

| | | | |
|---|---|---|---|
| 2011/0278555 A1* | 11/2011 | Inoue | C07D 209/82 257/40 |
| 2011/0279020 A1* | 11/2011 | Inoue | C07D 209/82 313/504 |
| 2014/0197386 A1 | 7/2014 | Kim et al. | |
| 2014/0209880 A1* | 7/2014 | Choi | H01L 51/0067 257/40 |
| 2015/0171341 A1* | 6/2015 | Lee | H01L 51/0072 257/40 |
| 2015/0200373 A1 | 7/2015 | Cho et al. | |

FOREIGN PATENT DOCUMENTS

EP    2415769 A1    2/2012

* cited by examiner

*Primary Examiner* — Caridad Everhart
(74) *Attorney, Agent, or Firm* — S. Matthew Cairns

(57) ABSTRACT

The present disclosure relates to a host material and an organic electroluminescent device comprising the same. By using a specific combination of two or more host compounds according to the present disclosure, the organic electroluminescent device of the present disclosure has luminous efficiency at least equivalent to or higher than conventional devices and has lifespan better than conventional devices.

8 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak, by using small aromatic diamine molecules and aluminum complexes as materials to form a light-emitting layer [Appl. Phys. Lett. 51, 913, 1987].

The organic EL device (OLED) converts electric energy into light when electricity is applied to an organic light-emitting material(s). Generally, the organic EL device has a structure comprising an anode, a cathode, and an organic layer disposed between the anode and the cathode. The organic layer of the organic EL device comprises a hole injection layer, a hole transport layer, an electron blocking layer, a light-emitting layer (comprising a host material and a dopant material), an electron buffering layer, a hole blocking layer, an electron transport layer, an electron injection layer, etc. Depending on its function, materials for forming the organic layer can be classified as a hole injection material, a hole transport material, an electron blocking material, a light-emitting material, an electron buffering material, a hole blocking material, an electron transport material, an electron injection material, etc. When a voltage is applied to the organic EL device, holes and electrons are injected from an anode and a cathode, respectively, to the light-emitting layer. Excitons having high energy are formed by recombinations between the holes and the electrons, the energy puts the organic light-emitting compound in an excited state, and the decay of the excited state results in a relaxation of the energy level into a ground state, accompanied by light-emission.

The most important factor determining luminous efficiency in the organic EL device is light-emitting materials. The light-emitting material needs to have high quantum efficiency, high electron mobility, and high hole mobility. Furthermore, the light-emitting layer formed by the light-emitting material needs to be uniform and stable. Depending on the colors visualized by light-emission, the light-emitting materials can be classified as a blue-, green-, or red-emitting material, and can additionally include a yellow- or orange-emitting material. Furthermore, the light-emitting material can be classified according to its function, as a host material and a dopant material. Recently, the development of an OLED providing high efficiency and a long lifespan is urgent. In particular, considering EL requirements for a middle or large-sized OLED panel, materials showing better performance than conventional ones must be urgently developed. In order to achieve the development, a host material which plays a role as a solvent in a solid state and transfers energy, should have high purity, and an appropriate molecular weight for being deposited under a vacuum. In addition, a host material should have high glass transition temperature and high thermal decomposition temperature to ensure thermal stability; high electrochemical stability to have a long lifespan; ease of preparation for amorphous thin film; and good adhesion to materials of adjacent layers. Furthermore, a host material should not move to an adjacent layer.

The light-emitting material can be prepared by combining a host with a dopant to improve color purity, luminous efficiency, and stability. Generally, a device showing good EL performances comprises a light-emitting layer prepared by combining a host with a dopant. The host material greatly influences the efficiency and lifespan of the EL device when using a host/dopant system, and thus its selection is important.

Korean Patent Application Laying-Open No. 10-2014-0096203 discloses an organic electroluminescent device using indole derivatives and biscarbazole compounds as a plurality of host materials. However, it does not specifically disclose an organic electroluminescent device comprising a compound having a structure wherein benzocarbazole and triazinyl are connected via a pyridine linker, as a host material.

DISCLOSURE OF THE INVENTION

Problems to be Solved

The objective of the present disclosure is to provide an organic electroluminescent device that has luminous efficiency at least equivalent to or higher than conventional devices and has lifespan longer than conventional devices.

Solution to Problems

As a result of an earnest study for solving the above-described problems, the present inventors found that the above objective can be achieved by a host material that comprises one or more first host compounds and one or more second host compounds wherein the first host compound is represented by the following formula 1 and the second host compound is represented by the following formula 2.

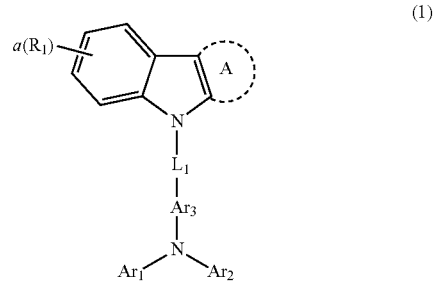

wherein $L_1$ represents a single bond or a substituted or unsubstituted (C6-C30)arylene, A represents hydrogen, a substituted or unsubstituted phenyl, a substituted or unsubstituted naphthyl, a substituted or unsubstituted fluorenyl, a substituted or unsubstituted dibenzothiophenyl, or a substituted or unsubstituted dibenzofuranyl, $Ar_1$, $Ar_2$ and $Ar_3$, each independently, represent a substituted or unsubstituted (C6-C30)aryl(ene), or a substituted or unsubstituted 3- to 30-membered heteroaryl(ene); or $Ar_2$ and $Ar_3$ may be linked to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur, $R_1$ represents deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or $R_1$ may be linked to an adjacent substituent(s) to form a substituted or unsubstituted 3 to 30-membered, mono- or polycyclic, alicyclic or aromatic ring, or a combination of the alicyclic ring and the aromatic ring, wherein the heteroaryl(ene) contains one or more heteroatoms selected from the group consisting of B, N, O, S, Si, and P, a represents an integer of 0 to 4, and when a is an integer of 2 or more, each of $R_1$ may be the same or different;

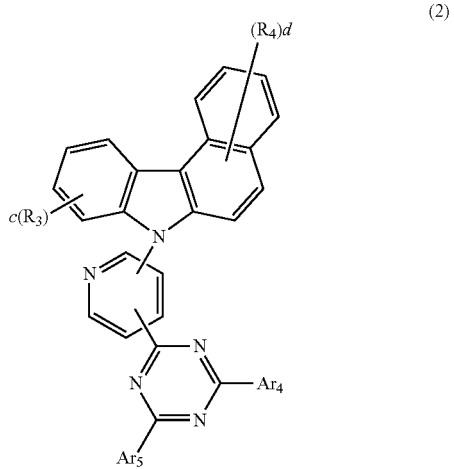

(2)

wherein $Ar_4$ and $Ar_5$, each independently, represent a substituted or unsubstituted (C6-C30)aryl, a substituted or unsubstituted (C3-C30)cycloalkyl, or a substituted or unsubstituted 3- to 30-membered heteroaryl, $R_3$ and $R_4$, each independently, represent deuterium, a halogen, a cyano, a substituted or unsubstituted (C1-C30) alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri (C1-C30)alkylsilyl, a substituted or unsubstituted tri(C6-C30)arylsilyl, a substituted or unsubstituted di(C1-C30) alkyl(C6-C30)arylsilyl, or a substituted or unsubstituted mono- or di-(C6-C30)arylamino, wherein the heteroaryl contains one or more heteroatoms selected from the group consisting of B, N, O, S, Si, and P, and c represents an integer of 0 to 4; d represents an integer of 0 to 6; and when c or d is an integer of 2 or more, each of $R_3$ or $R_4$ may be the same or different.

Effects of the Invention

The present disclosure provides an organic electroluminescent device that has luminous efficiency at least equivalent to or higher than conventional devices and has lifespan longer than conventional devices. Furthermore, a display system or a lighting system using the organic electroluminescent device of the present disclosure can be produced.

EMBODIMENTS OF THE INVENTION

Hereinafter, the present disclosure will be described in detail. However, the following description is intended to explain the invention, and is not meant in any way to restrict the scope of the invention.

The host materials that comprise organic electroluminescent compounds represented by formula 1 above and represented by formula 2 above will be described in detail.

In formula 1, $L_1$ may represent a single bond or a substituted or unsubstituted (C6-C30)arylene, preferably a single bond or a substituted or unsubstituted (C6-C25) arylene, more preferably a single bond or a substituted or unsubstituted (C6-C18)arylene, and may include a single bond, an unsubstituted phenylene, an unsubstituted naphthylene, and an unsubstituted biphenylene.

In formula 1, A may represent hydrogen, a substituted or unsubstituted phenyl, a substituted or unsubstituted naphthyl, a substituted or unsubstituted fluorenyl, a substituted or unsubstituted dibenzothiophenyl, or a substituted or unsubstituted dibenzofuranyl, preferably hydrogen, an unsubstituted phenyl, a fluorenyl substituted with one or more methyl, an unsubstituted naphthyl, an unsubstituted dibenzothiophenyl, or an unsubstituted dibenzofuranyl; and the substituted fluorenyl may be a fluorenyl substituted with dimethyl.

In formula 1, $Ar_1$ to $Ar_3$, each independently, may represent a substituted or unsubstituted (C6-C30)aryl(ene), or a substituted or unsubstituted 3 to 30-membered heteroaryl(ene); $Ar_2$ and $Ar_3$ may be linked to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur; preferably, $Ar_1$ to $Ar_3$, each independently, may represent a substituted or unsubstituted (C6-C25)aryl(ene); $Ar_2$ and $Ar_3$ may be linked to form a substituted or unsubstituted 5 to 25-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur; more preferably, $Ar_1$ to $Ar_3$, each independently, may represent a substituted or unsubstituted (C6-C20)aryl(ene); $Ar_2$ and $Ar_3$ may be linked to form a substituted or unsubstituted 5 to 20-membered, mono- or polycyclic, alicyclic or aromatic ring, or a combination of the alicyclic ring and the aromatic ring, whose carbon atom(s) may be replaced with nitrogen. For example, $Ar_1$ and $Ar_2$ may be a phenyl substituted or unsubstituted with naphthyl or phenanthrenyl, an unsubstituted biphenyl, an unsubstituted terphenyl, a fluorenyl substituted with dimethyl, or a benzofluorenyl substituted with dimethyl; $Ar_3$ may represent an unsubstituted phenylene, an unsubstituted naphthylene, or a fluorenylene substituted with dimethyl; and $Ar_2$ and $Ar_3$ may be linked to form an unsubstituted carbazole.

In formula 1, $R_1$ may represent deuterium, a halogen, a cyano, a substituted or unsubstituted (C1-C30)alkyl, a substituted or unsubstituted (C2-C30)alkenyl, a substituted or unsubstituted (C2-C30) alkynyl, a substituted or unsubstituted (C3-C30)cycloalkyl, a substituted or unsubstituted (C6-C30)aryl, a substituted or unsubstituted 3 to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or $R_1$ may be linked to an adjacent substituent(s) to form a substituted or unsubstituted 3 to 30-membered, mono- or polycyclic, alicyclic or aromatic ring, or a combination of the alicyclic ring and the aromatic ring; preferably, $R_1$ may be linked to an adjacent substituent(s) to form a substituted or unsubstituted 5 to 25-membered, mono- or polycyclic aromatic ring; more preferably, $R_1$ may be linked to an adjacent substituent(s) to form a substituted or unsubstituted 5 to 18-membered, mono- or polycyclic, aromatic ring; specifically, the aromatic ring formed by linking the adjacent substituents may be selected from the group consisting of a benzene, an indole, an indene, a benzofuran and a bezothiophene, substituted or unsubstituted with a (C1-C10)alkyl or a (C6-C15)aryl; for example, the adjacent substituents may be linked to form an unsubstituted benzene, an indene substituted with dimethyl, an unsubstituted benzofuran or an unsubstituted benzothiophene.

In formula 1, a represents an integer of 0 to 4, preferably an integer of 0 to 2; and when a is an integer of 2 or more, each of $R_1$ may be the same or different.

In formula 2, $Ar_4$ and $Ar_5$, each independently, may represent a substituted or unsubstituted (C6-C30)aryl, a substituted or unsubstituted (C3-C30)cycloalkyl, or a substituted or unsubstituted 3- to 30-membered heteroaryl; preferably, each independently, may represent a substituted or unsubstituted (C6-C25)aryl; more preferably, each independently, may represent an unsubstituted (C6-C18)aryl, such as, an unsubstituted phenyl, an unsubstituted naphthyl, or an unsubstituted biphenyl.

In formula 2, $R_3$ and $R_4$, each independently, may represent deuterium, a halogen, a cyano, a substituted or unsubstituted (C1-C30)alkyl, a substituted or unsubstituted (C2-C30)alkenyl, a substituted or unsubstituted (C2-C30) alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; preferably, each independently, may represent a substituted or unsubstituted (C6-C25)aryl; or more preferably, each independently, may represent an unsubstituted (C6-C20)aryl, such as an unsubstituted phenyl, or an unsubstituted terphenyl.

In formula 2, c may represent an integer of 0 to 4; d may represent an integer of 0 to 6; preferably, c and d, each independently, may represent 0 or 2; more preferably, c and d, each independently, may represent 0 or 1. When each of c or d represents an integer of 2 or more, each of $R_3$ or $R_4$ may be the same or different.

In formulae 1 and 2, the heteroaryl contains one or more heteroatoms selected from the group consisting of B, N, O, S, Si, and P; preferably, one or more heteroatoms selected from the group consisting of N, O, and S.

The compound of formula 1 of the present disclosure may be represented by any one of the following formulae 3 to 7:

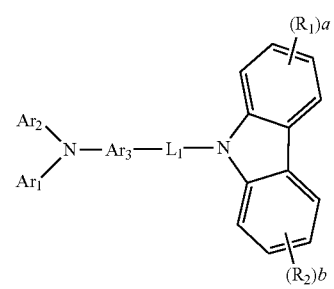

(3)

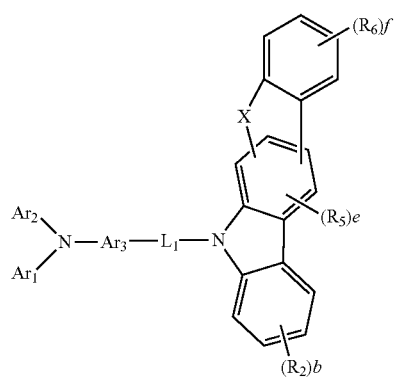

(4)

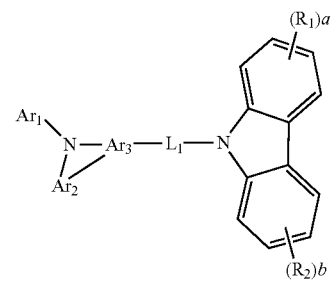

(5)

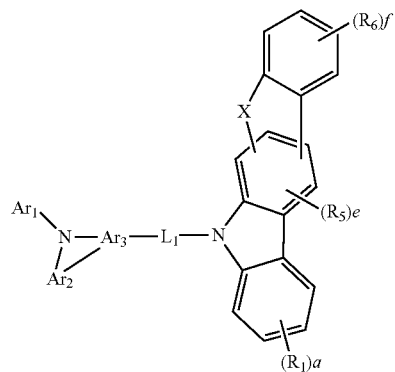

(6)

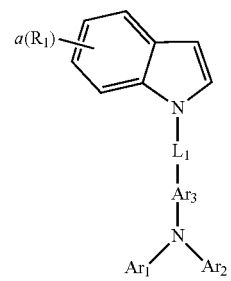

(7)

In formulae 3 to 7, $Ar_1$ to $Ar_3$, each independently, may represent a substituted or unsubstituted (C6-C30)aryl(ene), or a substituted or unsubstituted 3 to 30-membered heteroaryl(ene); preferably, a substituted or unsubstituted (C6-C25)aryl(ene); more preferably a substituted or unsubstituted (C6-C20)aryl(ene); for example, $Ar_1$ and $Ar_2$, each independently, may represent a phenyl substituted or unsubstituted with naphthyl or phenanthrenyl, an unsubstituted biphenyl, an unsubstituted terphenyl, a fluorenyl substituted with dimethyl, or a benzofluorenyl substituted with dimethyl; and $Ar_3$ may represent an unsubstituted phenylene, an unsubstituted naphthylene, or a fluorenylene substituted with dimethyl.

In formulae 4 and 6, X may represent S, O or $CR_7R_8$, preferably S or O.

In formulae 3 to 6, $R_2$ and $R_5$ to $R_8$, each independently, may represent deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or $R_2$ and $R_5$ to $R_8$, each independently, may be linked to an adjacent substituent(s) to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur; or preferably, $R_2$ and $R_5$ to $R_8$, each independently, may represent a substituted or unsubstituted (C1-C20)alkyl; or $R_2$ and $R_5$ to $R_8$, each independently, may be linked to an adjacent substituent(s) to form a substituted or unsubstituted 5 to 25-membered, mono- or polycyclic, aromatic ring, whose carbon atom(s) may be replaced with at least one heteroatom selected from the group consisting of nitrogen, oxygen, and sulfur; or more preferably, $R_2$ and $R_5$ to $R_8$, each independently, may be linked to an adjacent substituent(s) to form a substituted or unsubstituted 5 to 18-membered, mono- or polycyclic, aromatic ring; for example, the adjacent substituents may be linked to form an unsubstituted benzene ring, or an indene ring substituted with dimethyl.

In formulae 3 to 7, the heteroaryl contains one or more heteroatoms selected from the group consisting of B, N, O, S, Si, and P; preferably, one or more heteroatoms selected from the group consisting of N, O, and S.

In formulae 3 to 7, b and f, each independently, may represent an integer of 0 to 4, and e may represent an integer of 0 to 2; when each of b or f represents an integer of 2 or more, or when e represents an integer of 2, each of $R_2$, $R_5$, or $R_6$ may be the same or different. Preferably, b and f, each independently, may represent an integer of 0 to 2, and e may represent an integer of 0.

In formulae 3 to 7, $L_1$, $R_1$, and a are as defined in formula 1 above.

The compound of formula 3 of the present disclosure may be represented by any one of the following formulae 8 to 10, and the compound of formula 4 of the present disclosure may be represented by the following formula 11:

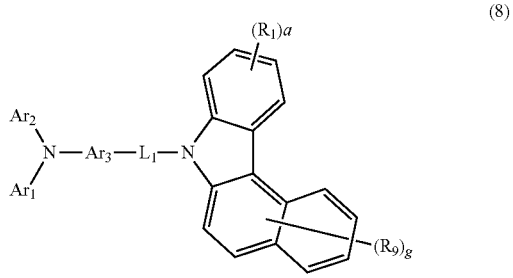

(8)

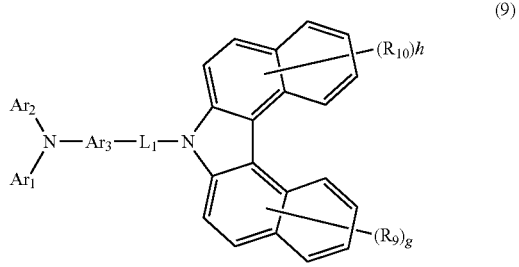

(9)

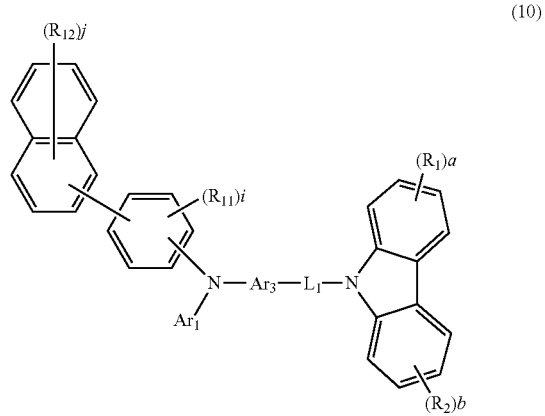

(10)

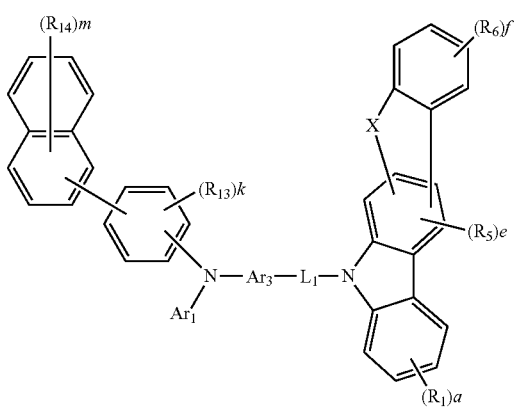

(11)

In formulae 8 to 11, $R_9$ to $R_{14}$, each independently, may represent deuterium, a halogen, a cyano, a substituted or unsubstituted (C1-C30)alkyl, a substituted or unsubstituted (C2-C30)alkenyl, a substituted or unsubstituted (C2-C30) alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; $R_9$ to $R_{14}$, each independently, may be linked to an adjacent substituent(s) to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur; preferably, $R_9$ to $R_{14}$, each independently, may be linked to an adjacent substituent(s) to form a substituted or unsubstituted 5 to 25-membered, mono- or polycyclic, aromatic ring, whose carbon atom(s) may be replaced with at least one heteroatom selected from the group consisting of nitrogen, oxygen, and sulfur; or more preferably, $R_9$ to $R_{14}$, each independently, may be linked to an adjacent substituent(s) to form an unsubstituted 5 to 18-membered, mono- or polycyclic, aromatic ring; for example, $R_9$ to $R_{14}$, each independently, may be linked to an adjacent substituent(s) to form an unsubstituted benzene ring.

In formulae 8 to 11, the heteroaryl contains one or more heteroatoms selected from the group consisting of B, N, O, S, Si, and P; preferably, one or more heteroatoms selected from the group consisting of N, O, and S.

In formulae 8 to 11, g and h, each independently, may represent an integer of 0 to 6; i and k, each independently, may represent an integer of 0 to 4; j and m, each independently, may represent an integer of 0 to 7; when each of g, h, i, j, k or m represents an integer of 2 or more, each of $R_9$, $R_{10}$, $R_{11}$, $R_{12}$, $R_{13}$, or $R_{14}$ may be the same or different. Preferably, g, h, i, and k, each independently, may represent 0, and, j and m, each independently, may represent 0 or 2.

In formulae 8 to 11, $L_1$, $R_1$, $R_2$, $R_5$, $R_6$, $Ar_1$ to $Ar_3$, a, b, e, and f are as defined in formulae 3 to 7.

According to one embodiment of the present disclosure, the compound of formula 2 of the present disclosure may be represented by any one of the following formulae 12 to 16:

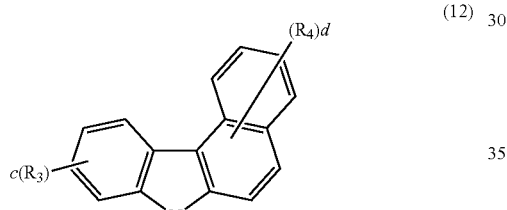
(12)

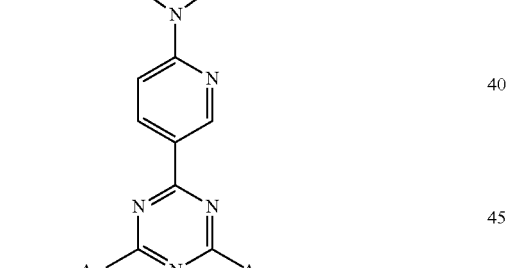
(13)

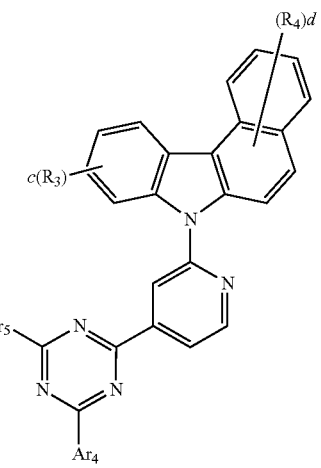
(14)

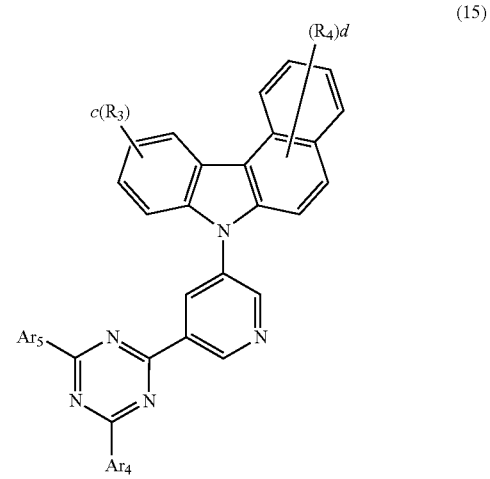
(15)

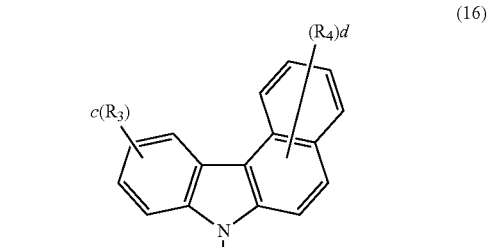
(16)

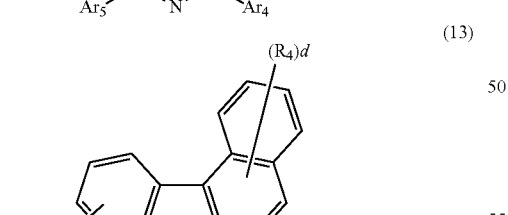

In formulae 12 to 16, $R_3$, $R_4$, $Ar_4$, $Ar_5$, c, and d are as defined in formula 2.

Herein, "(C1-C30)alkyl" indicates a linear or branched alkyl having 1 to 30, preferably 1 to 20, and more preferably 1 to 10 carbon atoms, and includes methyl, ethyl, n-propyl, isopropyl, n-butyl, isobutyl, tert-butyl, etc. "(C2-C30) alkenyl" indicates a linear or branched alkenyl having 2 to 30, preferably 2 to 20, and more preferably 2 to 10 carbon atoms and includes vinyl, 1-propenyl, 2-propenyl, 1-butenyl, 2-butenyl, 3-butenyl, 2-methylbut-2-enyl, etc. "(C2-C30)

alkynyl" indicates a linear or branched alkynyl having 2 to 30, preferably 2 to 20, and more preferably 2 to 10 carbon atoms and includes ethynyl, 1-propynyl, 2-propynyl, 1-butynyl, 2-butynyl, 3-butynyl, 1-methylpent-2-ynyl, etc. Herein, "(C3-C30)cycloalkyl" indicates a mono- or polycyclic hydrocarbon having 3 to 30, preferabley 3 to 20, more preferably 3 to 7 ring backbone carbon atoms. The cycloalkyl includes cyclopropyl, cyclobutyl, cyclopentyl, cyclohexyl, etc. Herein, "3 to 7-membered heterocycloalkyl" indicates a cycloalkyl having 3 to 7, preferably 5 to 7 ring backbone atoms including at least one heteroatom selected from B, N, O, S, Si, and P; preferably O, S, and N, and includes tetrahydrofuran, pyrrolidine, thiolan, tetrahydropyran, etc. Herein, "(C6-C30)aryl(ene)" indicates a monocyclic ring-type or fused ring-type radical derived from aromatic hydrocarbon having 6 to 30, preferabley 6 to 20 ring backbone carbon atoms wherein the (C6-C30)aryl(ene) may be partially saturated. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. Herein, "3 to 30-membered heteroaryl(ene)" indicates an aryl group having 3 to 30 ring backbone atoms including at least one, preferably 1 to 4, heteroatoms selected from the group consisting of B, N, O, S, Si, and P; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, naphtyridyl, carbazolyl, phenoxazinyl, phenanthridinyl, benzodioxolyl, etc. Further, "halogen" includes F, Cl, Br, and I.

Furthermore, herein, "substituted" in the expression, "substituted or unsubstituted," means that a hydrogen atom in a certain functional group is replaced with another atom or group, i.e. a substituent. The substituents of the substituted aryl(ene), the substituted heteroaryl(ene), the substituted alkyl, the substituted alkenyl, the substituted alkynyl, the substituted cycloalkyl, the substituted trialkylsilyl, the substituted triarylsilyl, the substituted dialkylarylsilyl, the substituted mono- or di-arylamino, the substituted phenyl, the substituted naphthyl, the substituted fluorenyl, the substituted dibenzothiophenyl, the substituted dibenzofuranyl, and the substituted, mono- or polycyclic, alicyclic or aromatic ring, or a combination of the alicyclic ring and the aromatic ring in $L_1$, A, $Ar_1$ to $Ar_5$, and $R_1$ to $R_{14}$ of formulae 1 to 11 of the present disclosure, each independently, are at least one selected from the group consisting of deuterium, a halogen; a cyano; a carboxy; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a 3- to 7-membered heterocycloalkyl; a (C6-C30)aryloxy; a (C6-C30)arylthio; a 3- to 30-membered heteroaryl unsubstituted or substituted with a (C6-C30)aryl or di(C6-C30)arylamino; a (C6-C30)aryl unsubstituted or substituted with a cyano, a 3- to 30-membered heteroaryl or a tri(C6-C30)arylsilyl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl; and preferably, each independently, are at least one selected from the group consisting of a (C1-C20)alkyl, and an unsubstituted (C6-C25)aryl; more preferably, each independently, are at least one selected from the group consisting of a (C1-C10)alkyl, and an unsubstituted (C6-C18)aryl; and the substituent may include methyl, an unsubstituted naphthyl or an unsubstituted phenanthrenyl.

The first host compound of formula 1 of the present disclosure includes the following, but is not limited thereto:

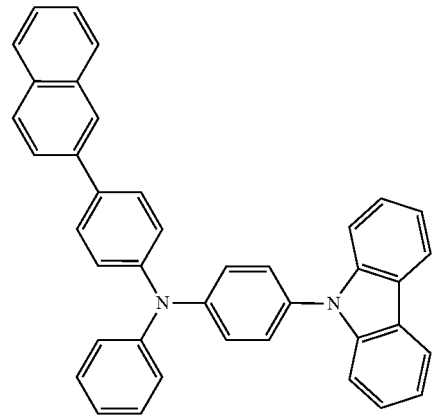

H1-1

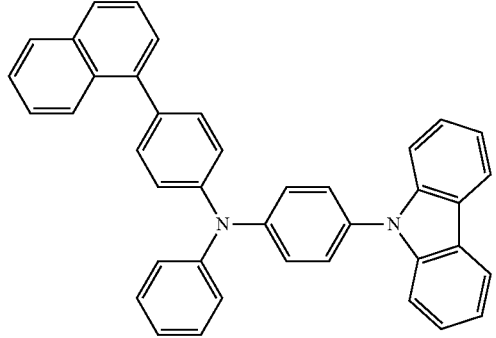

H1-2

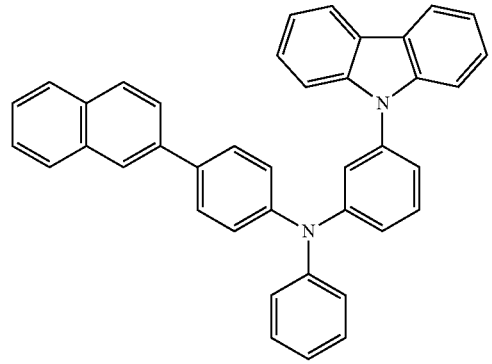

H1-3

H1-4
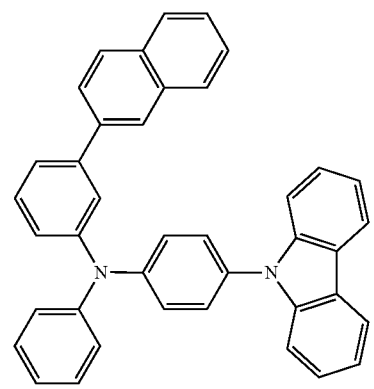
H1-5
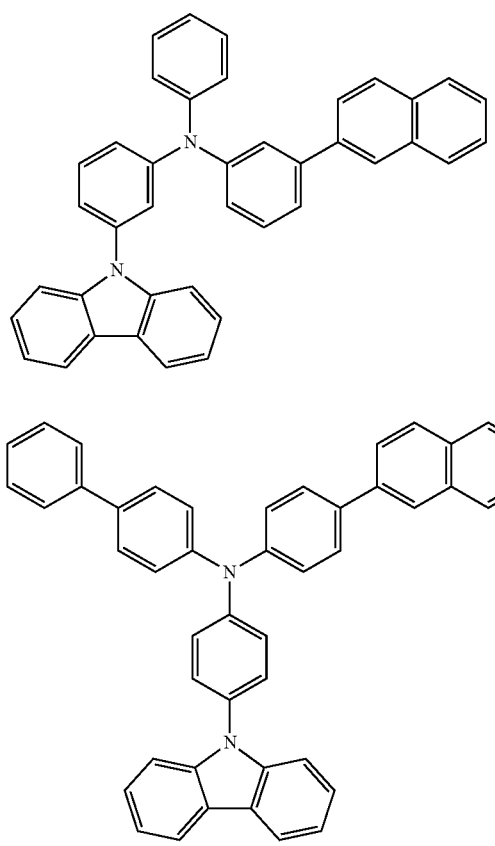
H1-6
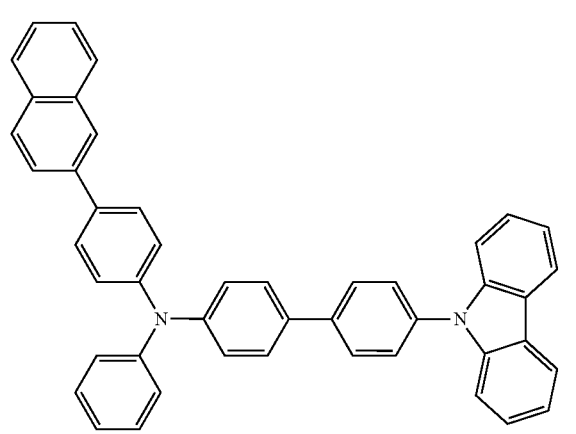
H1-8
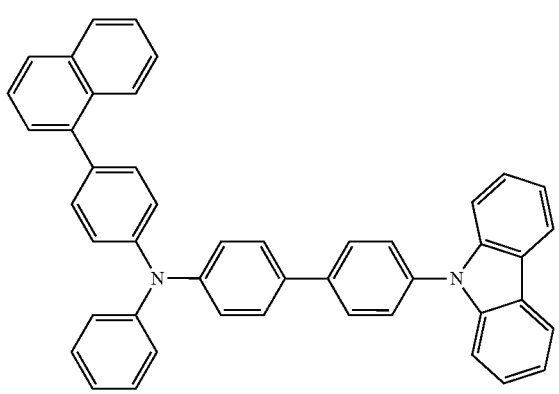
H1-9
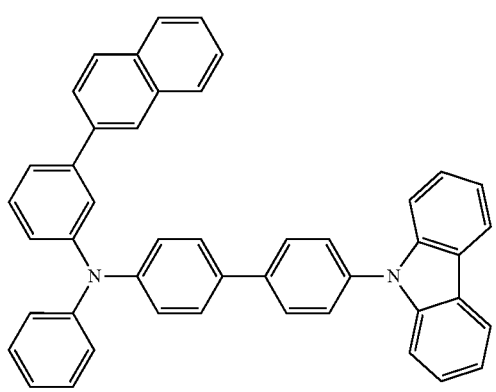
H1-7
H1-10

H1-11
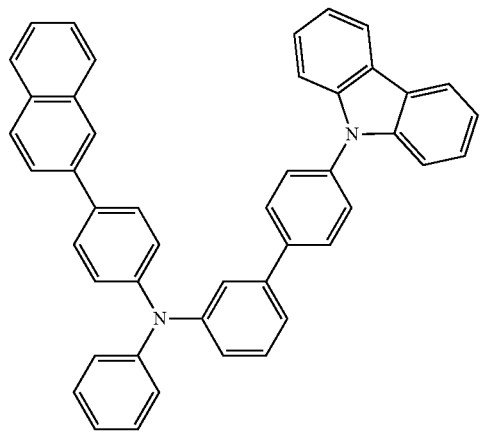
H1-12
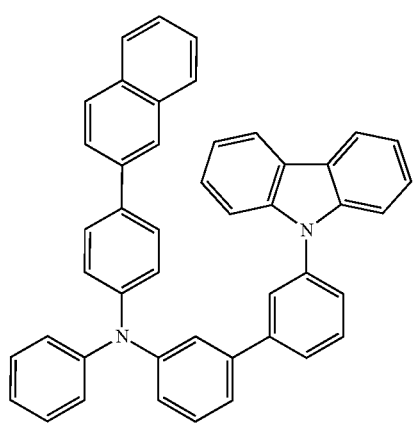
H1-13
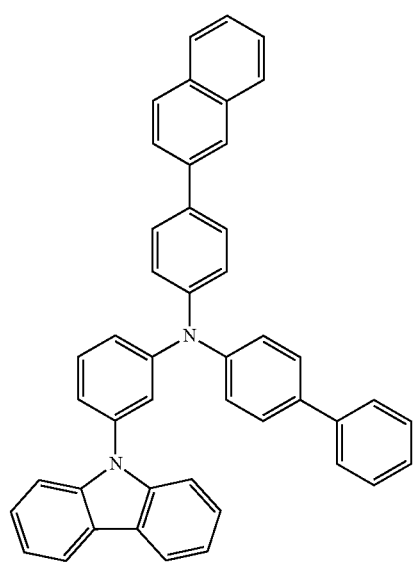
H1-14
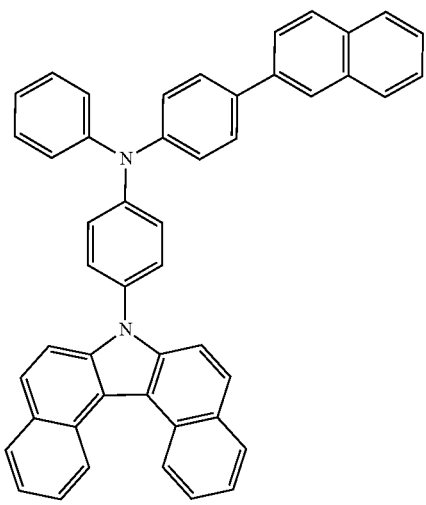
H1-15
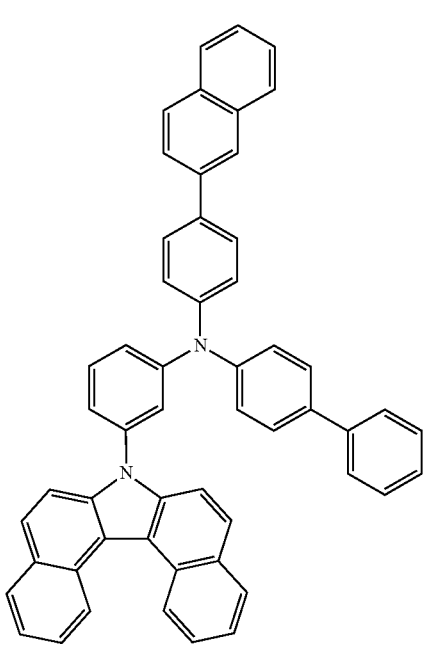
H1-16
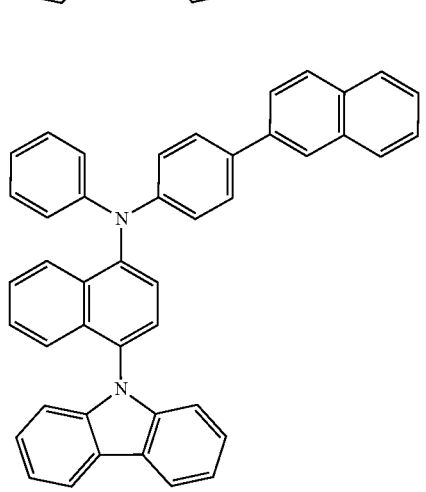

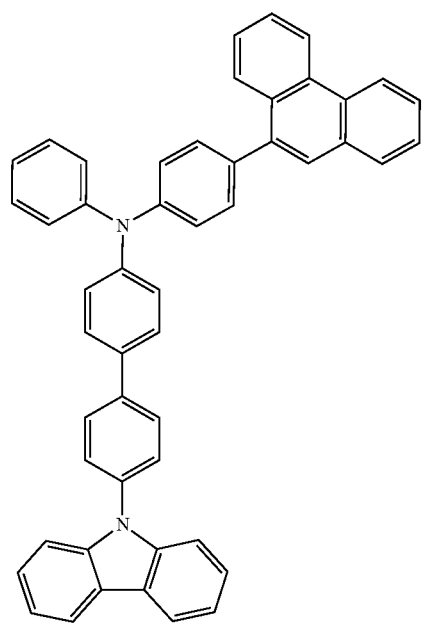
H1-17
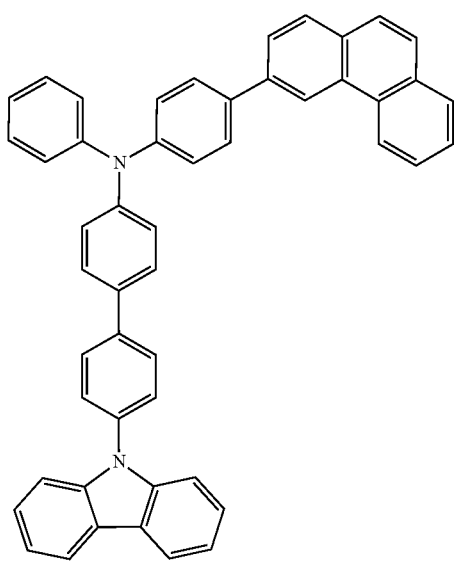
H1-18
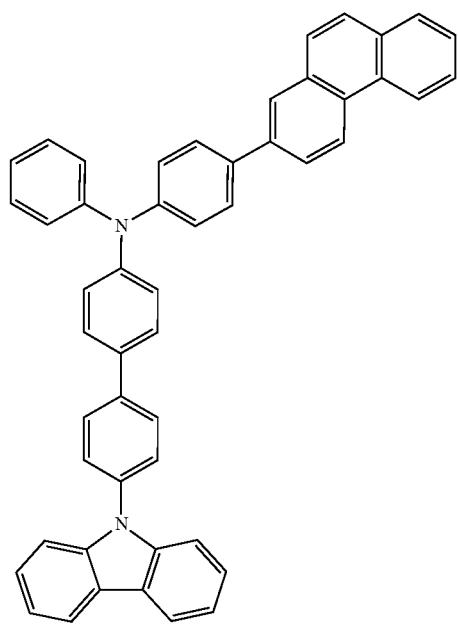
H1-19
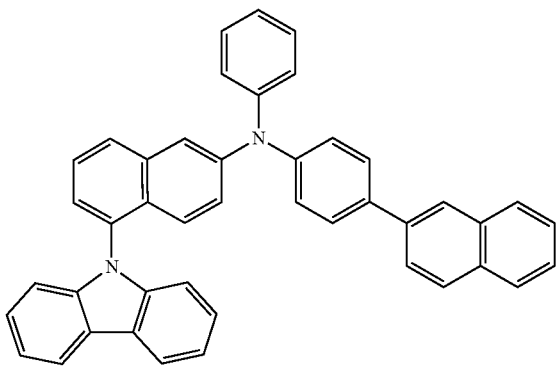
H1-20
H1-21

H1-22
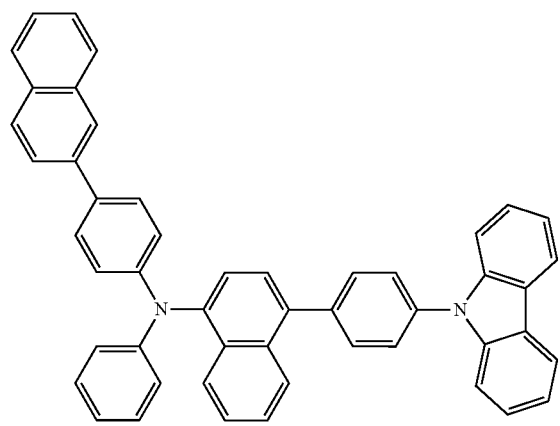
H1-23
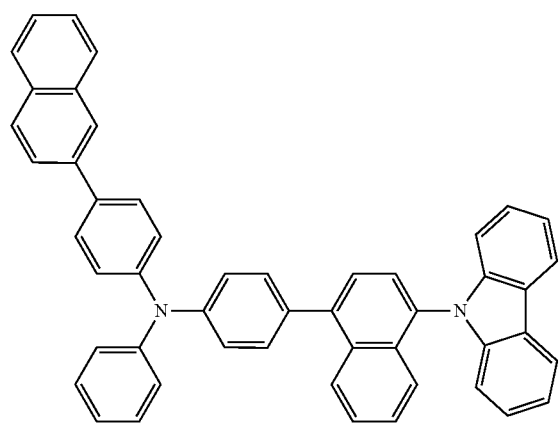
H1-24
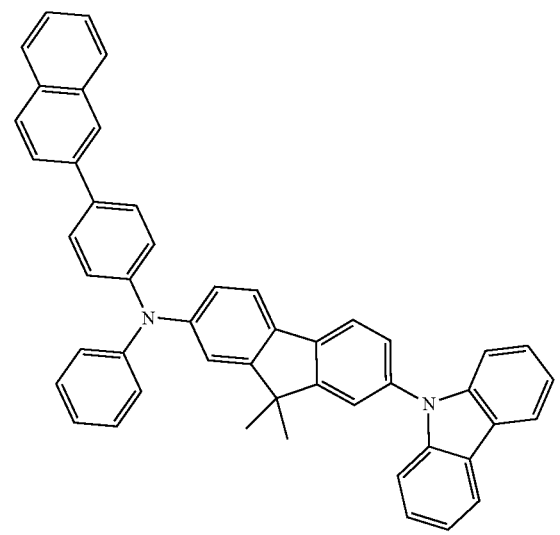
H1-25
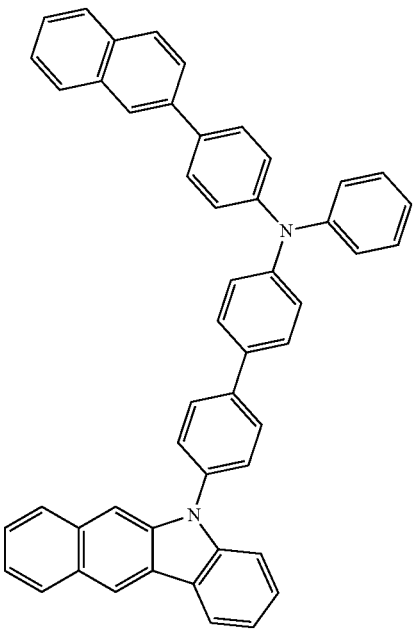
H1-26
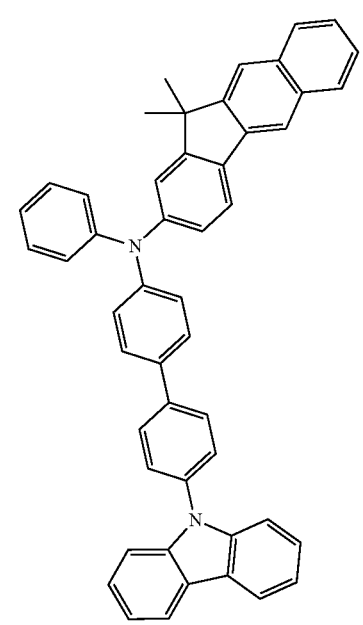

H1-27
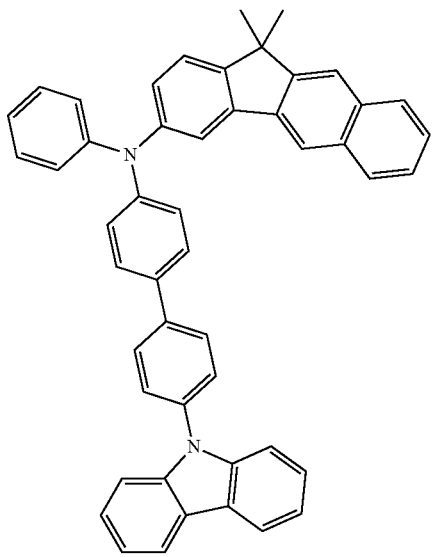
H1-28
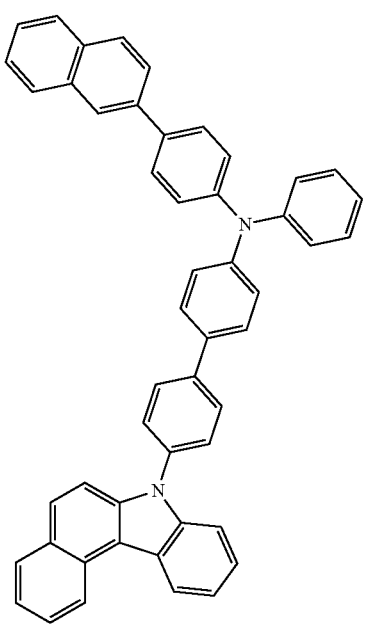
H1-29
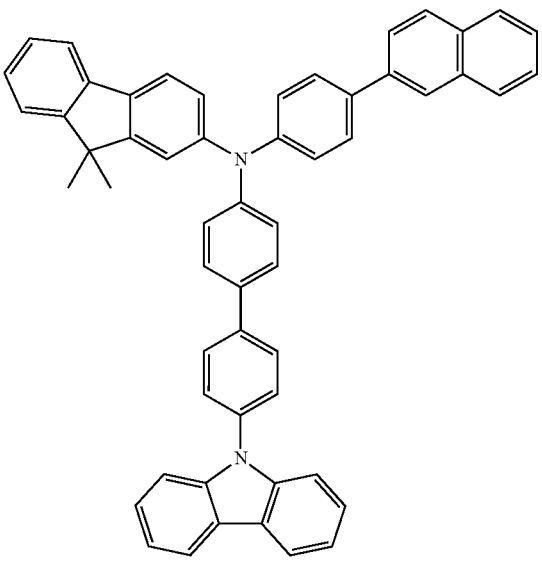
H1-30
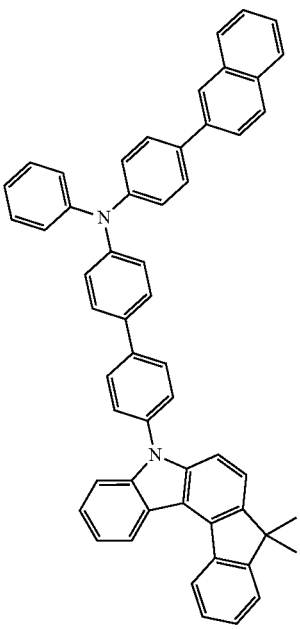

H1-31
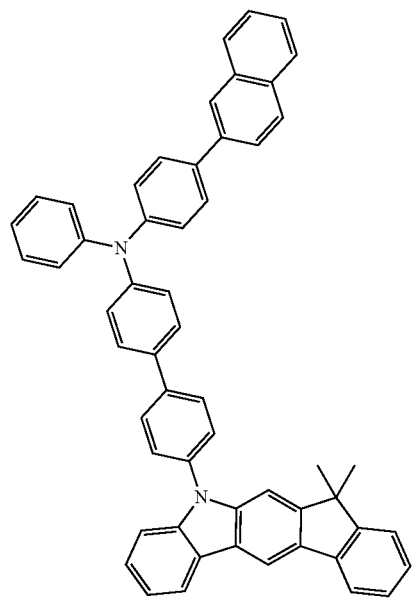
H1-32
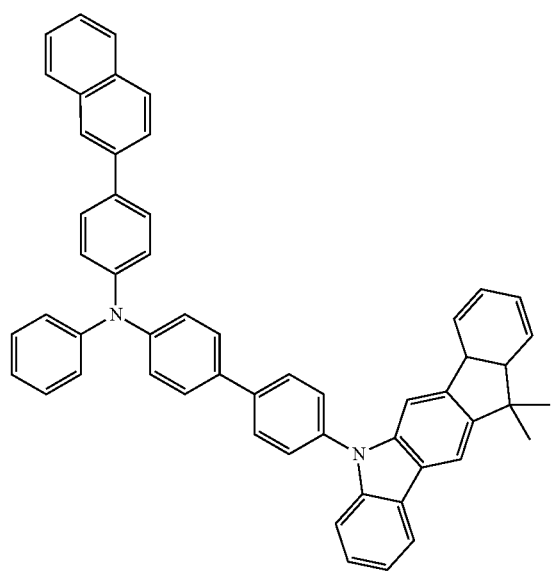
H1-33
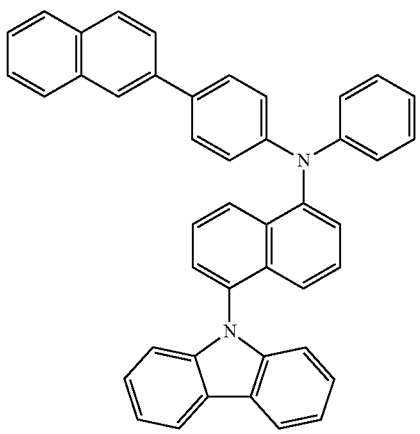
H1-34
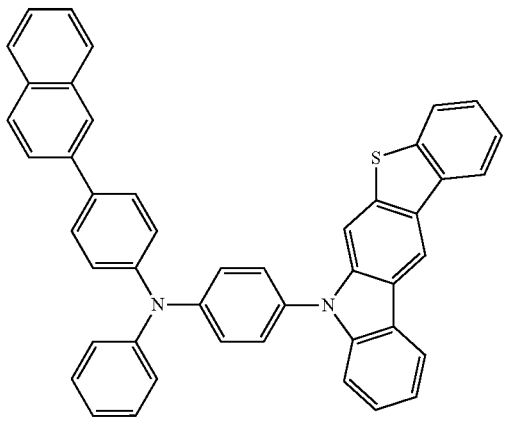
H1-35
H1-36
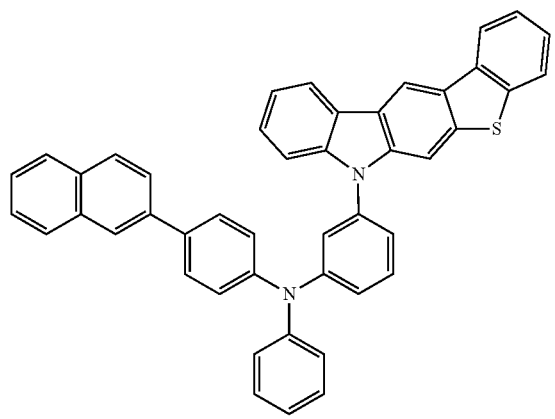

H1-37
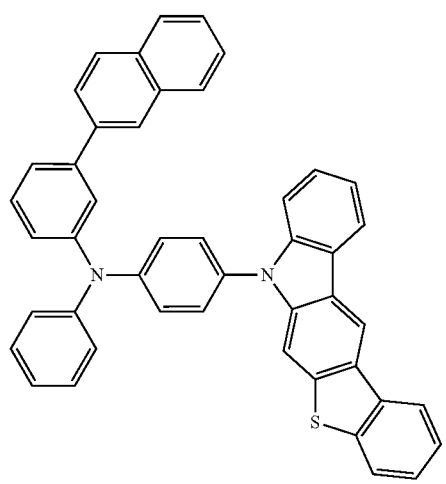
H1-38
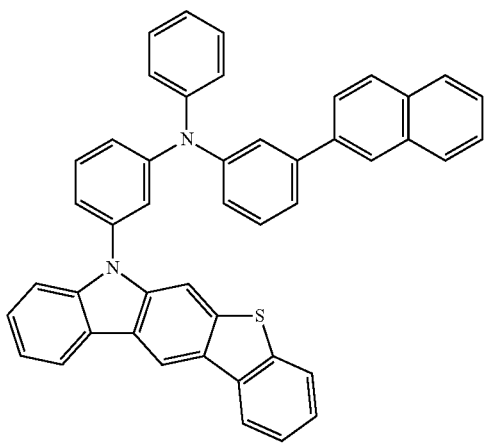
H1-39
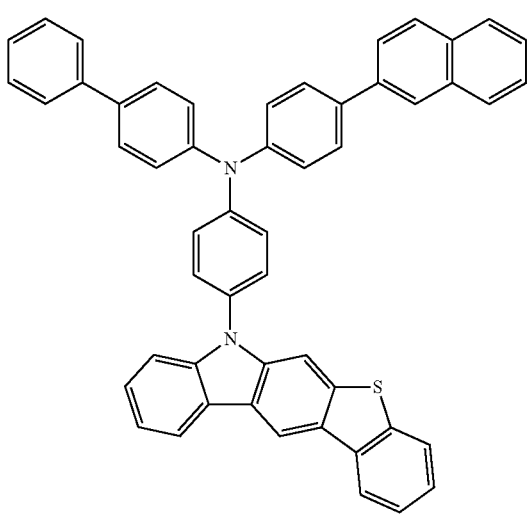
H1-40
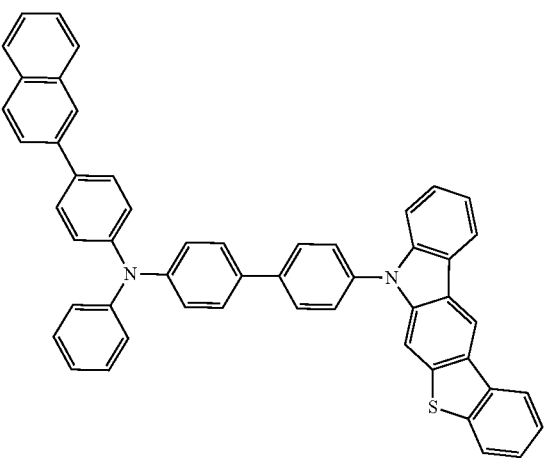
H1-41
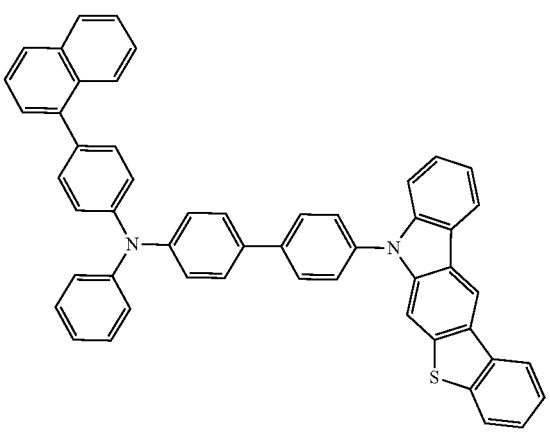
H1-42
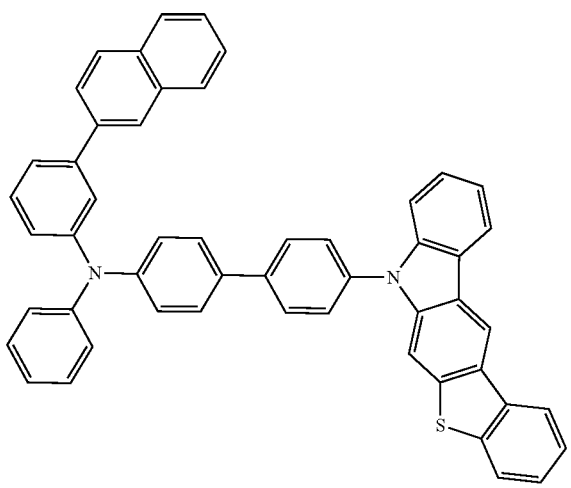

H1-43
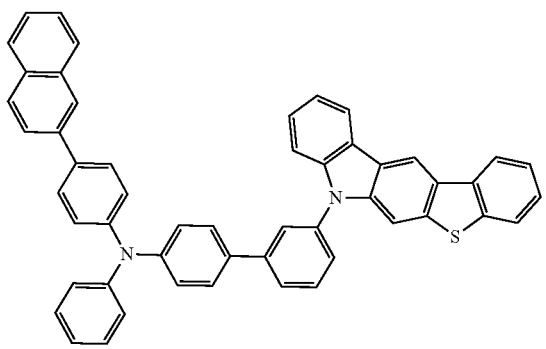
H1-44
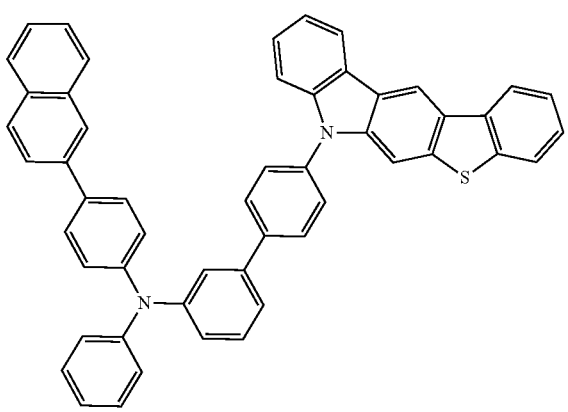
H1-45
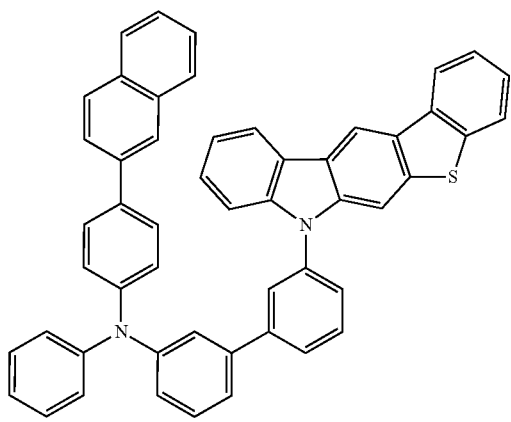
H1-46
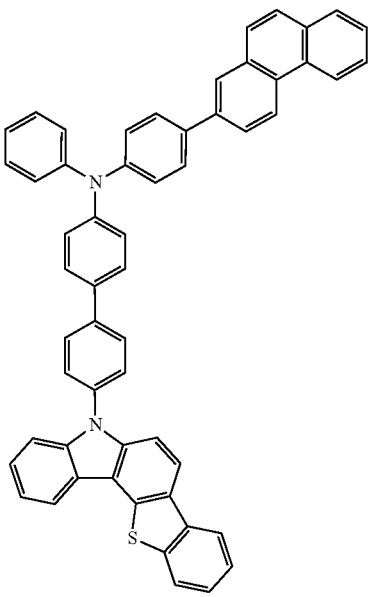
H1-47
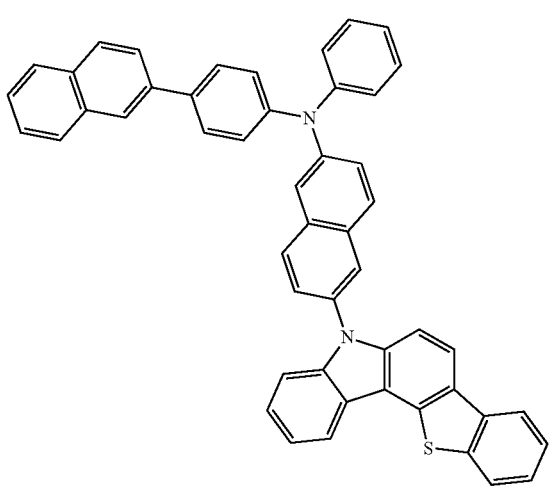
H1-48
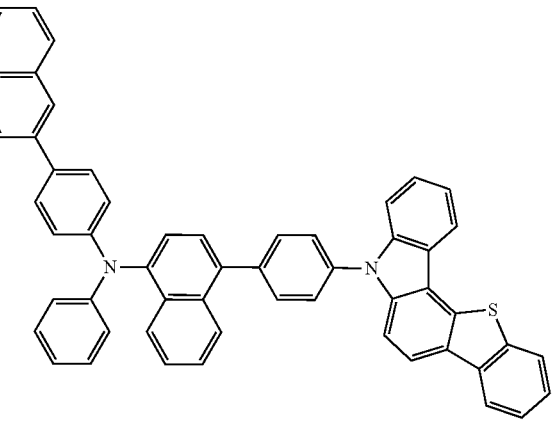

H1-49
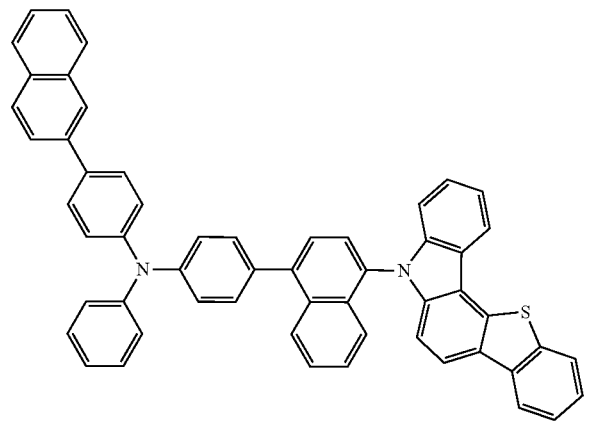
H1-50
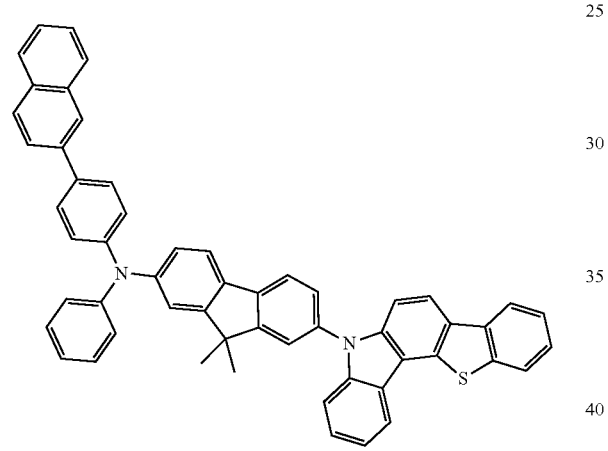
H1-51
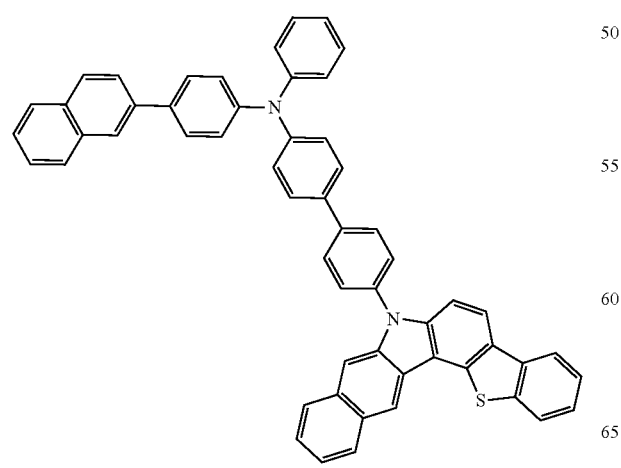
H1-52
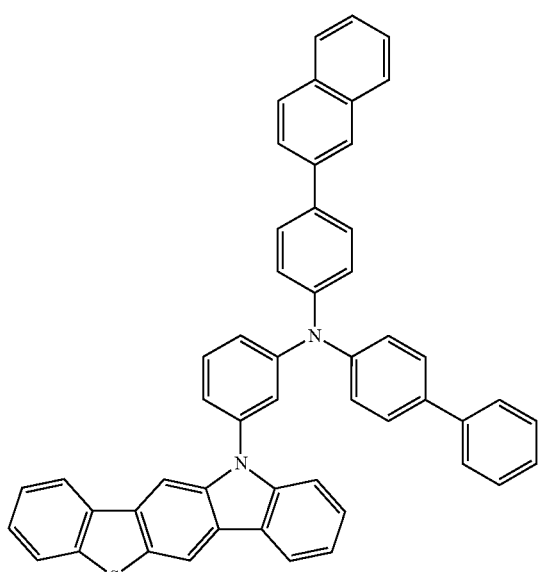
H1-53
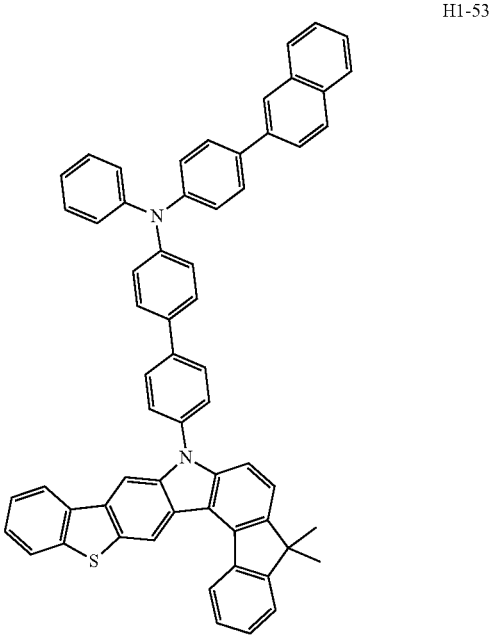

H1-54
H1-55
H1-56
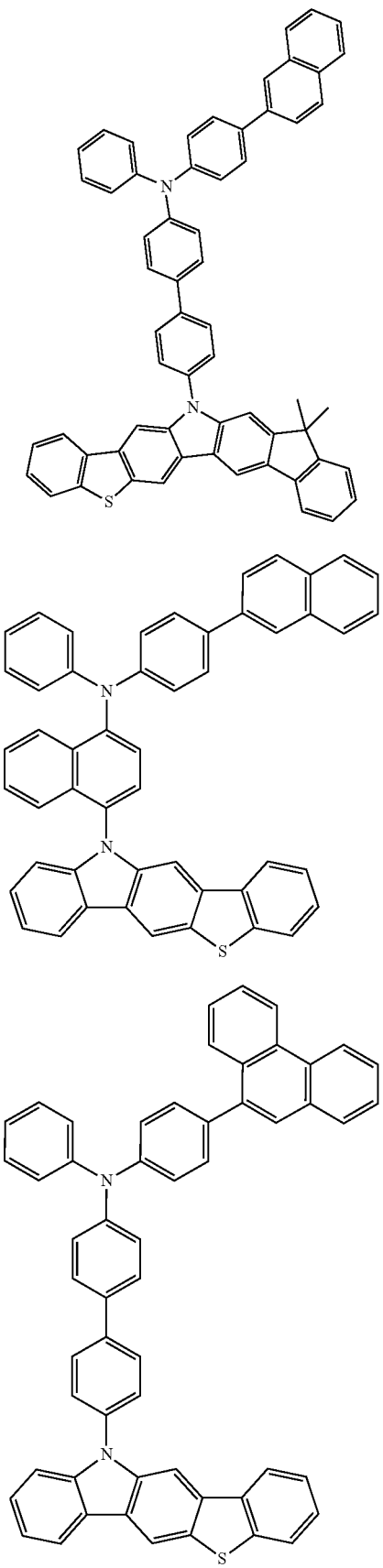
H1-57
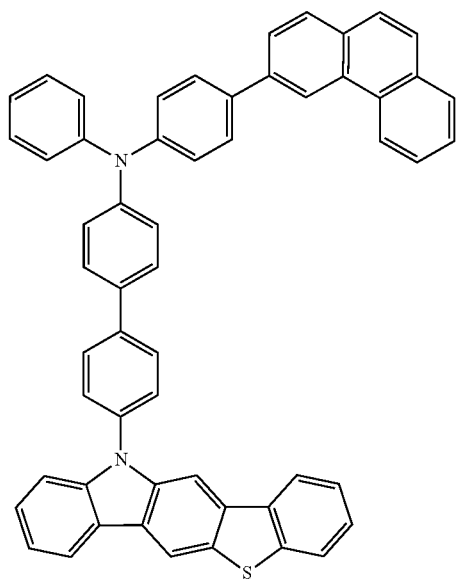
H1-58
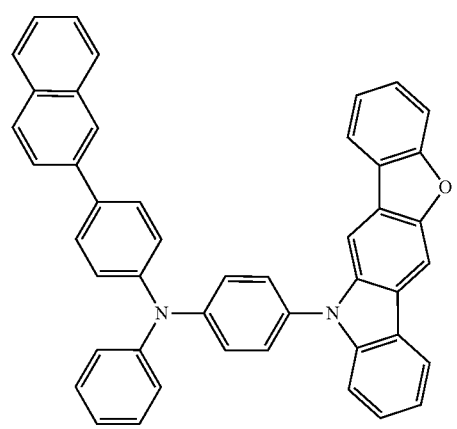
H1-59
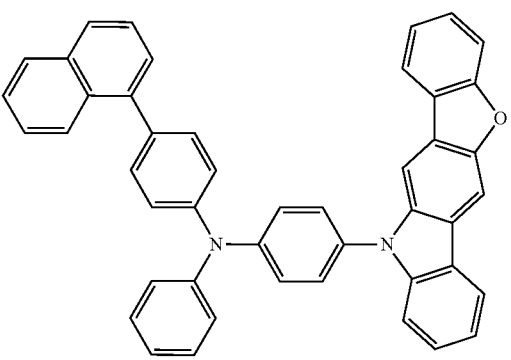

-continued
H1-60
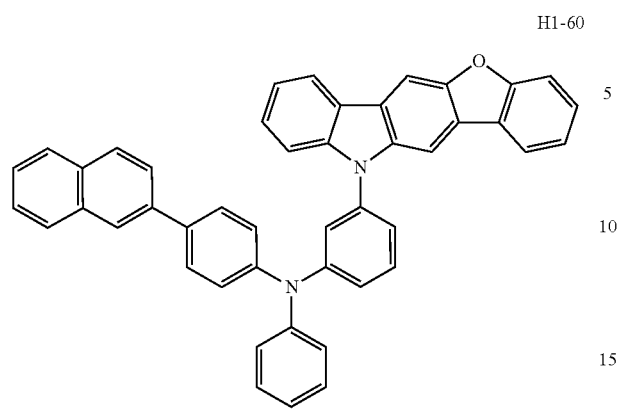
H1-61
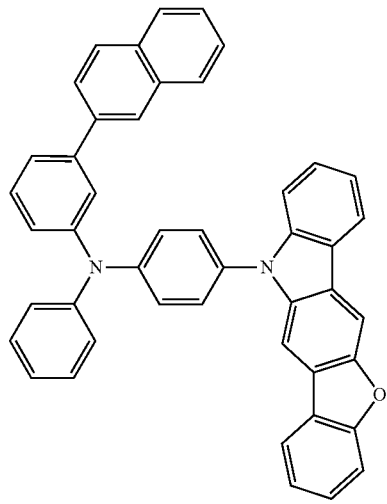
H1-62
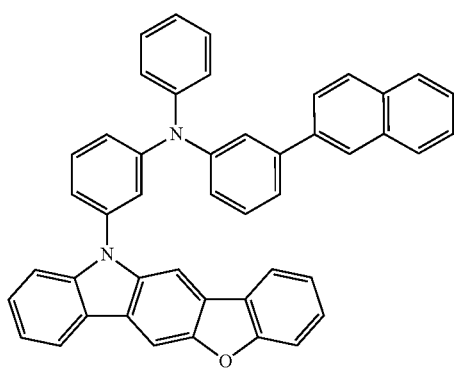
-continued
H1-63
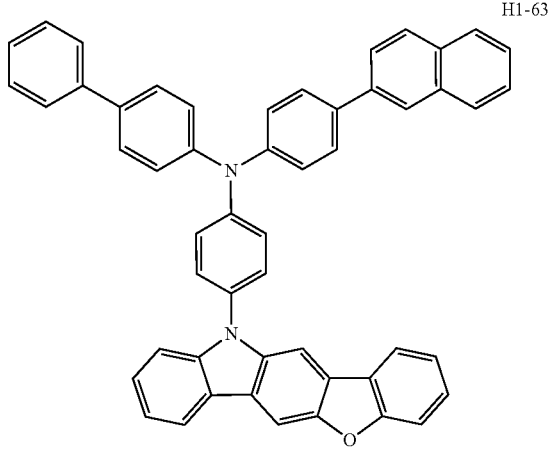
H1-64
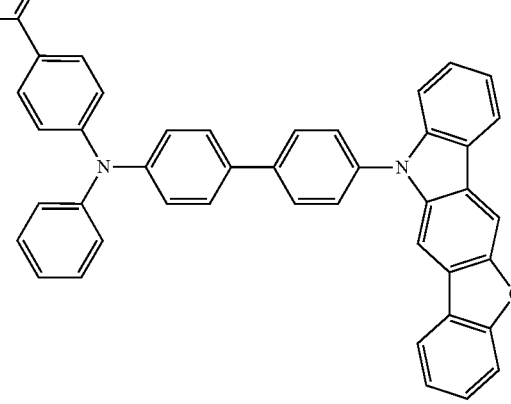
H1-65
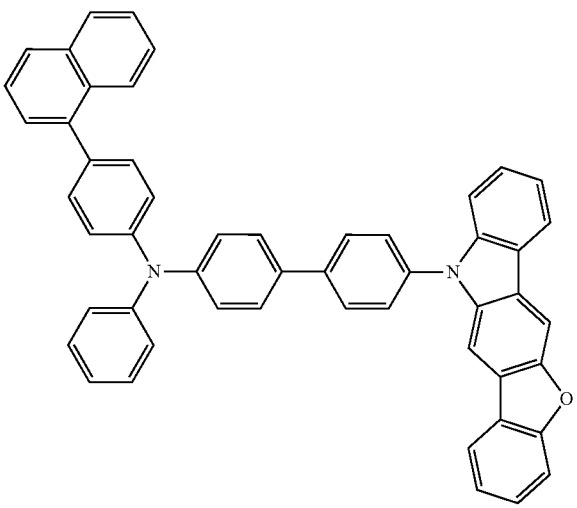

H1-66
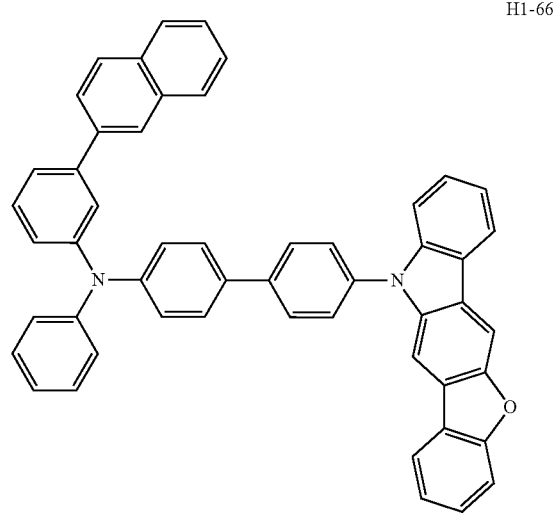
H1-67
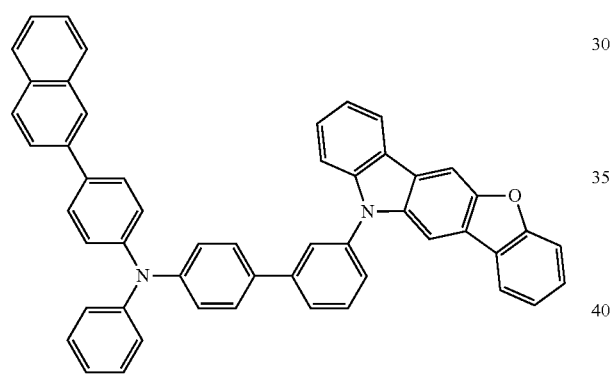
H1-68
H1-69
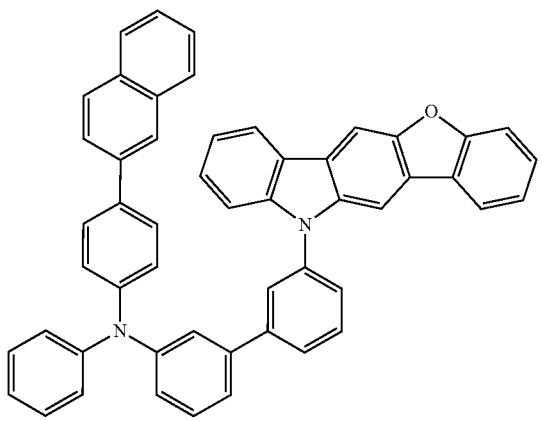
H1-70
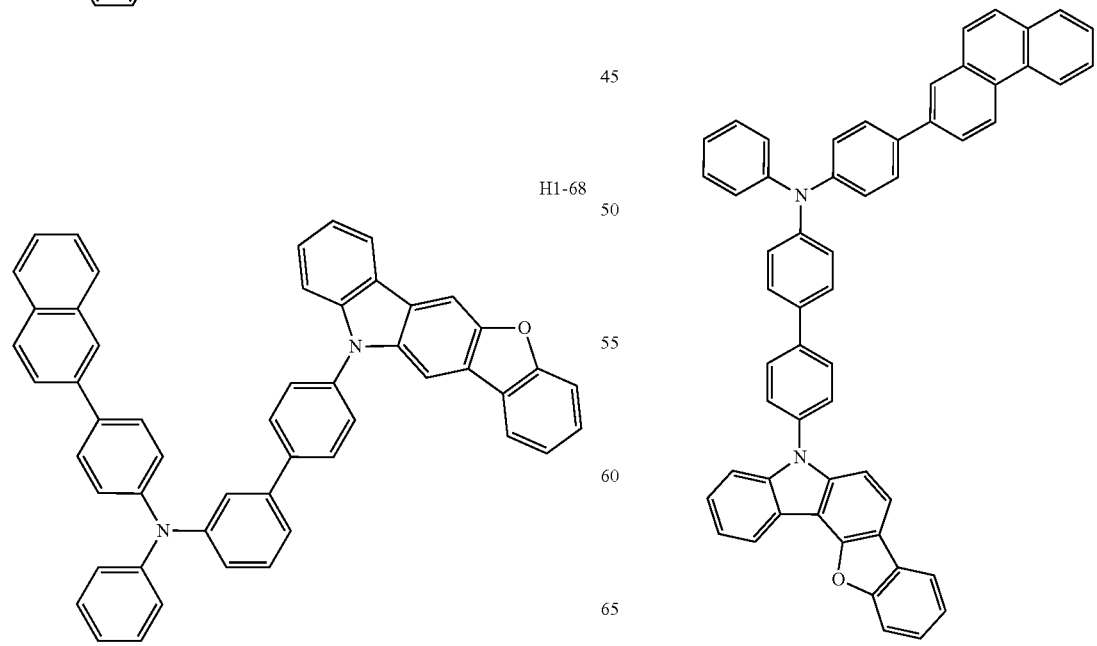

H1-71
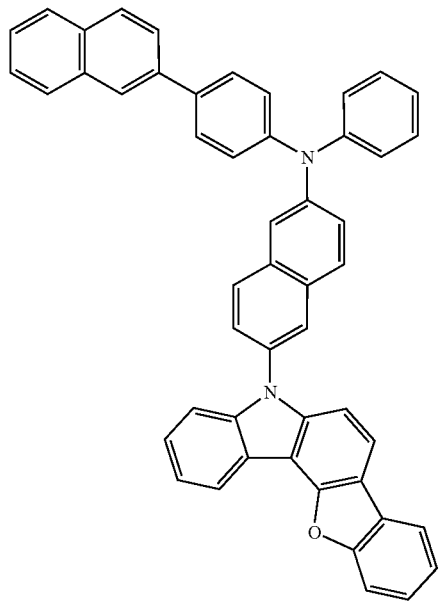
H1-74
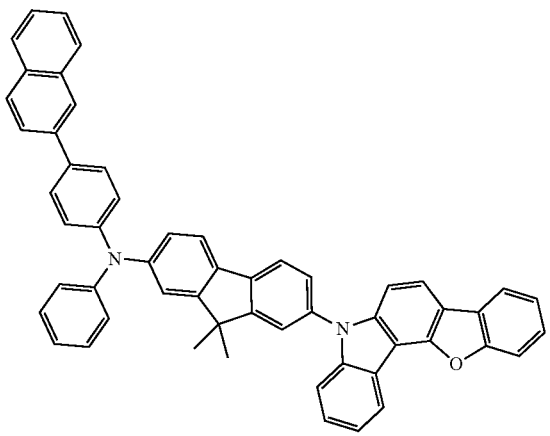
H1-72
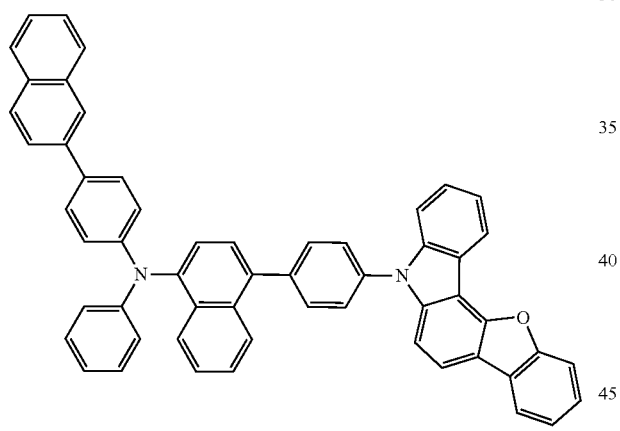
H1-73
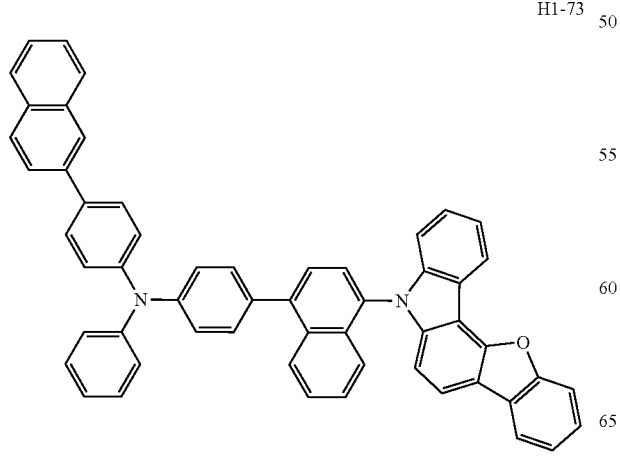
H1-75
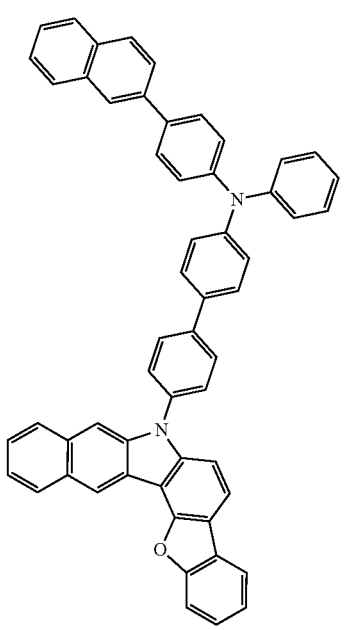

-continued
H1-76
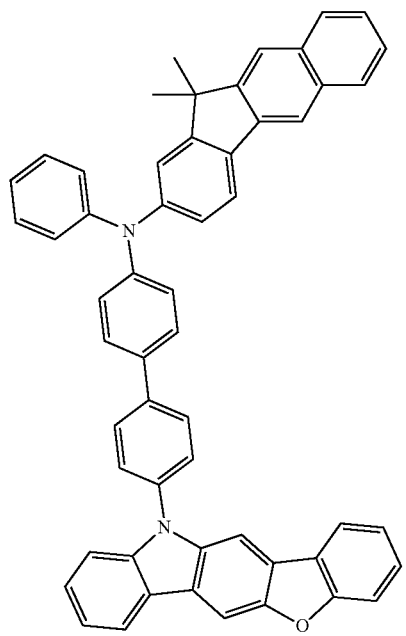
H1-77
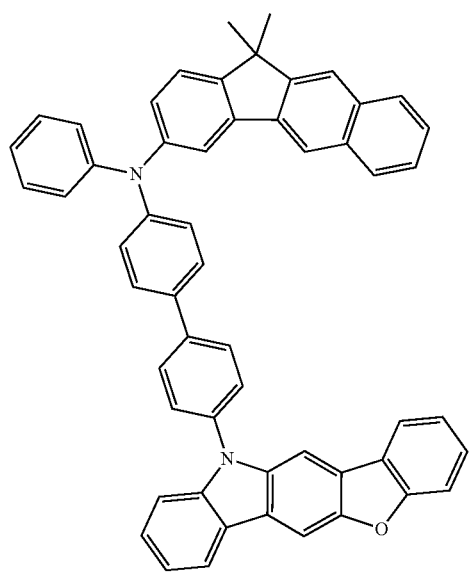
H1-78
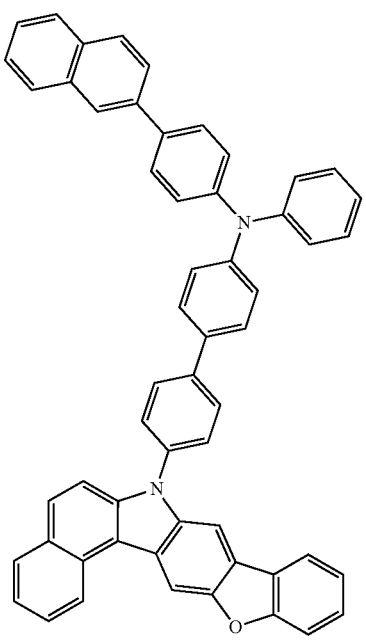
H1-79
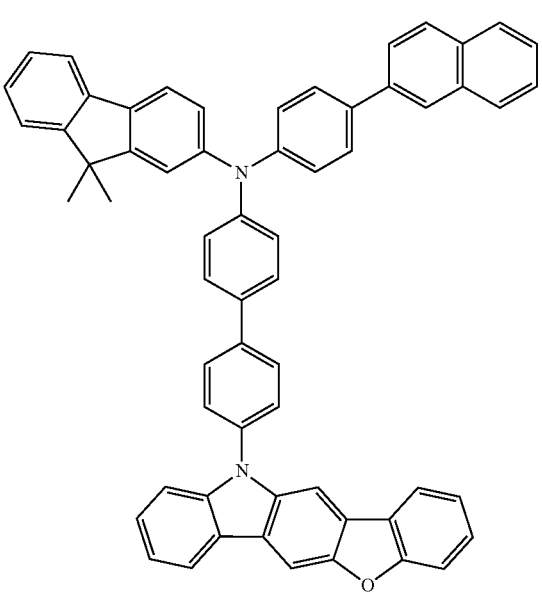

H1-80
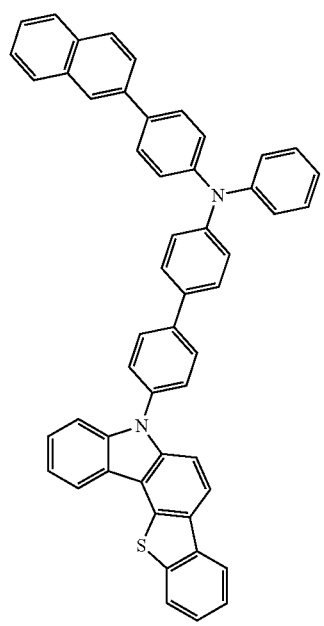
H1-81
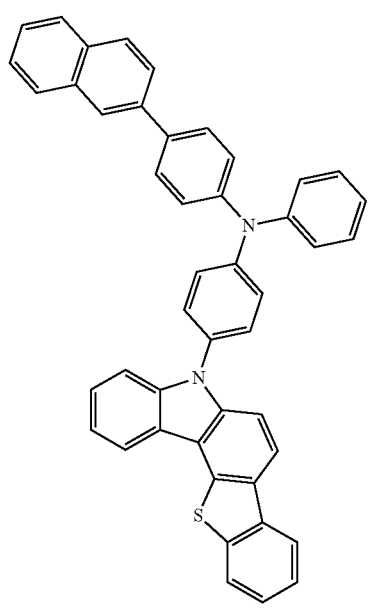
H1-82
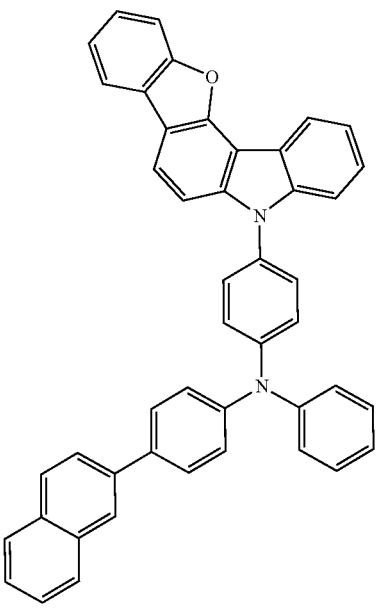
H1-83
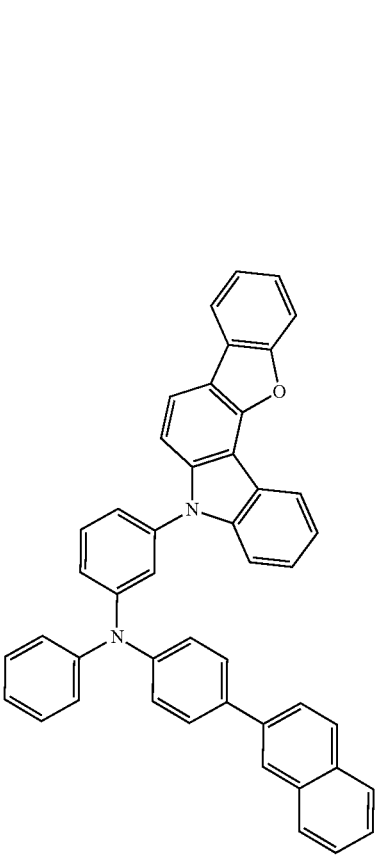

H1-84
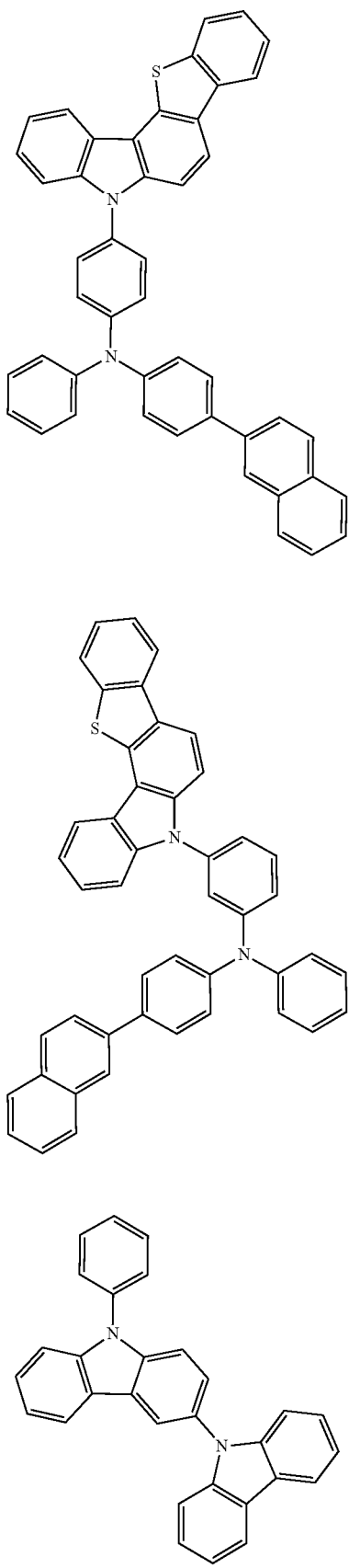
H1-85
H1-86
H1-87
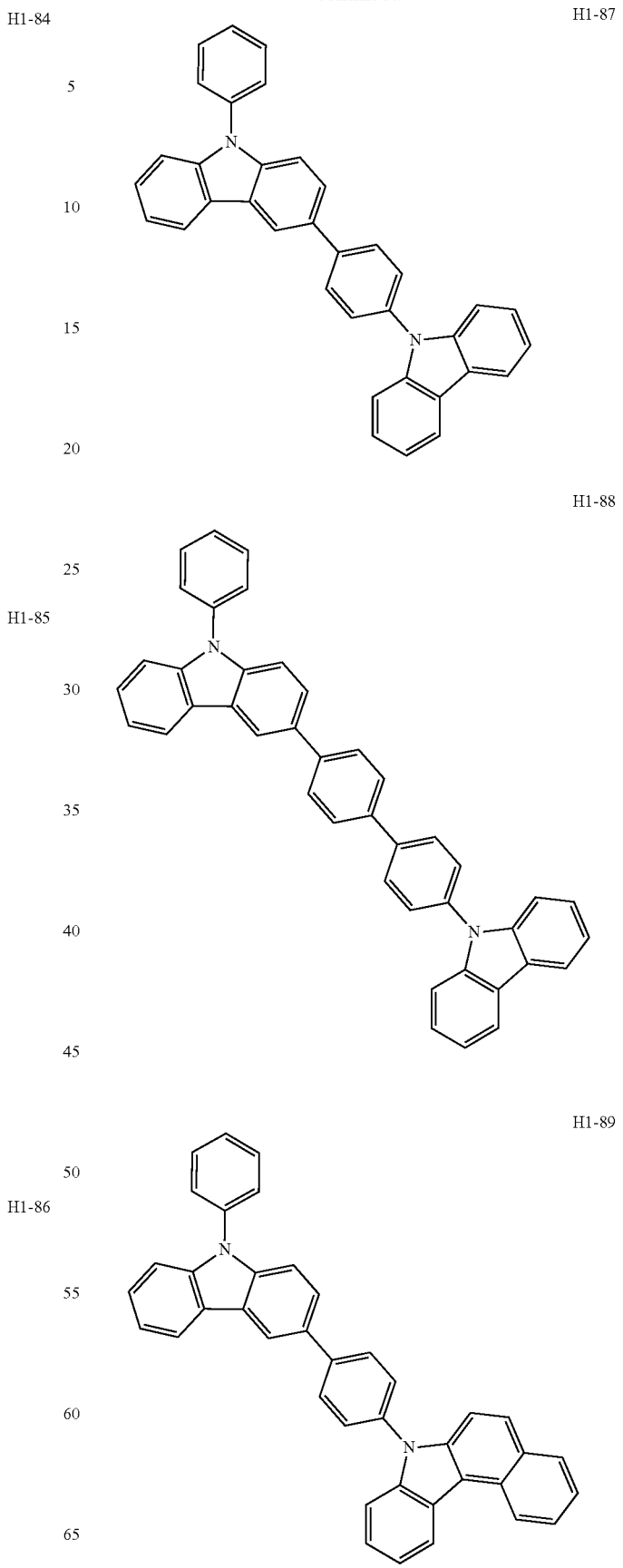
H1-88
H1-89

H1-90
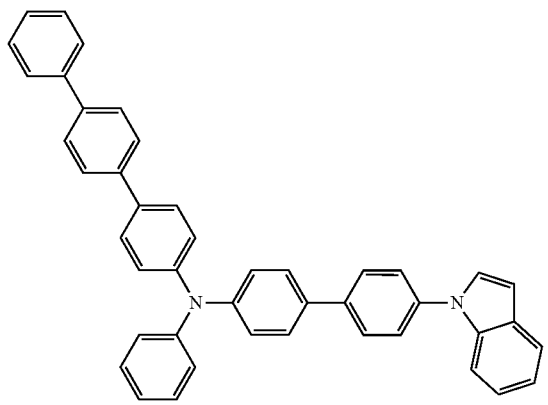
H1-93
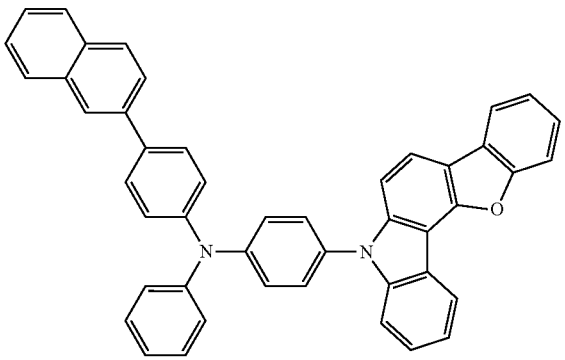
H1-91
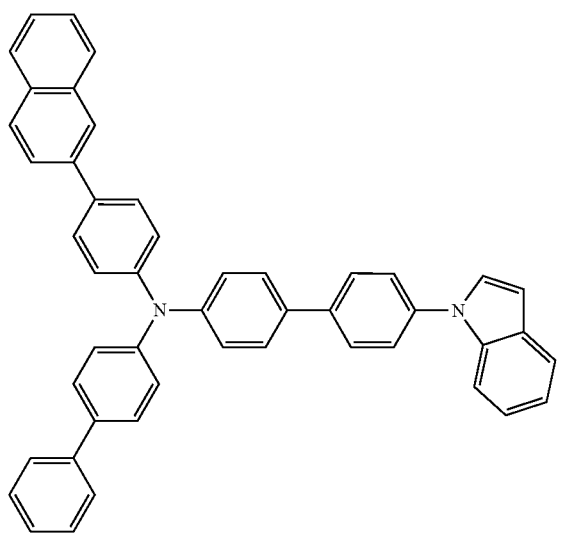
H1-94
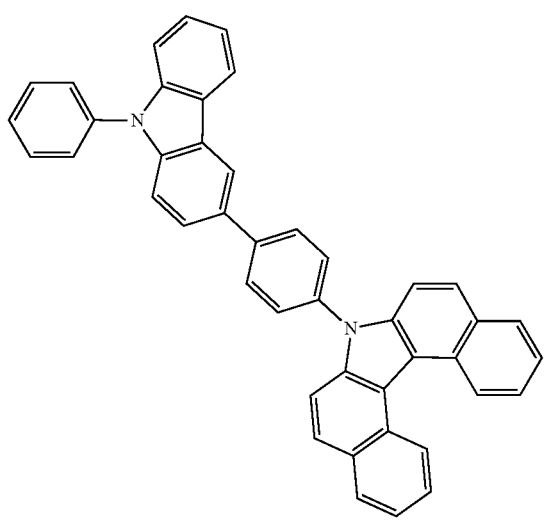
The second host compound of formula 2 above of the present disclosure includes the following, but is not limited thereto:
H1-92
H2-1
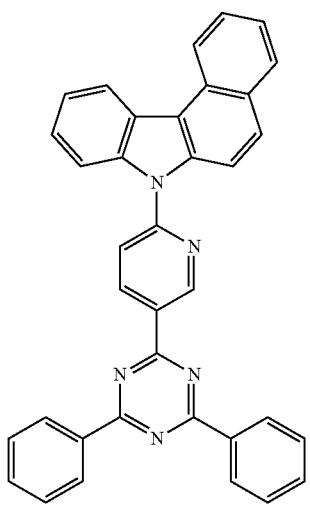

-continued
H2-2
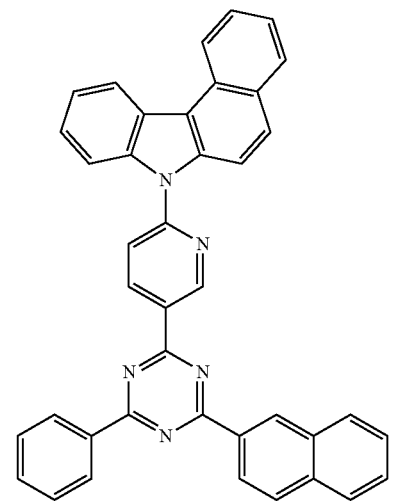
H2-3
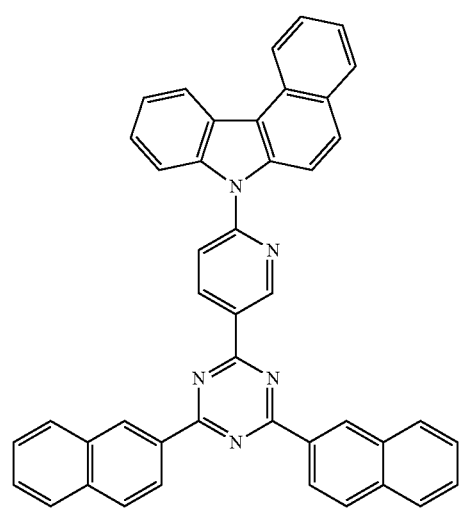
H2-4
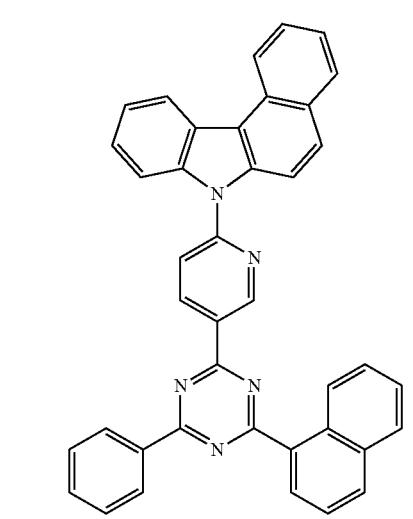
-continued
H2-5
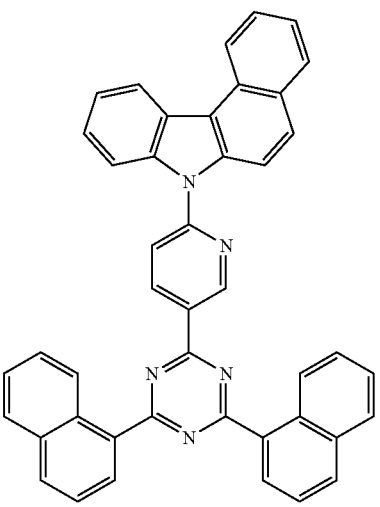
H2-6
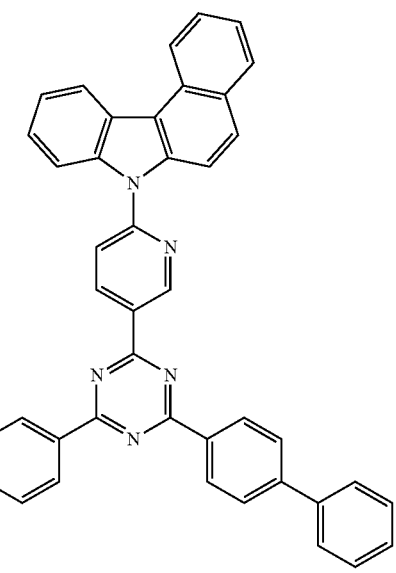
H2-7
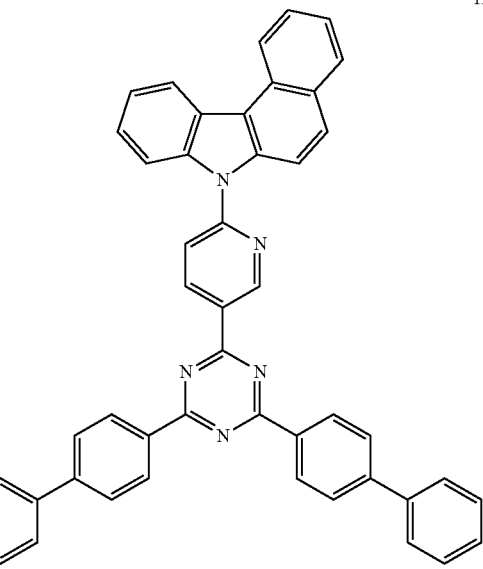

H2-8
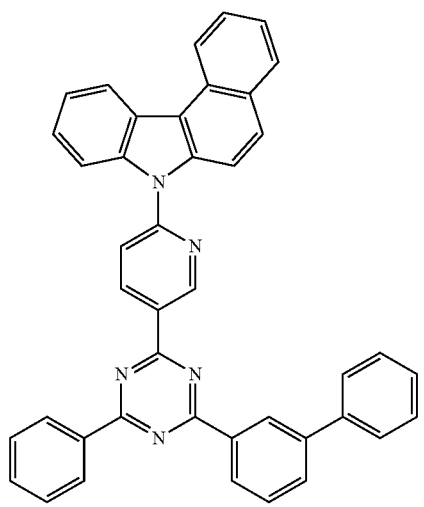
H2-9
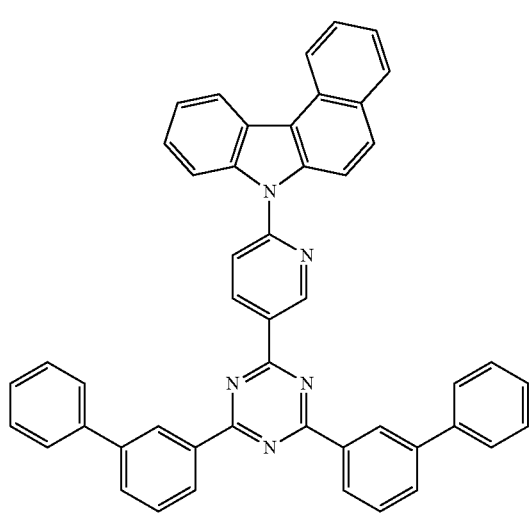
H2-10
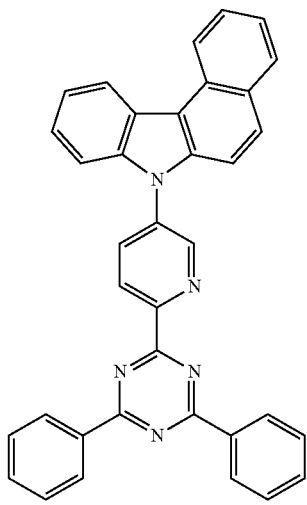
H2-11
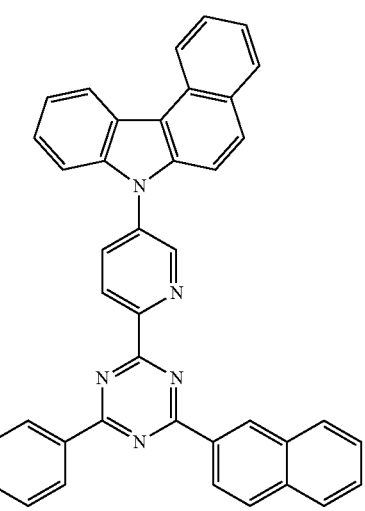
H2-12
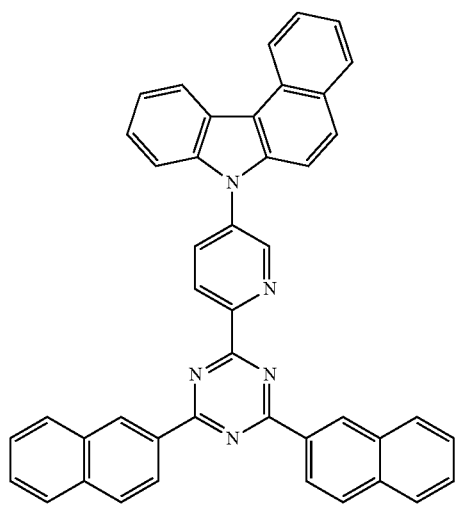
H2-13
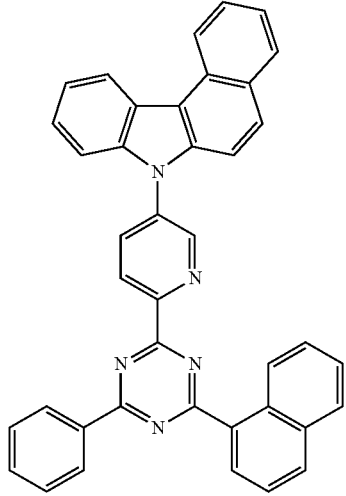

H2-14
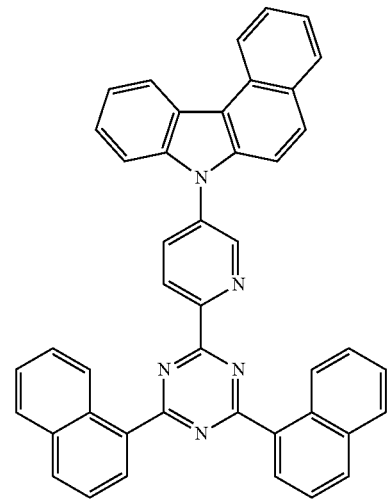
H2-15
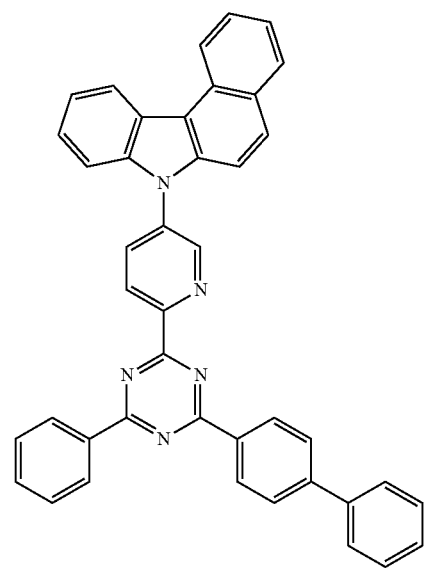
H2-16
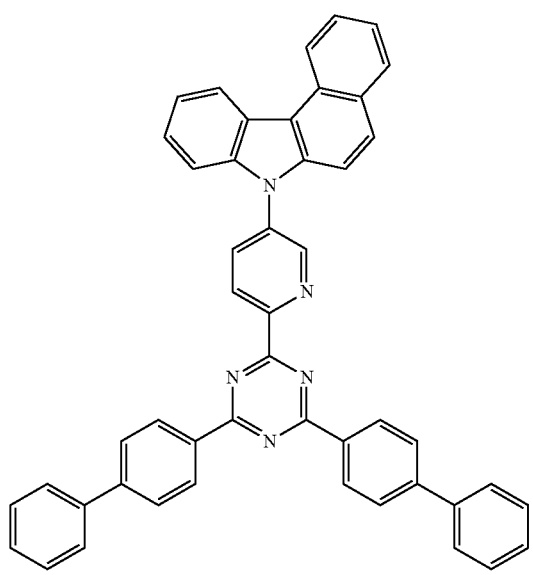
H2-17
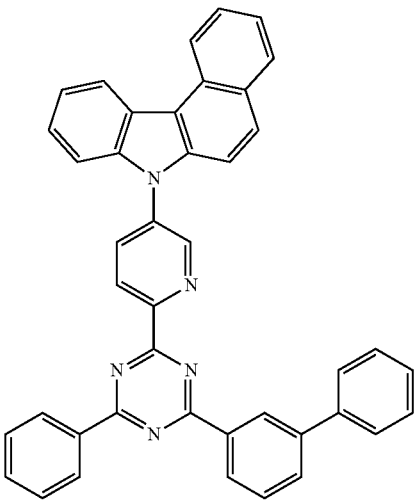
H2-18
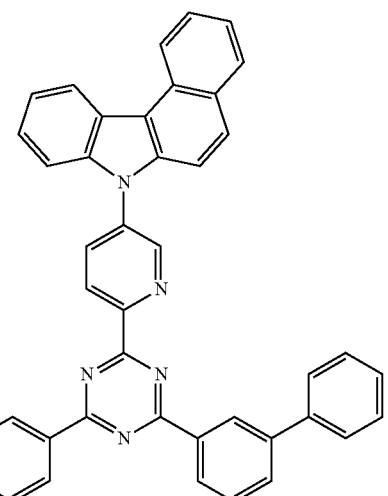
H2-28
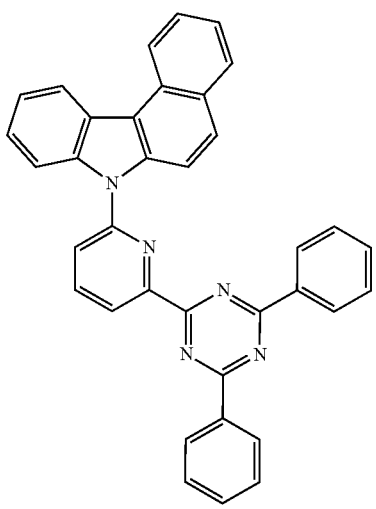

H2-29
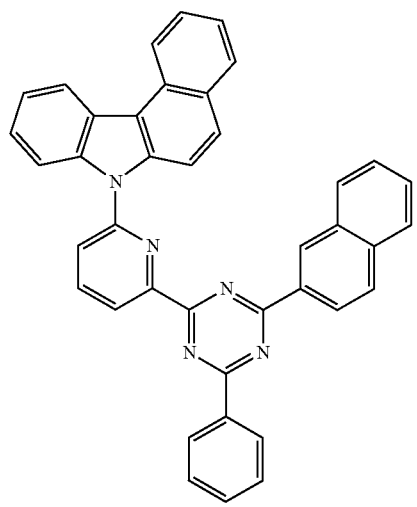
H2-30
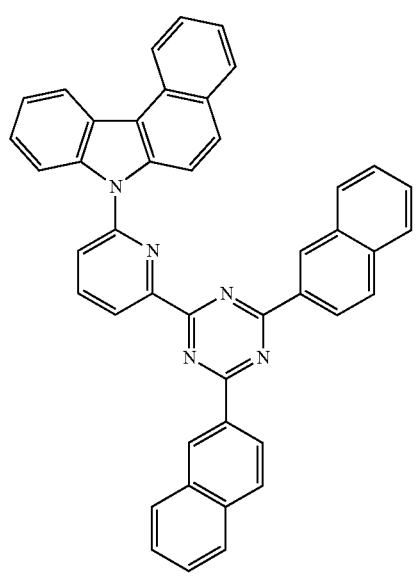
H2-31
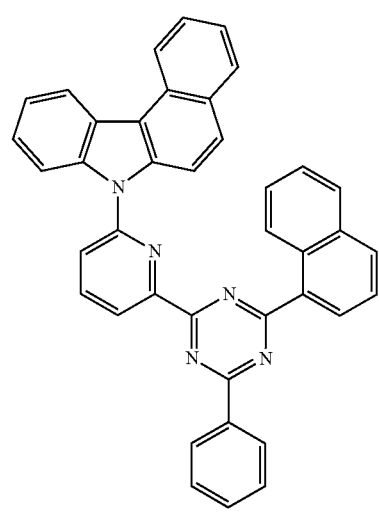
H2-32
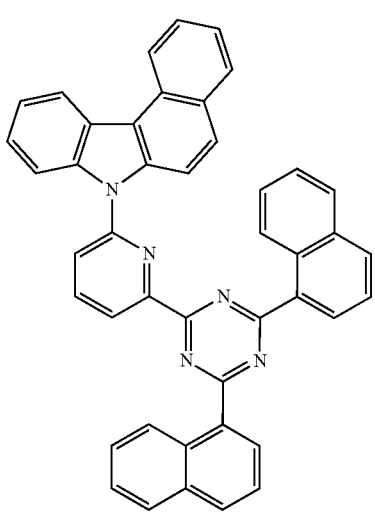
H2-33
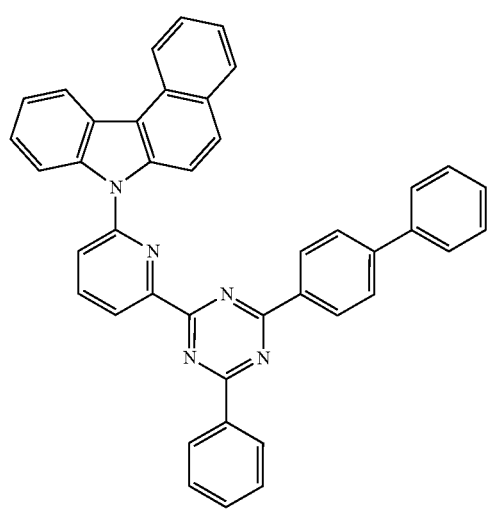
H2-34
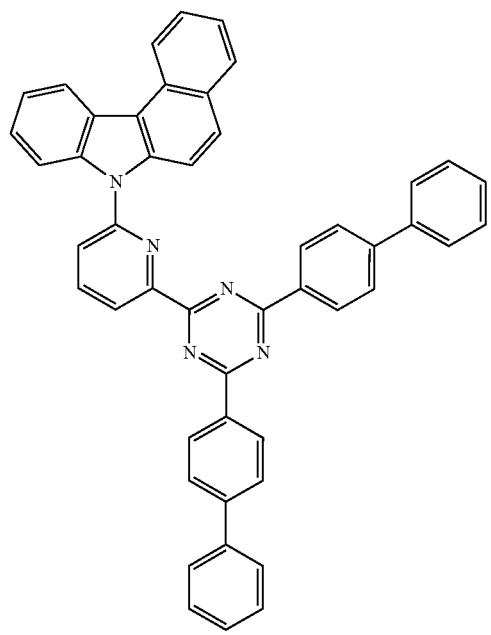

H2-35
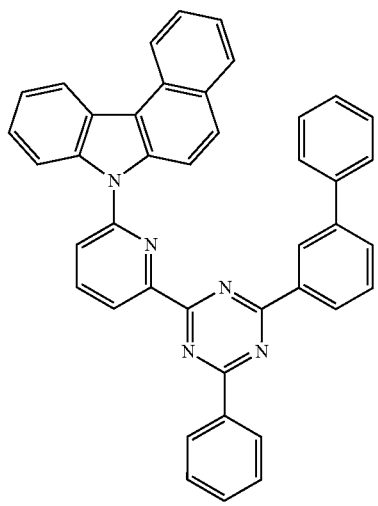
H2-38
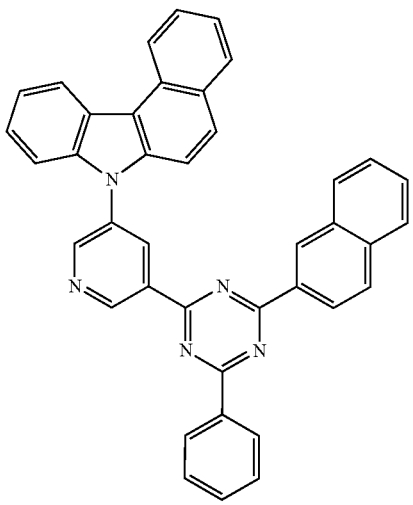
H2-36
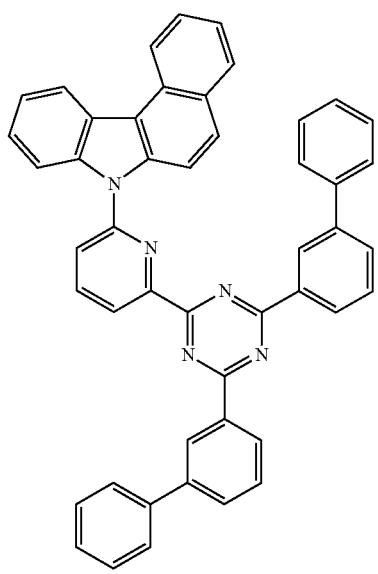
H2-39
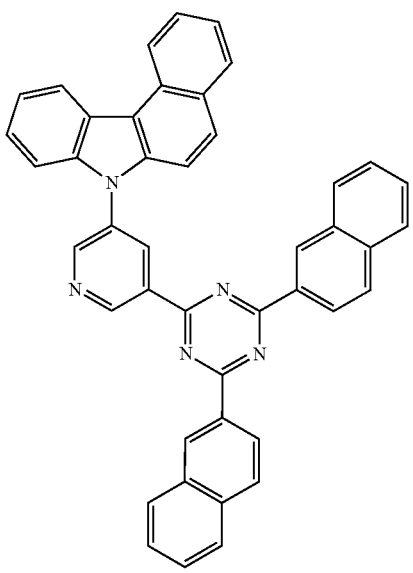
H2-37
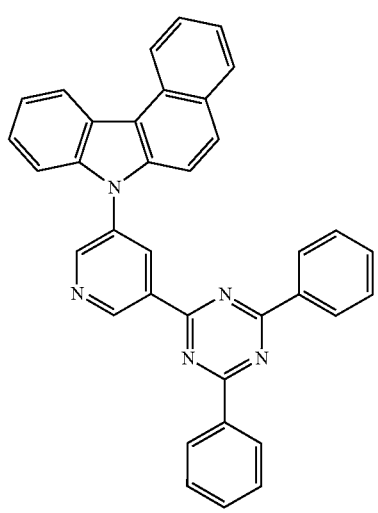
H2-40
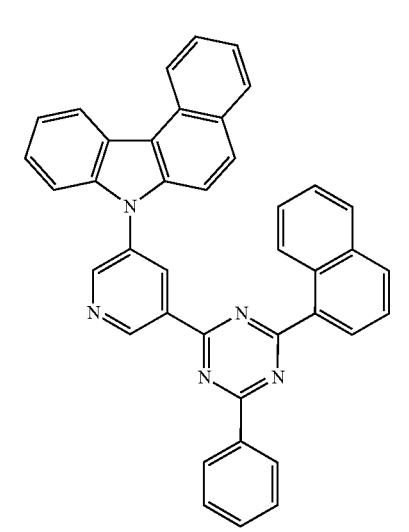

H2-41
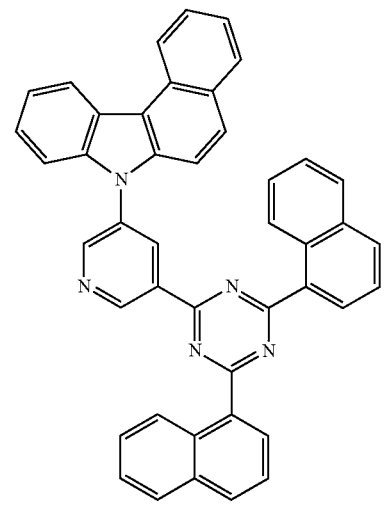
H2-42
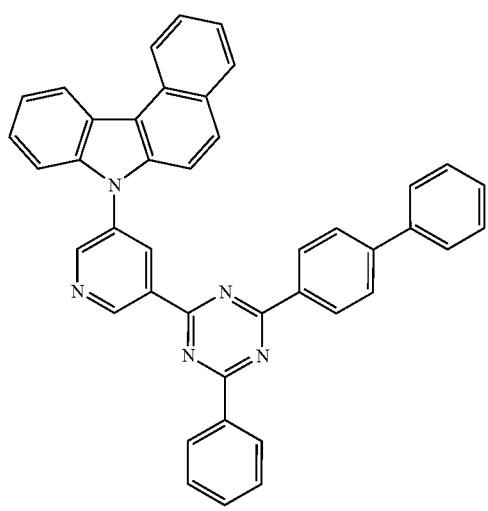
H2-43
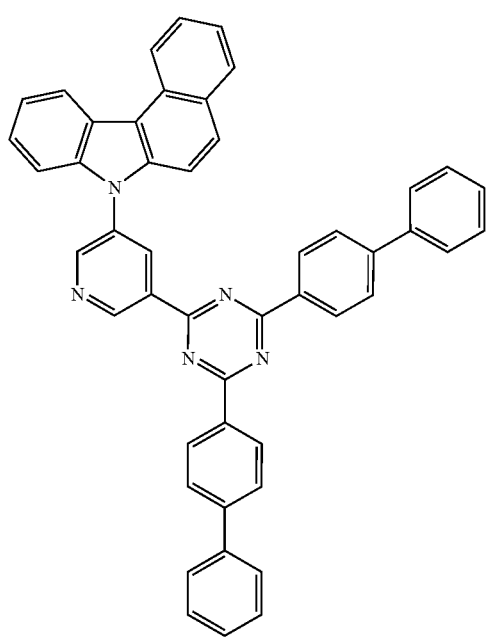
H2-44
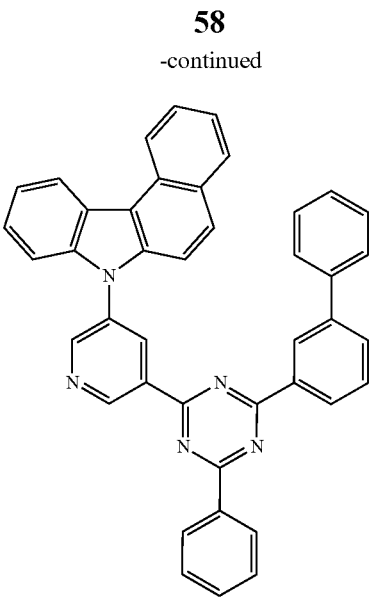
H2-45
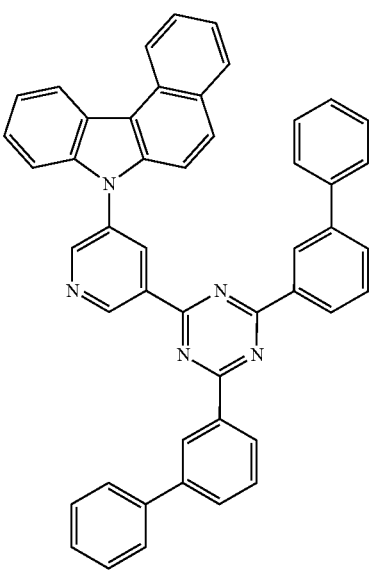
H2-46
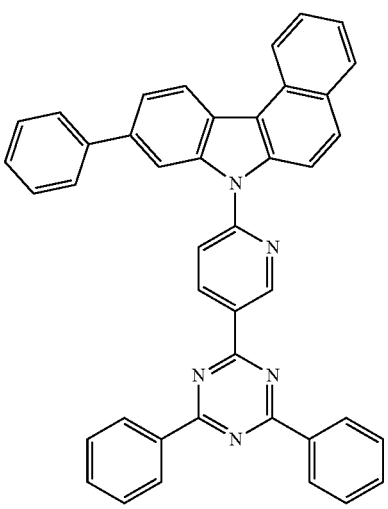

H2-47
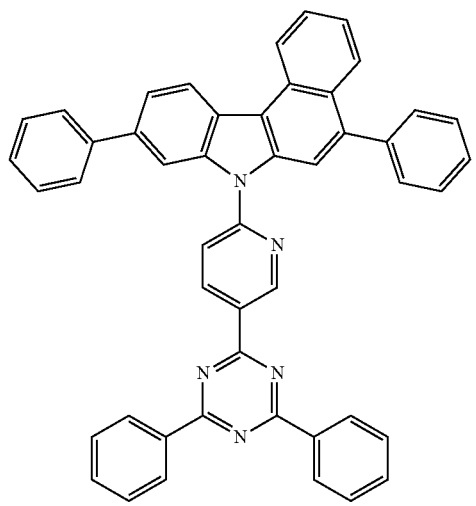
H2-48
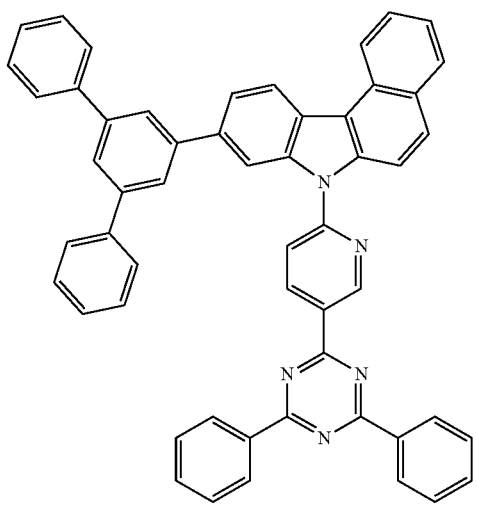
H2-49
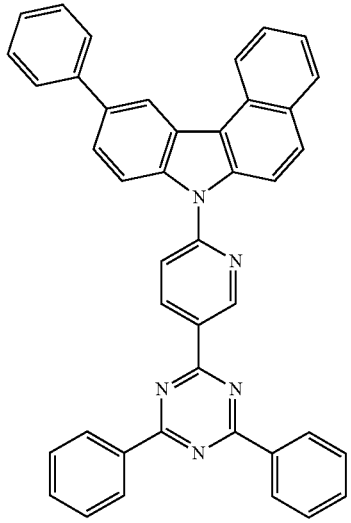
H2-50
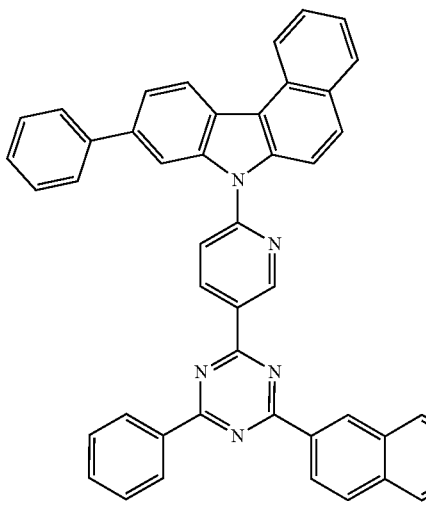
H2-51
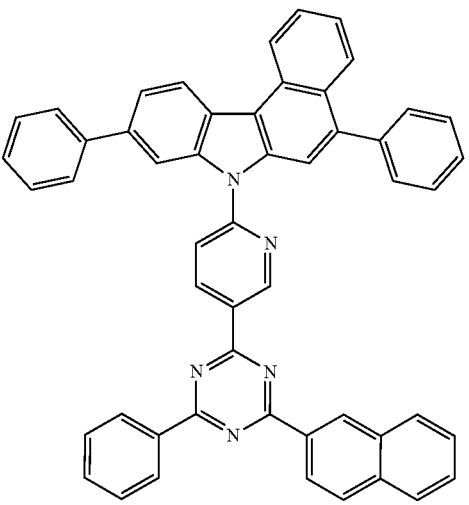
H2-52
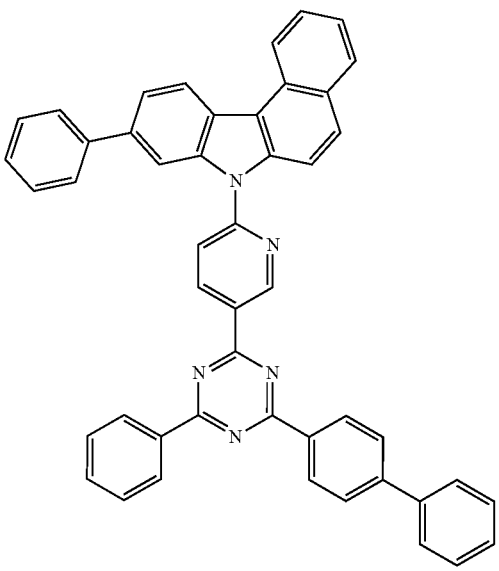

H2-53
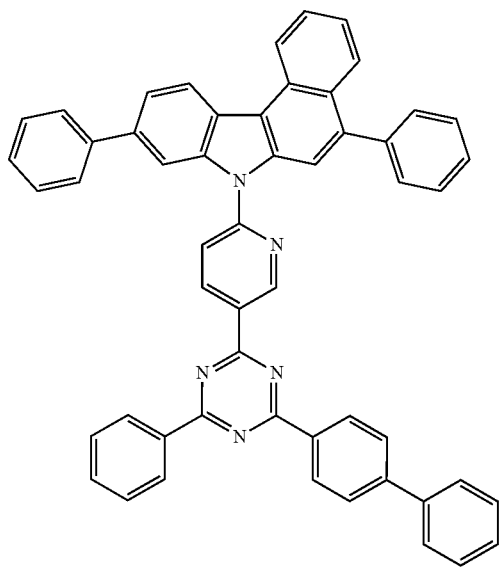
H2-54
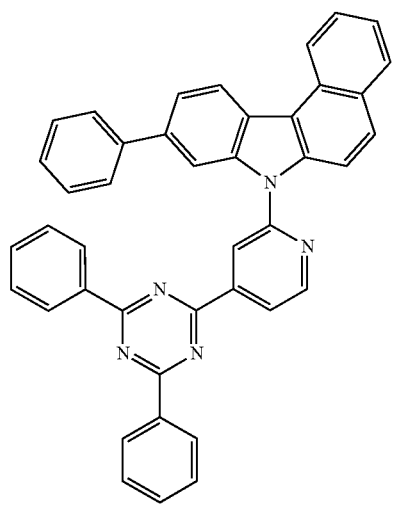
H2-55
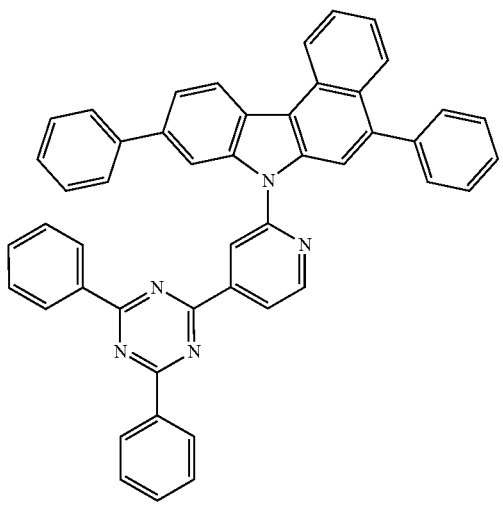
H2-56
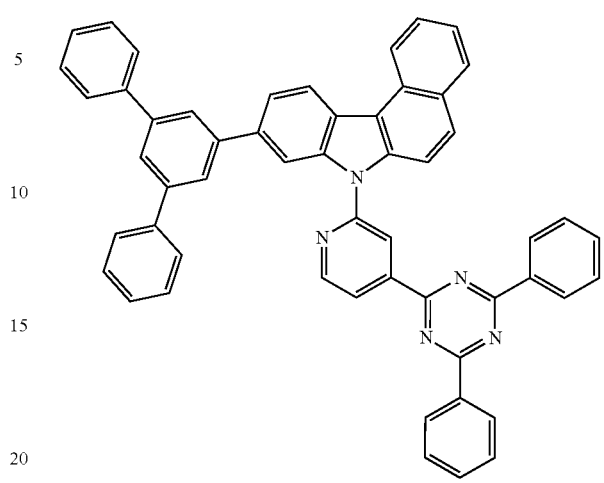
H2-57
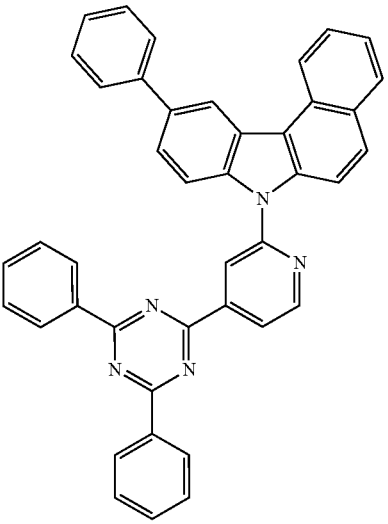
H2-58
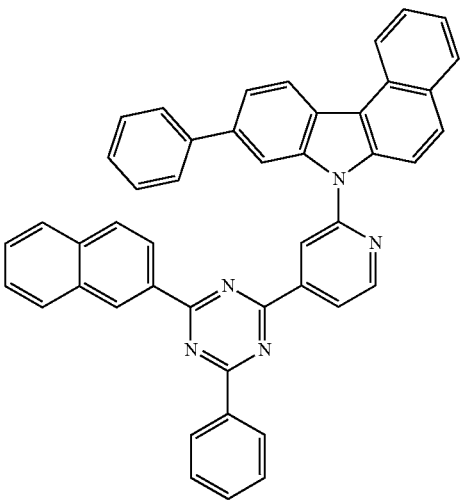

-continued
H2-59
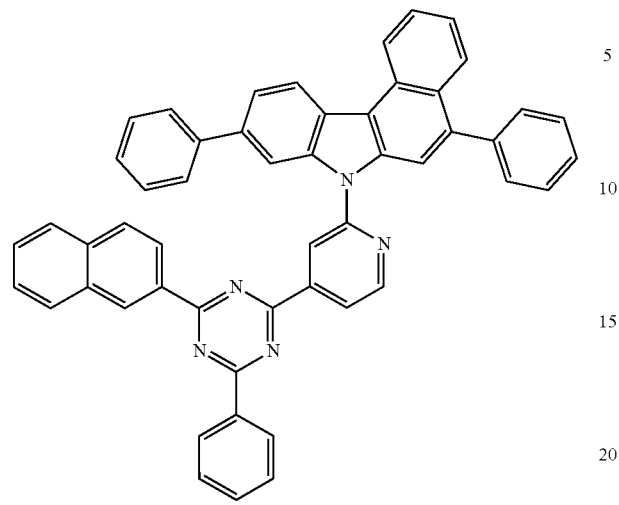
H2-62
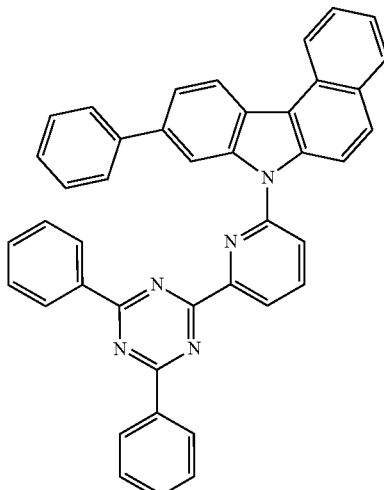
H2-60
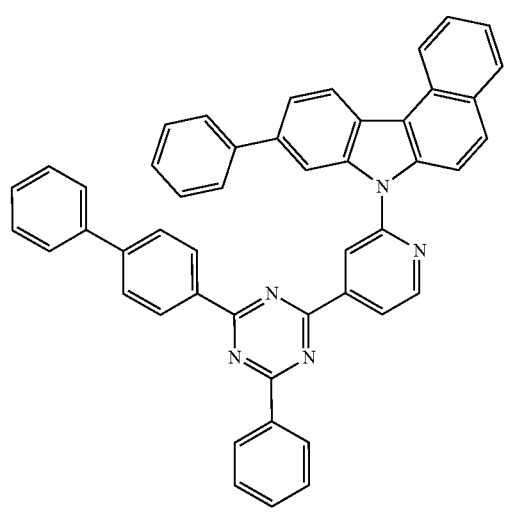
H2-63
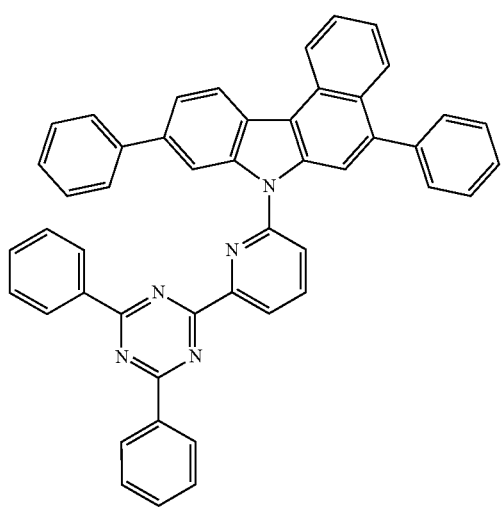
H2-61
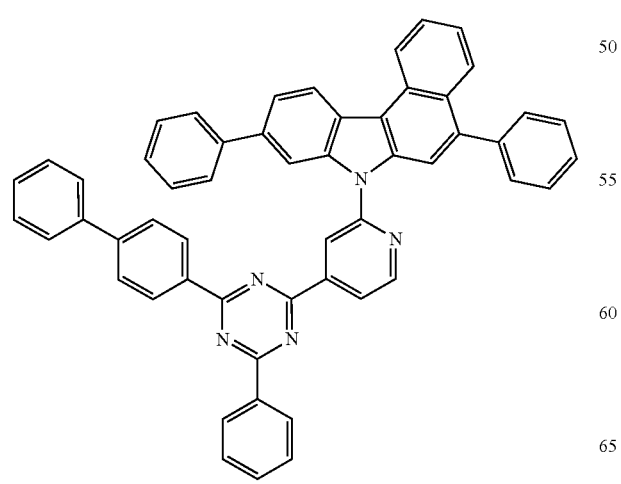
H2-64
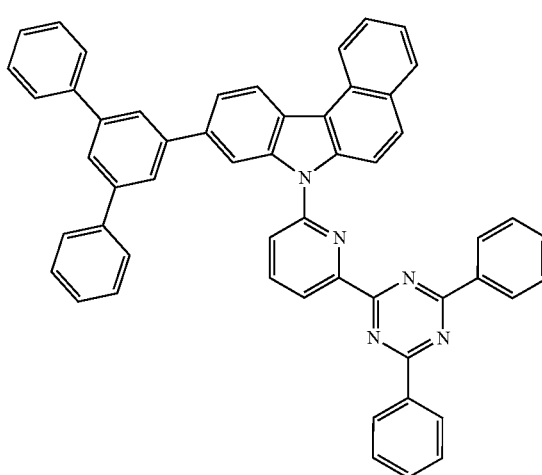

H2-65

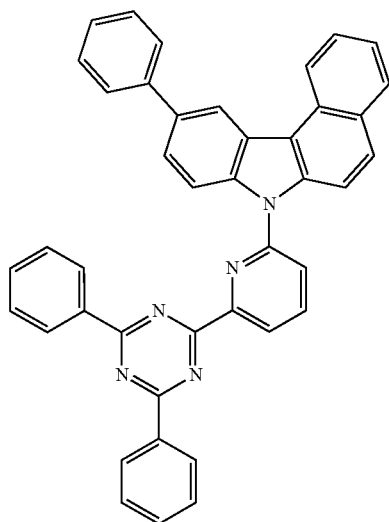

H2-68

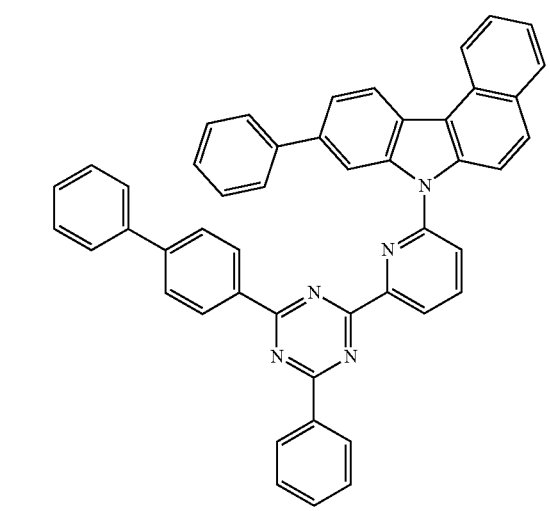

H2-66

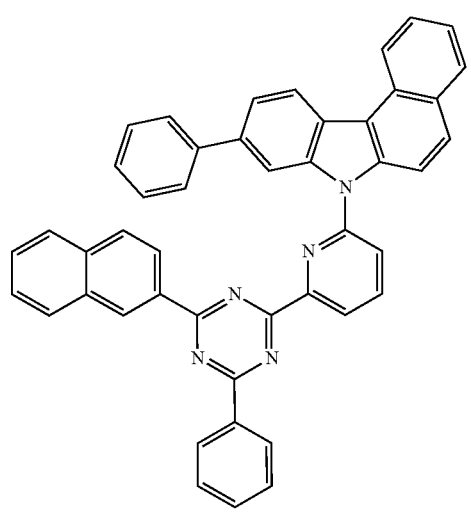

H2-69

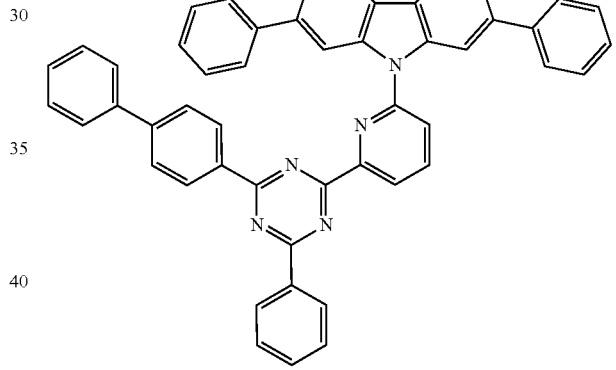

H2-67

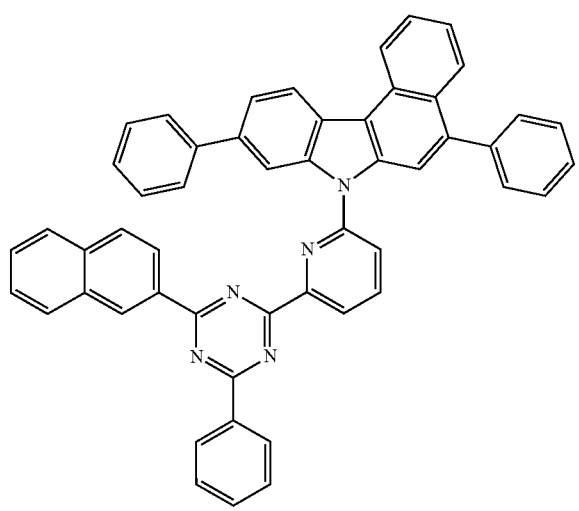

The compound of formula 1 and the compound of formula 2 of the present disclosure can be prepared by a synthetic method known to one skilled in the art, e.g., bromination, Suzuki reaction, Buchwald-Hartwig reaction, Ullmann reaction, etc.

According to another embodiment of the present disclosure, a combination comprising the compound of formula 1 and the compound of formula 2 is provided. The combination above may be a combination that is comprised in a light-emitting layer of an organic electroluminescent device.

In the combination of the present disclosure, the weight ratio in the light-emitting layer between the compound of formula 1 and the compound of formula 2 is in the range of 1:99 to 99:1, and preferably 30:70 to 70:30 in view of driving voltage, luminous efficiency, and lifespan.

The organic electroluminescent device of the present disclosure comprises an anode, a cathode, and one or more light-emitting layers disposed between the anode and cathode, wherein the light-emitting layers comprise a dopant and a host; the host comprises two or more host compounds; and a first host compound of the host compounds is represented by the formula 1 above; and a second host compound is represented by formula 2 above.

The light-emitting layer indicates a layer or plural layers consisting of two or more stacked layers, from which light is emitted. It is preferable that a doping amount of the dopant compound is less than 20 wt % based on the total amount of the host compound and the dopant compound. In the organic electroluminescent device of the present disclosure, the weight ratio in the light-emitting layer between the first host material and the second host material is in the range of 1:99 to 99:1, and preferably 30:70 to 70:30 in view of driving voltage, luminous efficiency, and lifespan.

The dopant for the organic electroluminescent device of the present disclosure is preferably one or more phosphorescent dopant compounds. The phosphorescent dopant compound for the organic electroluminescent device of the present disclosure is not limited, but may be preferably selected from metallated complex compounds of iridium (Ir), osmium (Os), copper (Cu) or platinum (Pt), more preferably selected from ortho-metallated complex compounds of iridium (Ir), osmium (Os), copper (Cu) or platinum (Pt), and even more preferably ortho-metallated iridium complex compounds.

The phosphorescent dopant may be preferably selected from the compound of the following formulae 101 to 103:

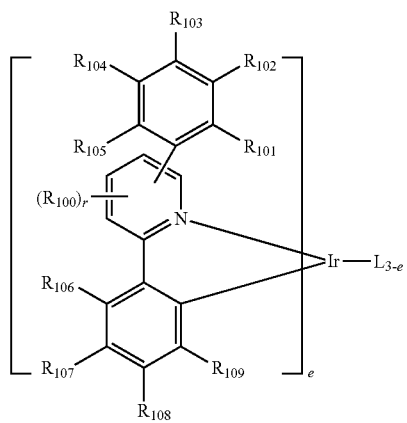

(101)

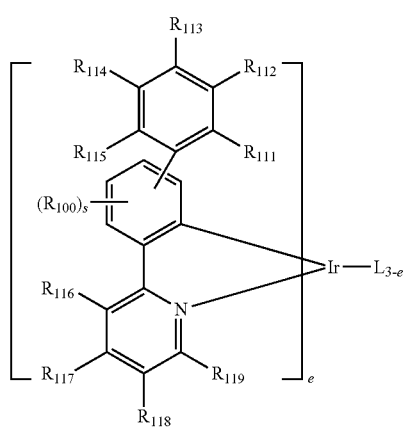

(102)

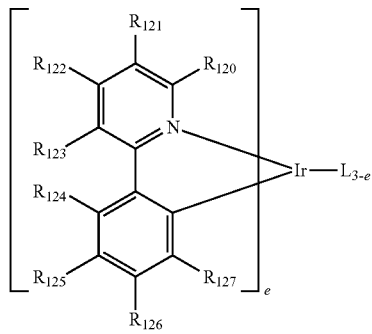

(103)

wherein L is selected from the following structures:

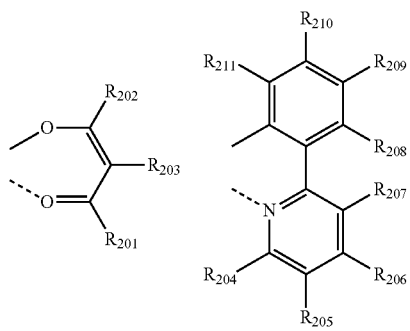

$R_{100}$ represents hydrogen, or a substituted or unsubstituted (C1-C30)alkyl; $R_{101}$ to $R_{109}$ and $R_{111}$ to $R_{123}$, each independently, represent hydrogen, deuterium, a halogen, a (C1-C30)alkyl substituted or unsubstituted with a halogen, a cyano, a substituted or unsubstituted (C1-C30)alkoxy, a substituted or unsubstituted (C3-C30)cycloalkyl, or a substituted or unsubstituted (C6-C30)aryl; $R_{120}$ to $R_{123}$, each independently, may be linked to an adjacent substituent(s) to form a substituted or unsubstituted 3 to 30-membered, mono- or polycyclic, alicyclic or aromatic ring, or a combination of the alicyclic ring and the aromatic ring, for example, a quinoline; $R_{124}$ to $R_{127}$, each independently, represent hydrogen, deuterium, a halogen, a substituted or unsubstituted (C1-C30)alkyl, or a substituted or unsubstituted (C6-C30)aryl; when $R_{124}$ to $R_{127}$, each independently, are an aryl, $R_{124}$ to $R_{127}$, each independently, may be linked to an adjacent substituent(s) to form a substituted or unsubstituted 3 to 30-membered, mono- or polycyclic, alicyclic or (hetero)aromatic ring, or a combination of the alicyclic ring and the (hetero)aromatic ring, for example, a fluorene, a dibenzothiophene, a dibenzofuran; $R_{201}$ to $R_{211}$, each independently, represent hydrogen, deuterium, a halogen, or a (C1-C30) alkyl substituted or unsubstituted with a halogen; $R_{208}$ to $R_{211}$, each independently, may be linked to an adjacent substituent(s) to form a substituted or unsubstituted 3 to 30-membered, mono- or polycyclic, alicyclic, aromatic, or heteroaromatic ring, or a combination of the alicyclic ring, the aromatic ring, and the heteroaromatic ring, for example, a fluorene, a dibenzothiophene, a dibenzofuran; r and s, each independently, represent an integer of 1 to 3; when r or s is an integer of 2 or more, each of $R_{100}$ may be the same or different; and e represents an integer of 1 to 3.

Specifically, the phosphorescent dopant includes the following:
D-1
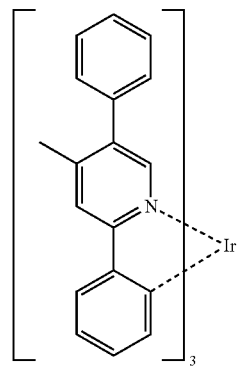
D-2
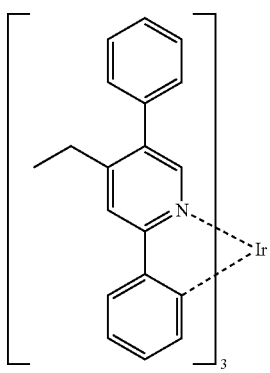
D-3
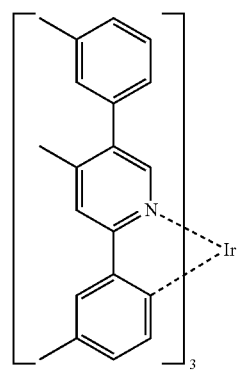
D-4
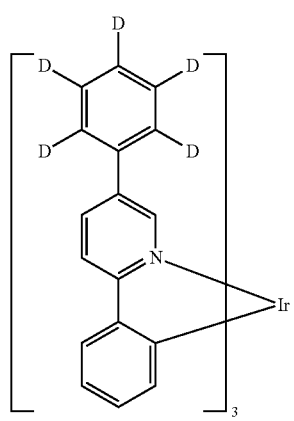
-continued
D-5
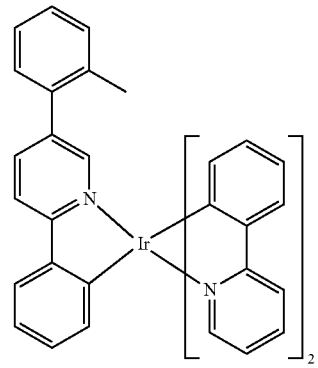
D-6
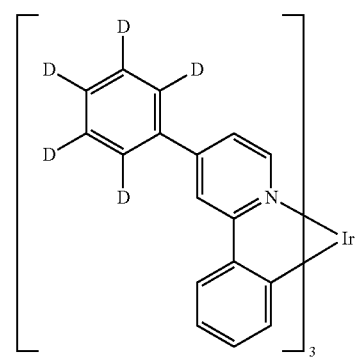
D-7
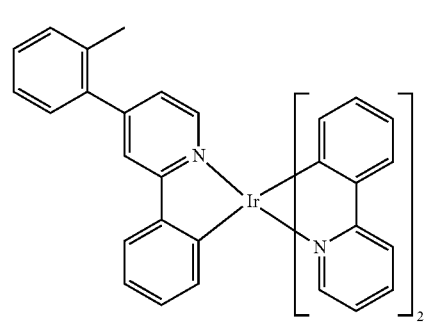
D-8
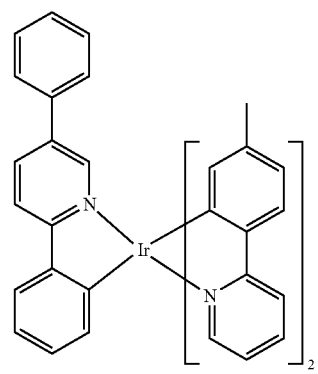

D-9
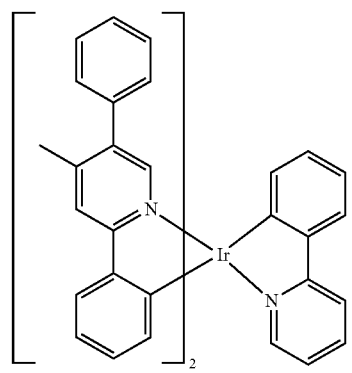
D-10
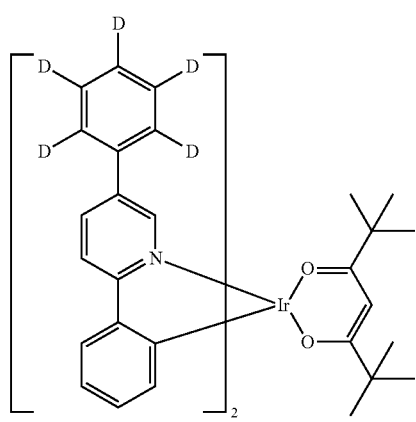
D-11
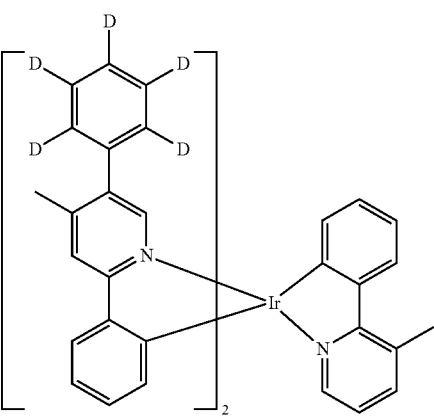
D-12
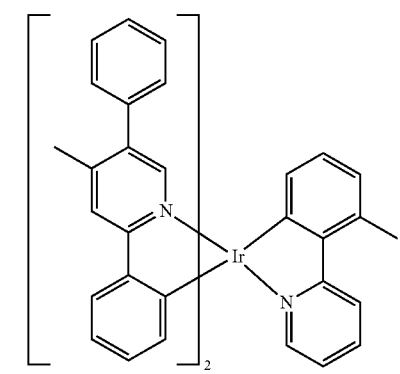
D-13
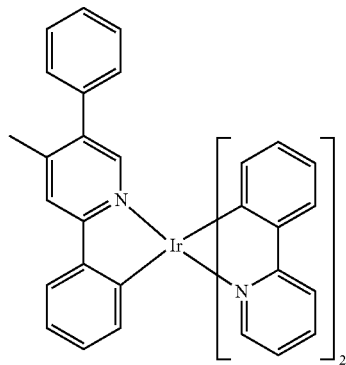
D-14
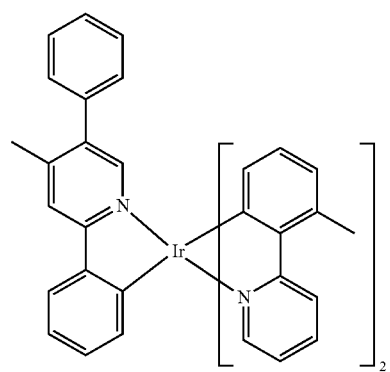
D-15
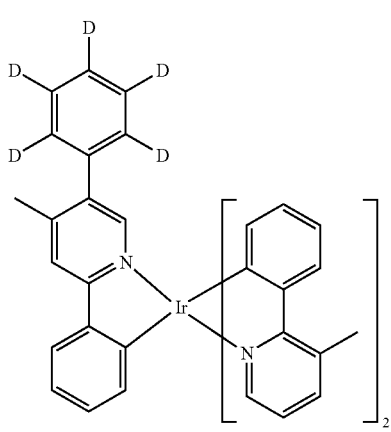
D-16
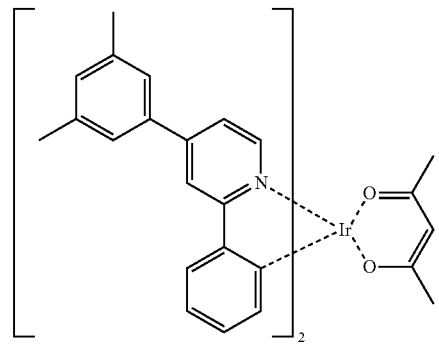

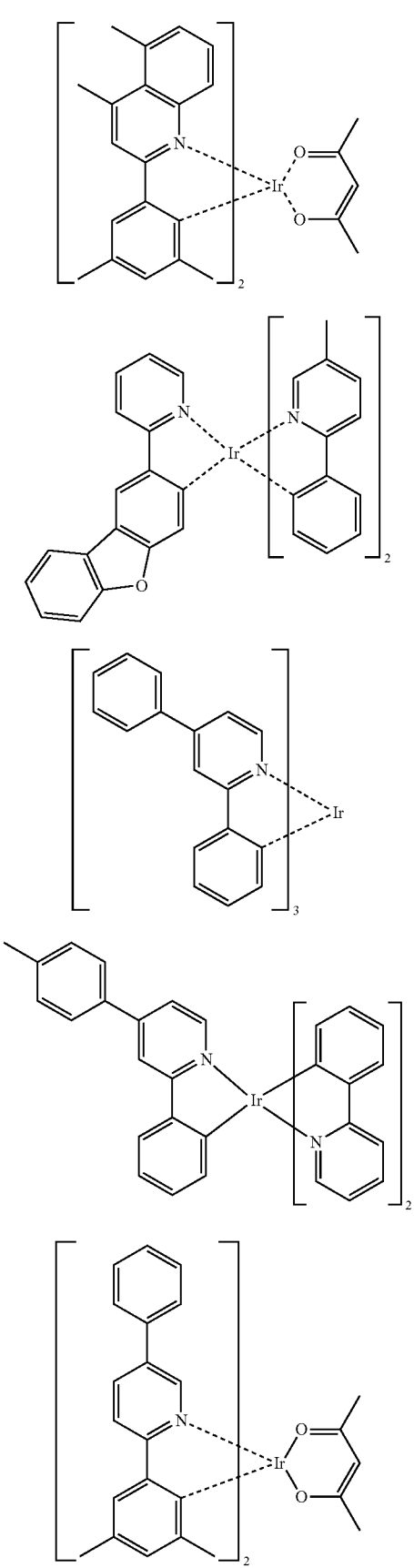
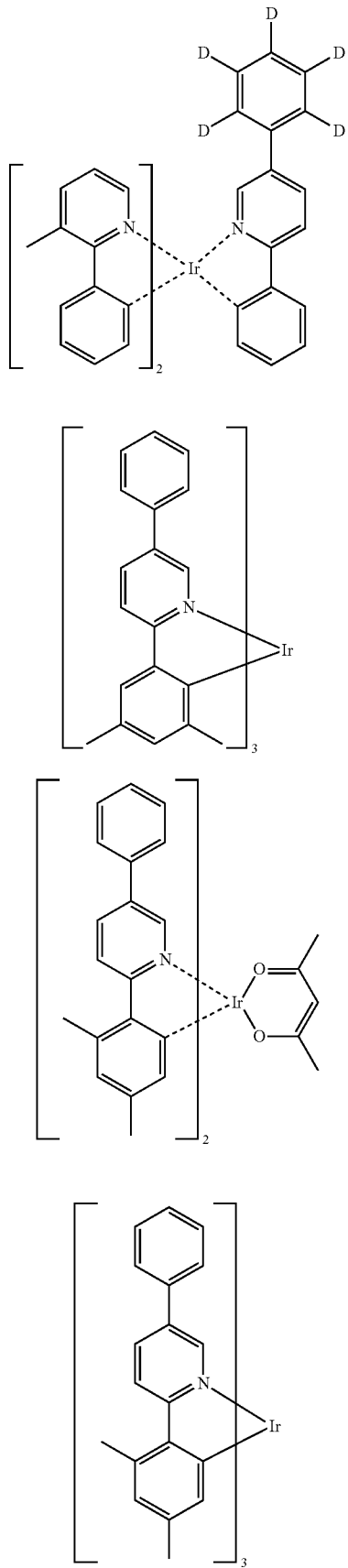

-continued
D-26
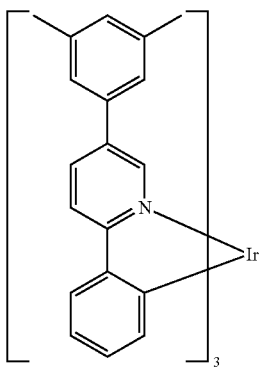
D-27
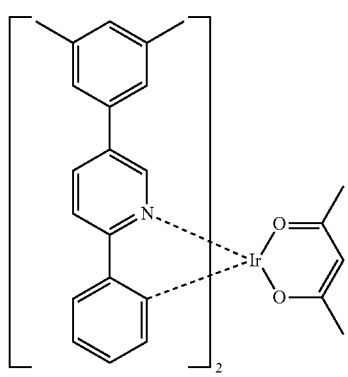
D-28
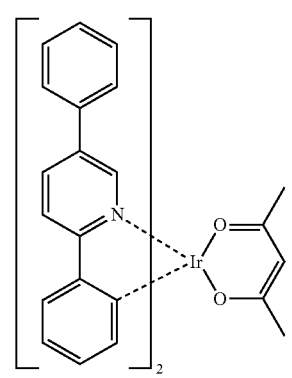
D-29
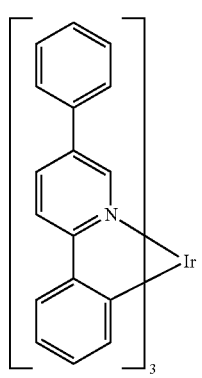
-continued
D-30
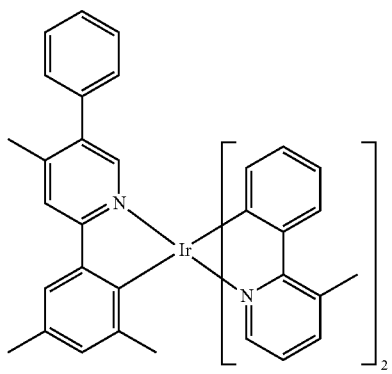
D-31
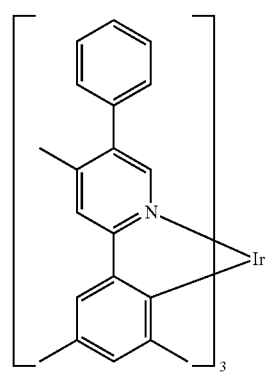
D-32
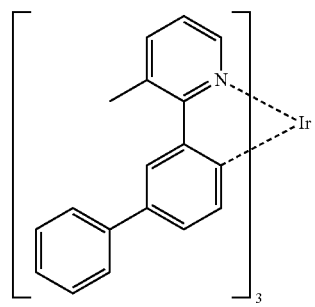
D-33
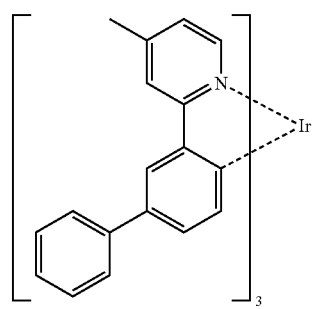

D-34 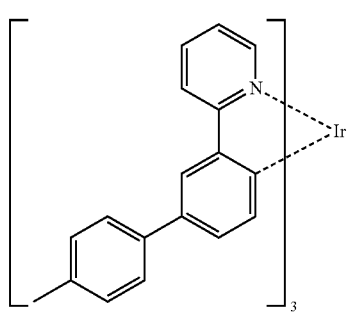
D-35 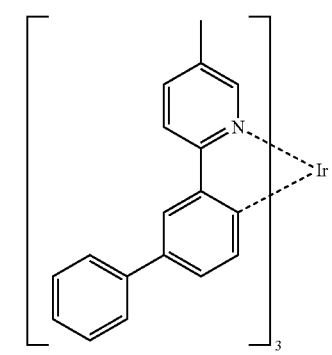
D-36 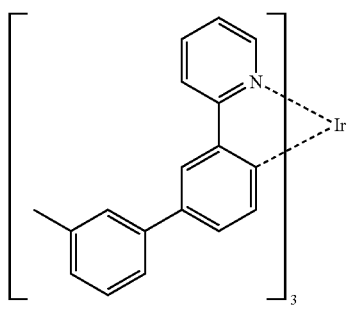
D-37 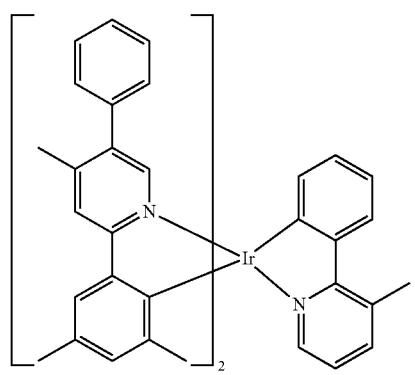
D-38 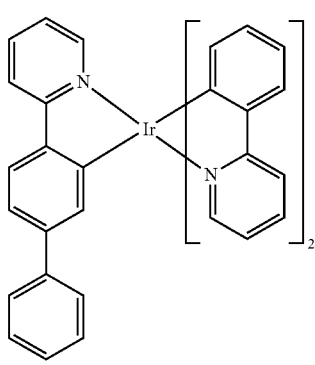
D-39 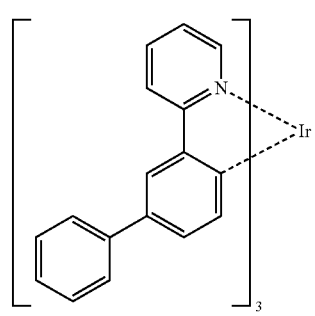
D-40 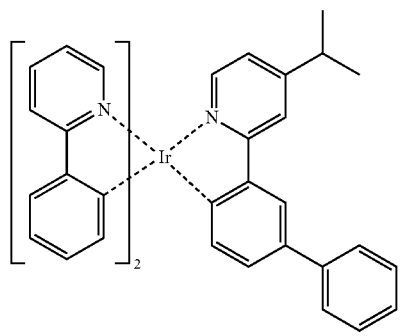
D-41 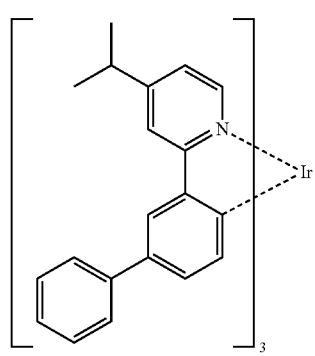

-continued
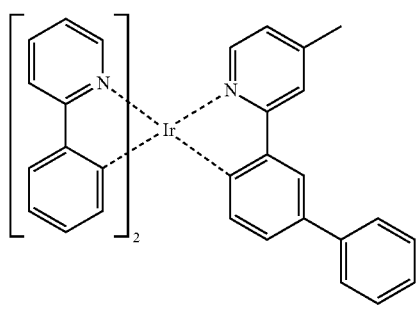
D-42
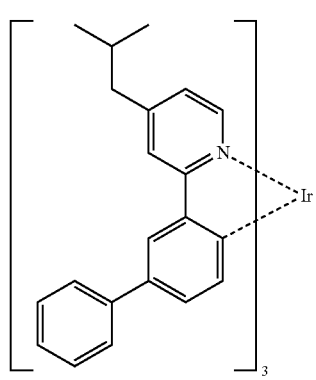
D-43
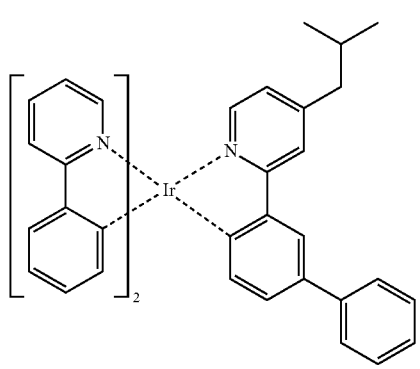
D-44
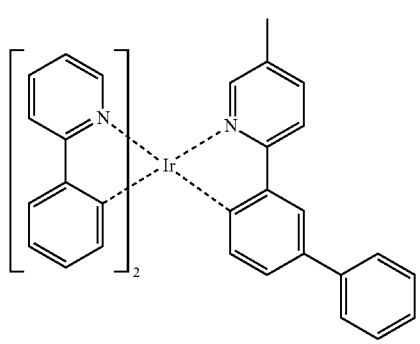
D-45
-continued
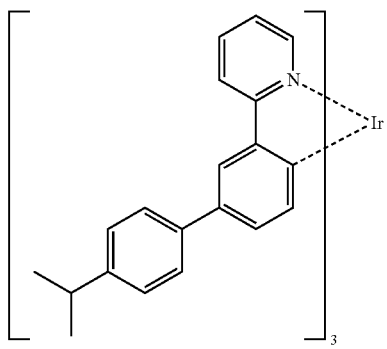
D-46
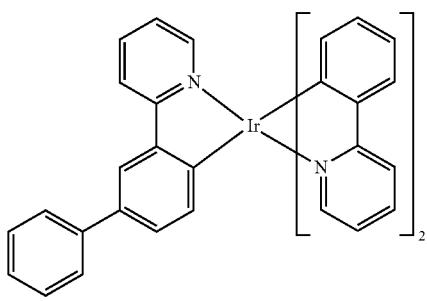
D-47
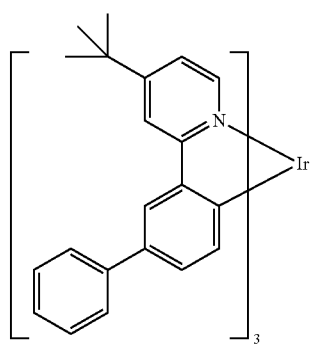
D-48
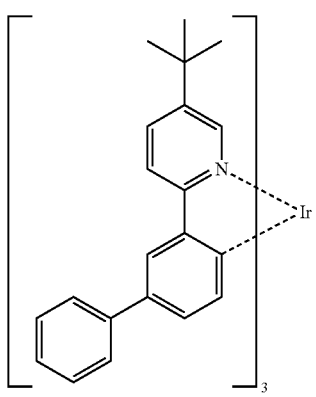
D-49

D-50 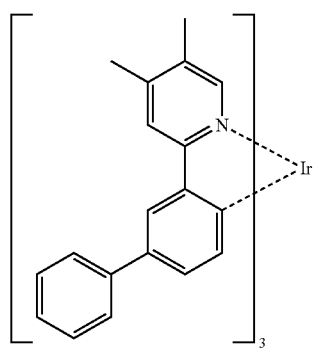
D-54 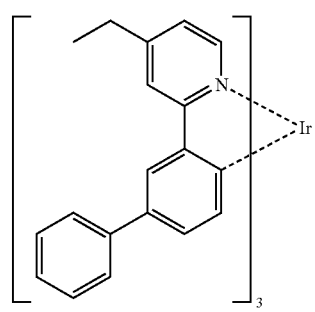
D-51 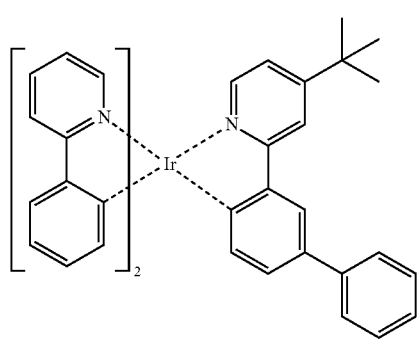
D-55 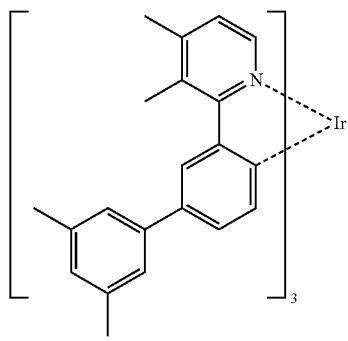
D-52 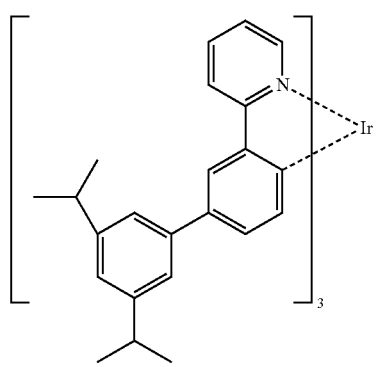
D-56 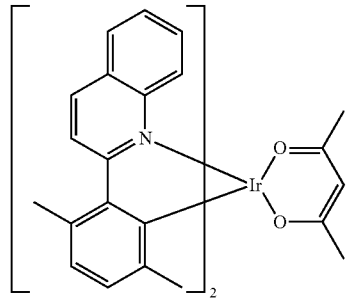
D-53 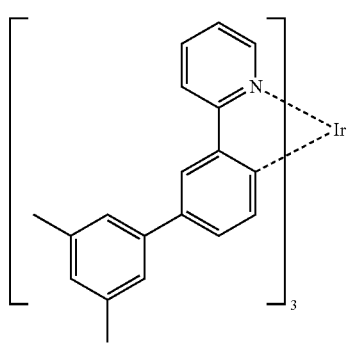
D-57 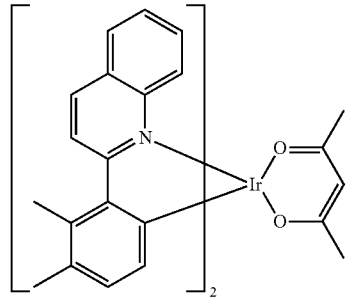

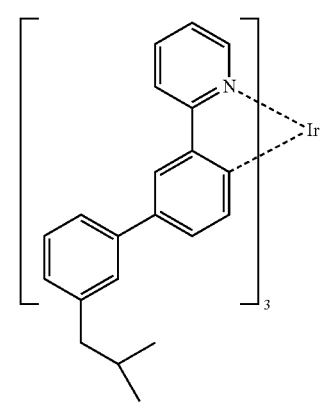
D-58
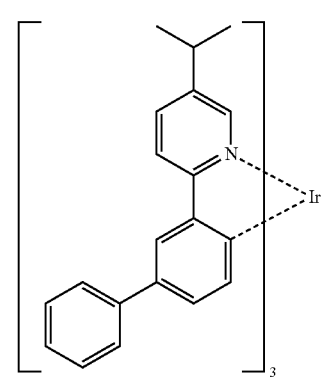
D-59
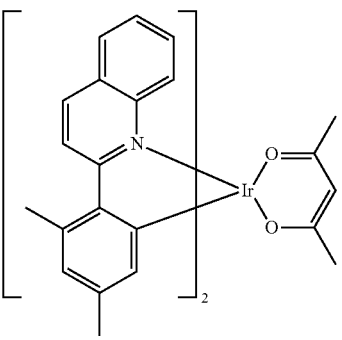
D-60
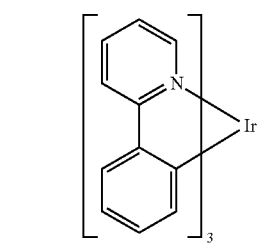
D-61
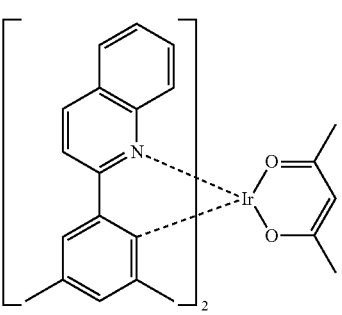
D-62
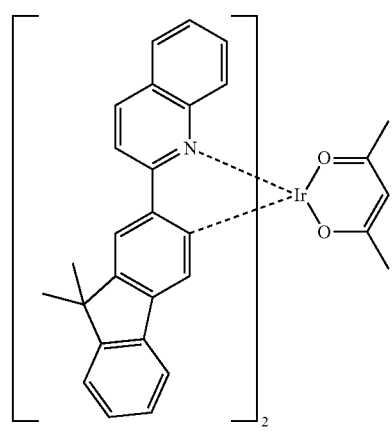
D-63
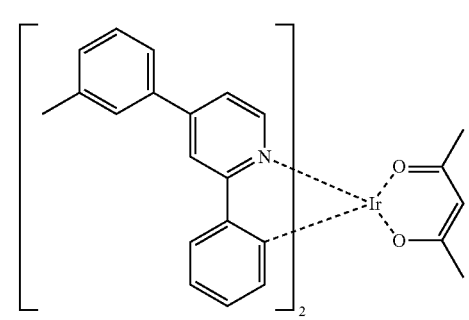
D-64
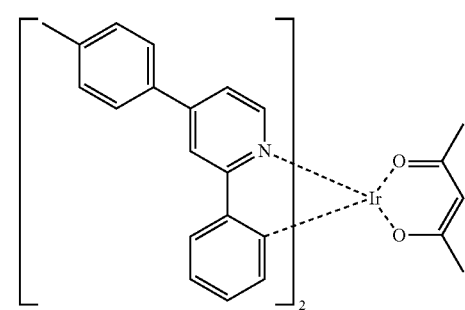
D-65
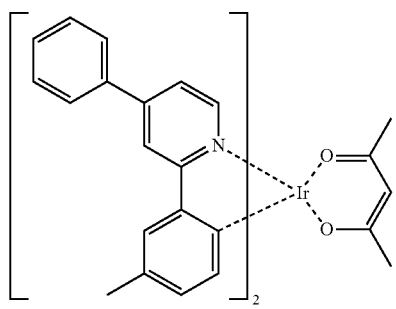
D-66

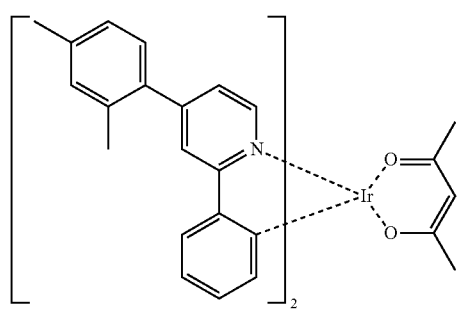
D-67
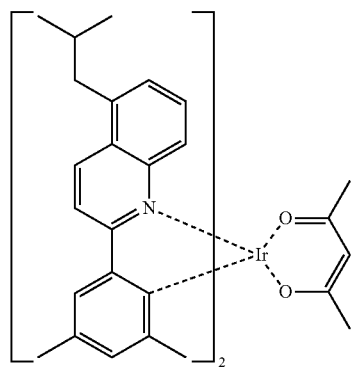
D-71
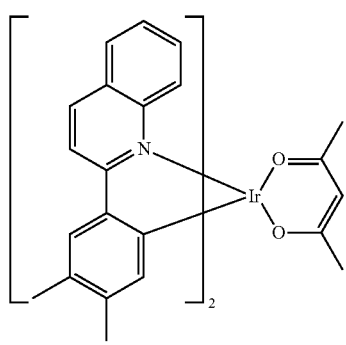
D-68
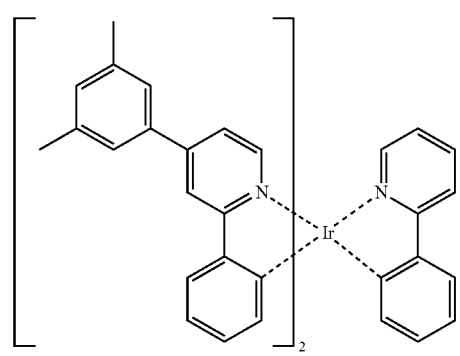
D-72
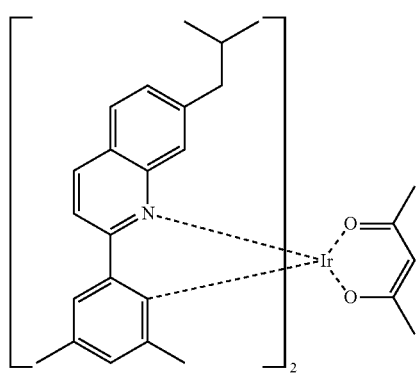
D-69
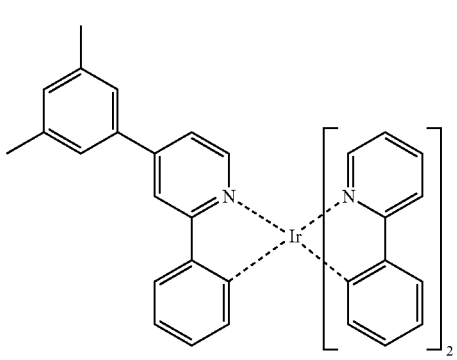
D-73
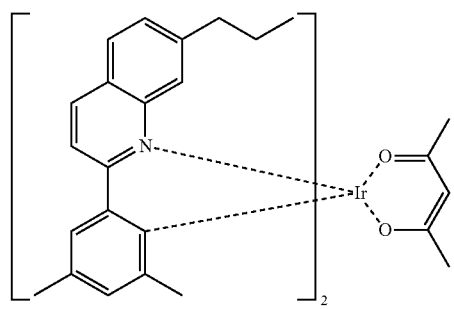
D-70
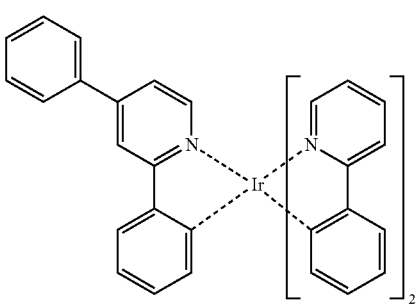
D-74

-continued
D-75
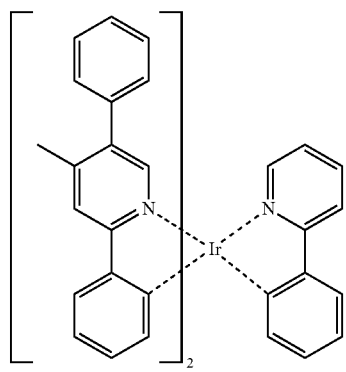
D-76
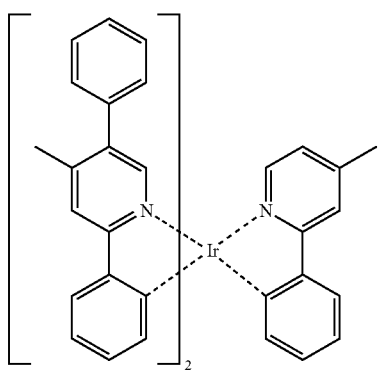
D-77
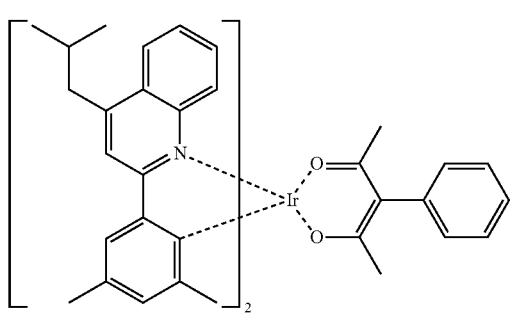
D-78
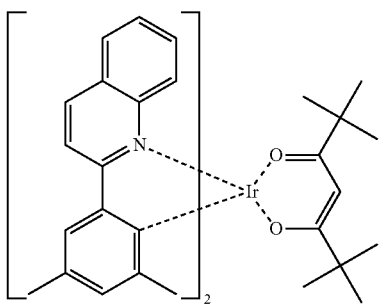
-continued
D-79
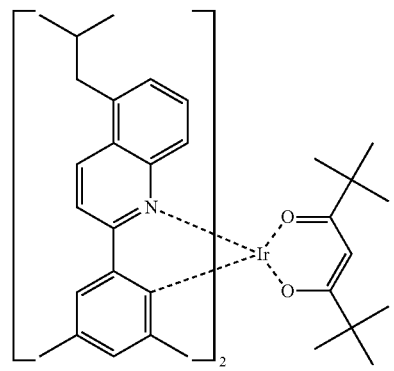
D-80
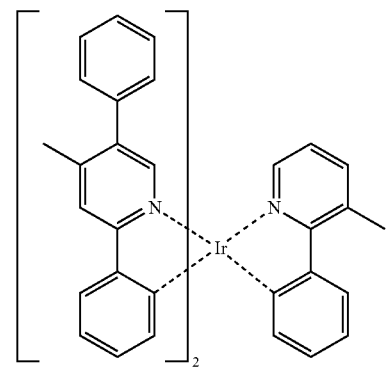
D-81
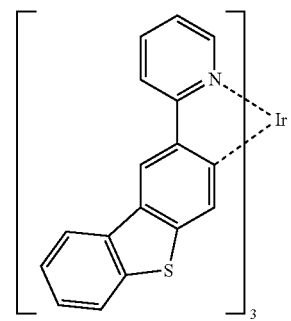
D-82
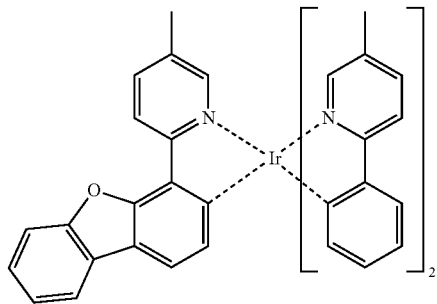

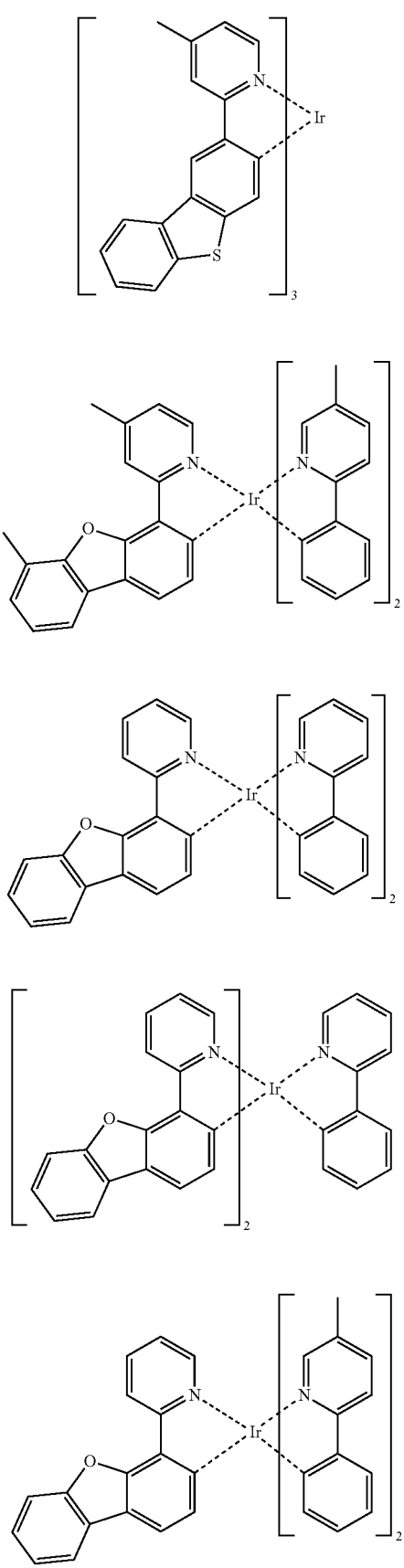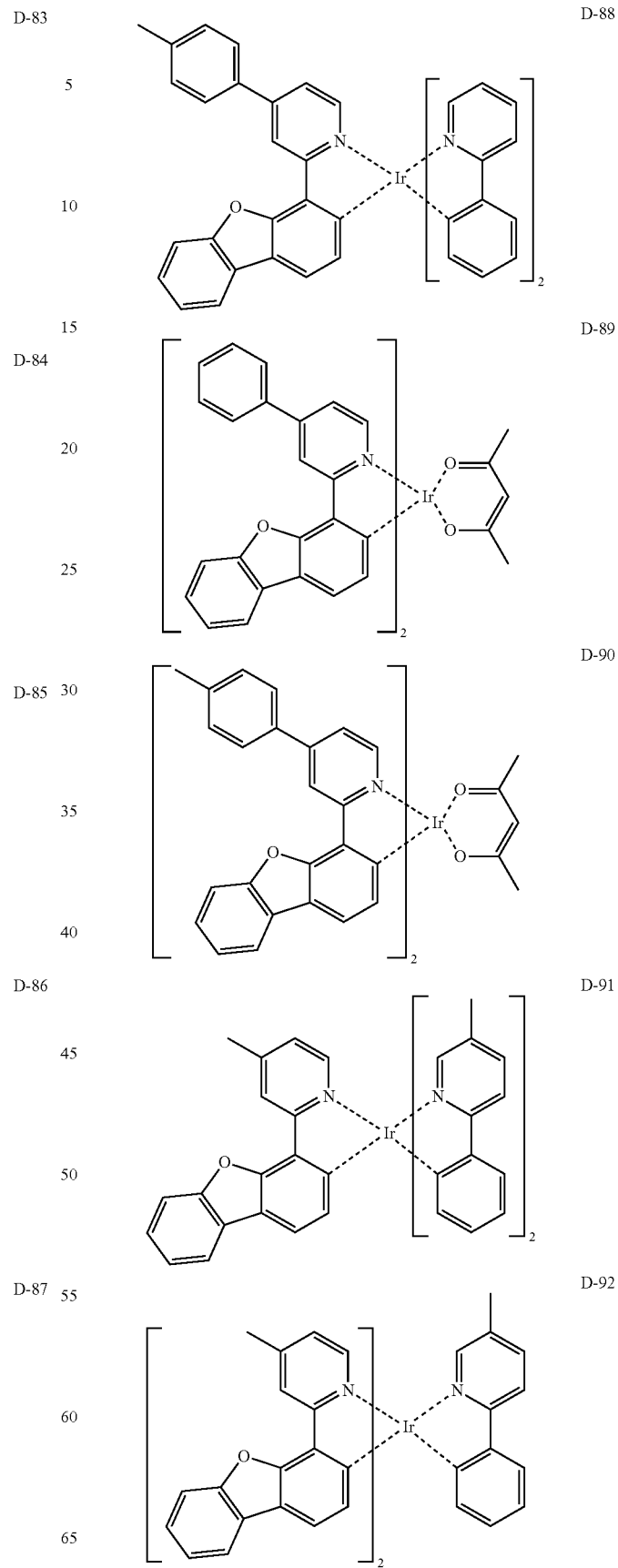

D-93
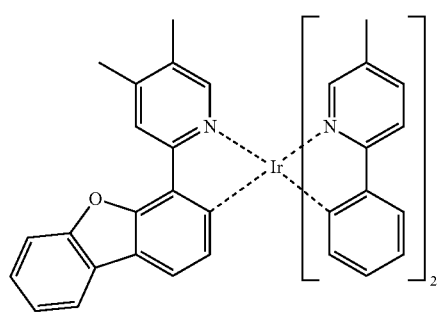
D-94
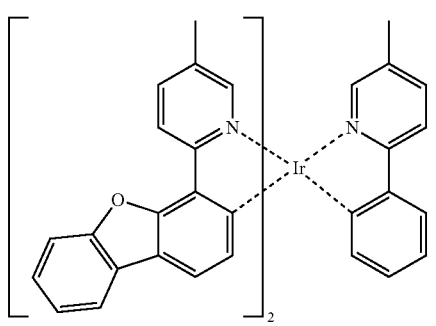
D-95
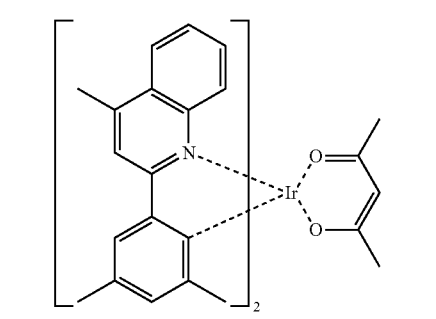
D-96
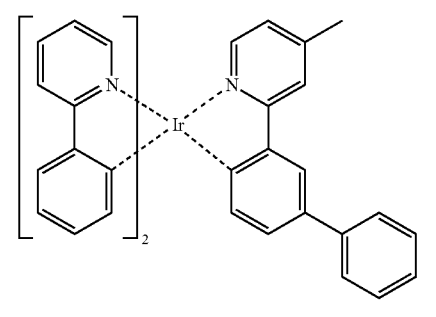
D-97
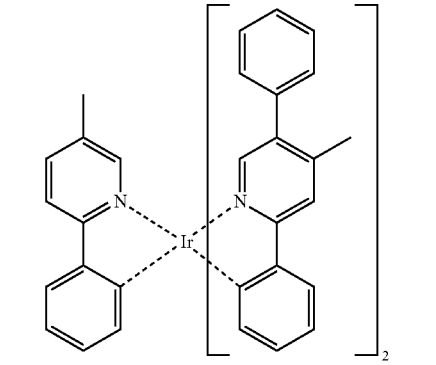
D-98
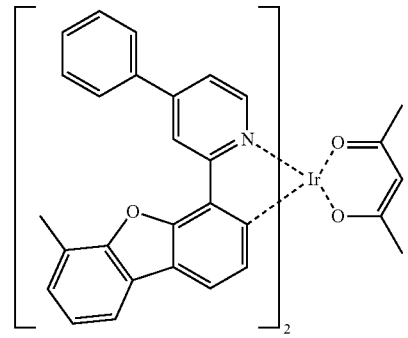
D-99
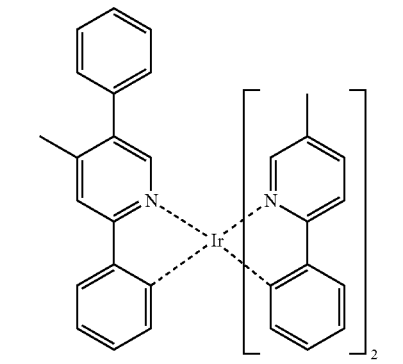
D-100
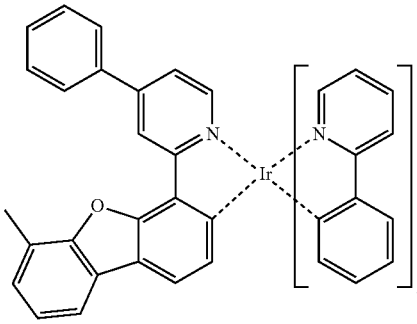
D-101
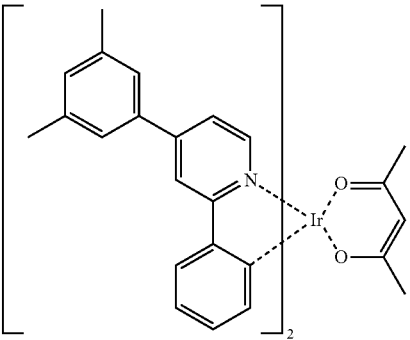
D-102
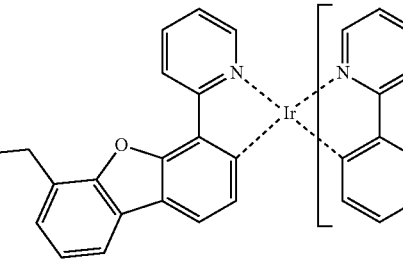

D-103
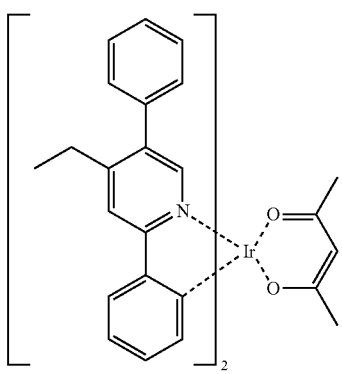
D-107
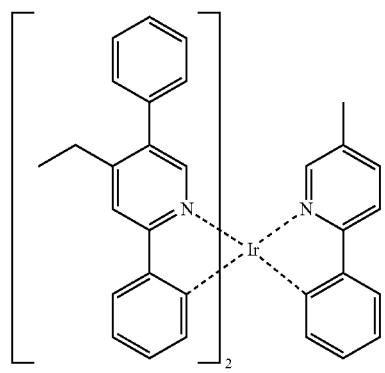
D-104
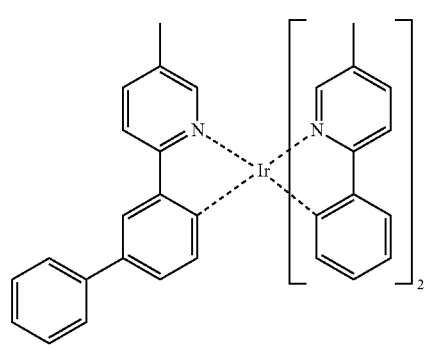
D-108
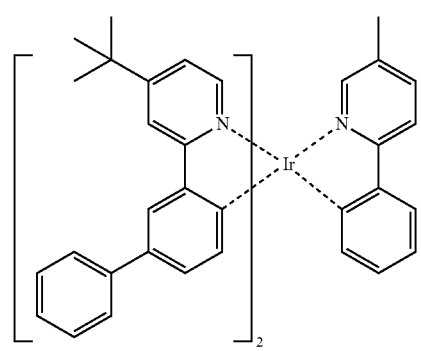
D-105
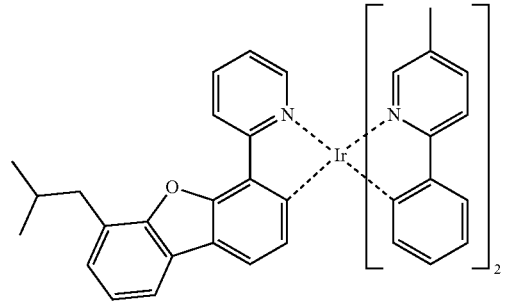
D-109
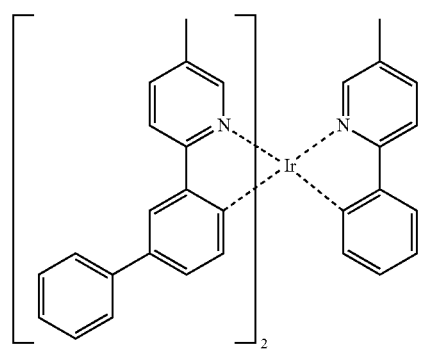
D-106
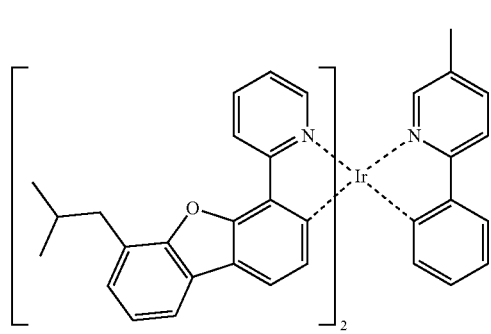
D-110
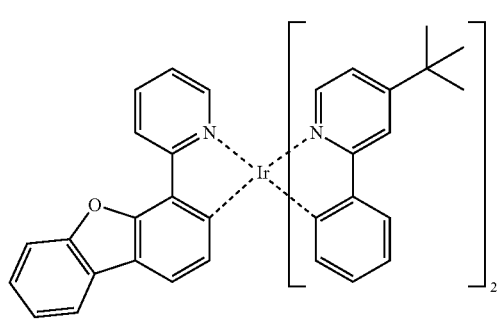

D-111
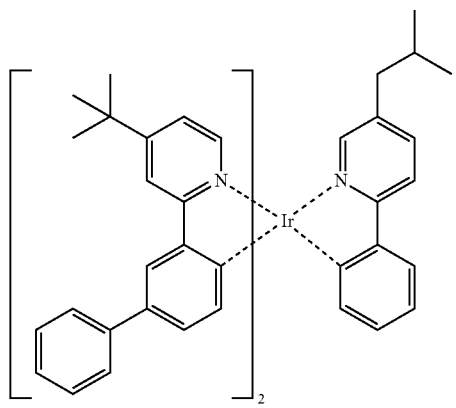
D-115
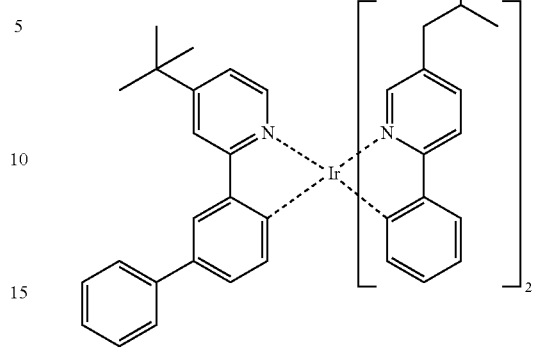
D-112
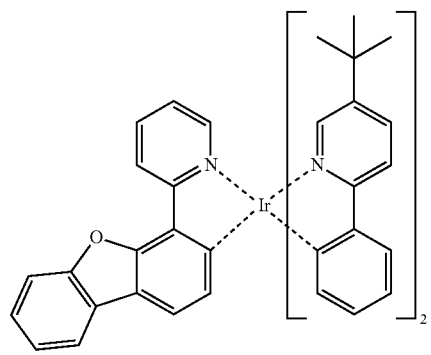
D-116
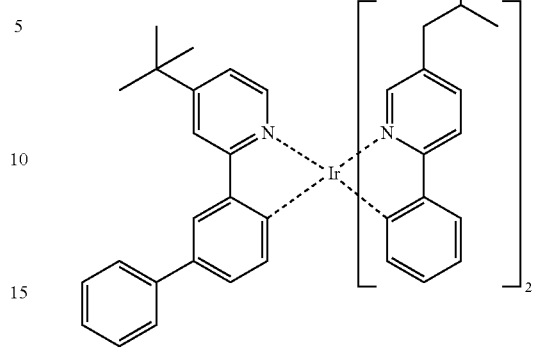
D-113
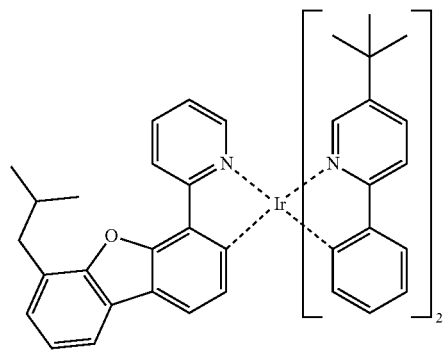
D-117
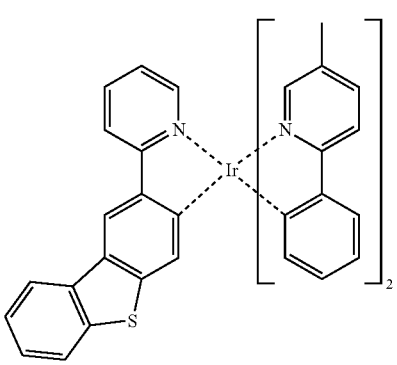
D-114
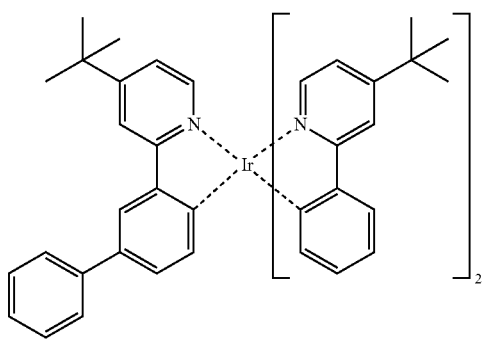
D-118
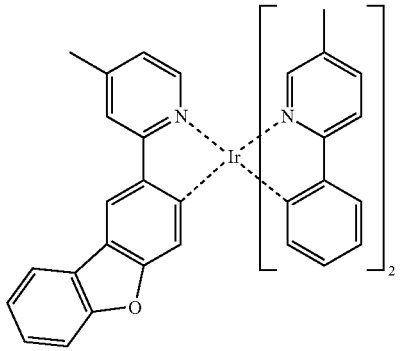

-continued
D-119
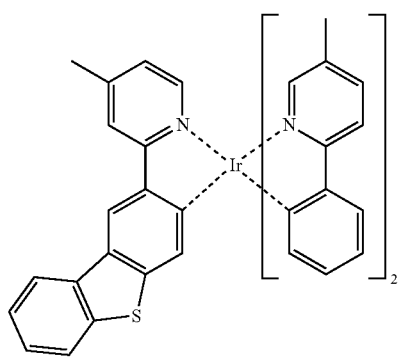
D-120
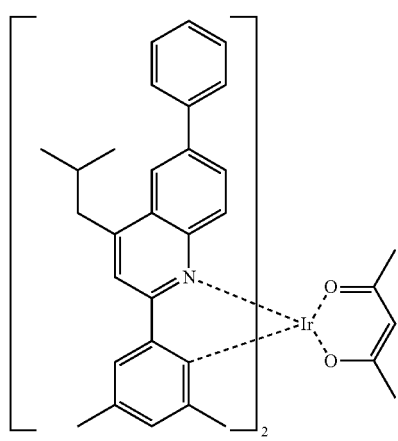
D-121
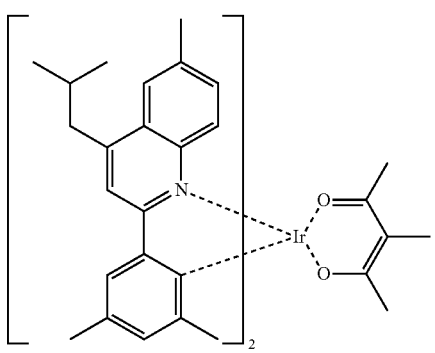
D-122
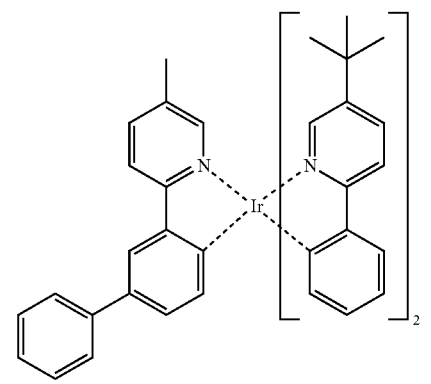
-continued
D-123
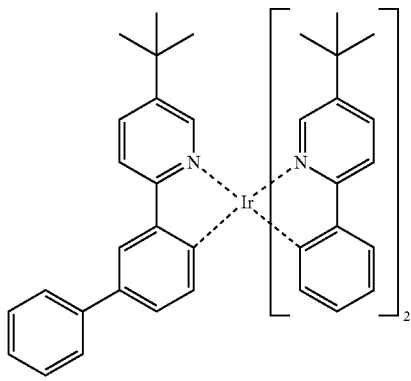
D-124
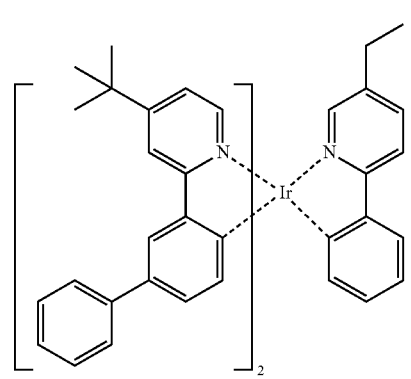
D-125
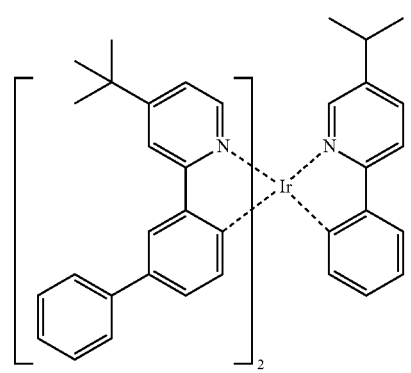
D-126
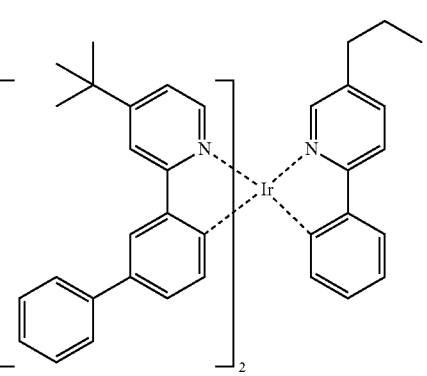

-continued
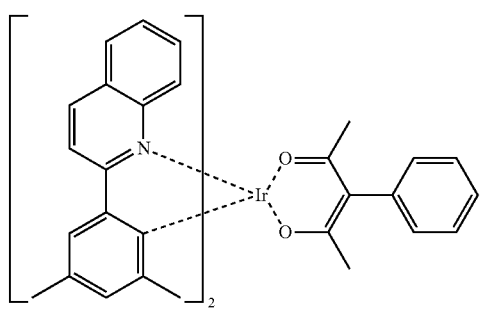
D-127
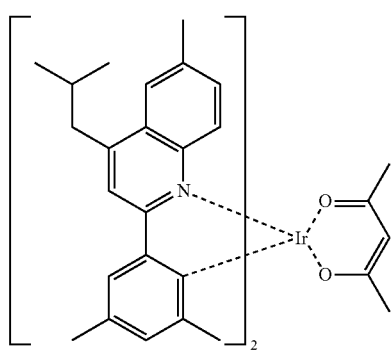
D-128
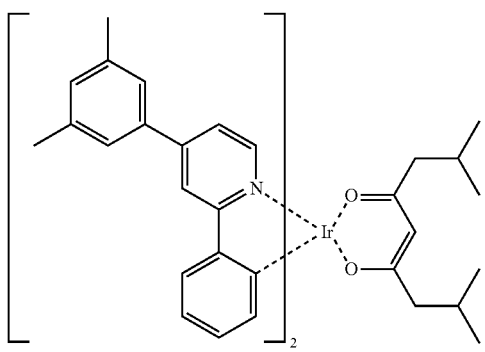
D-129
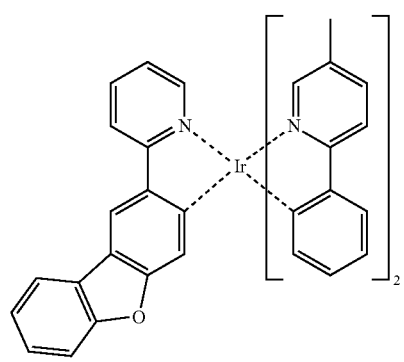
D-130
-continued
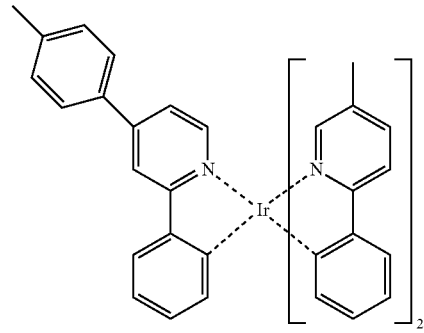
D-131
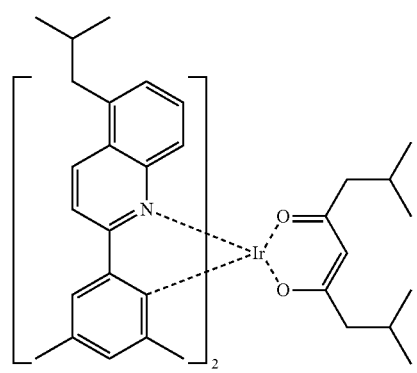
D-132
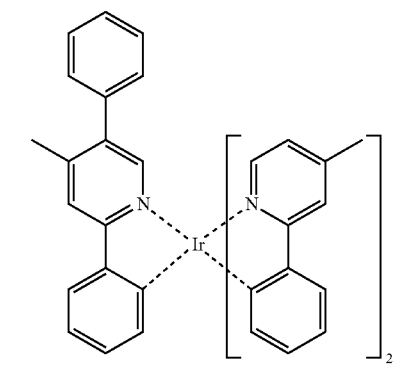
D-133
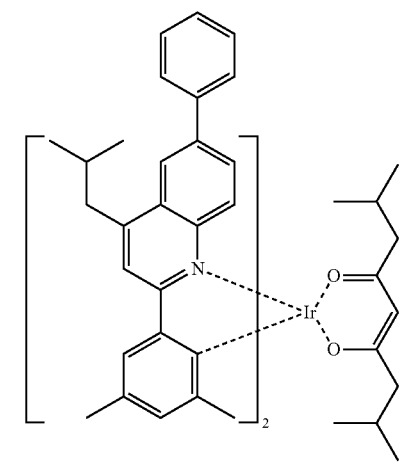
D-134

D-135
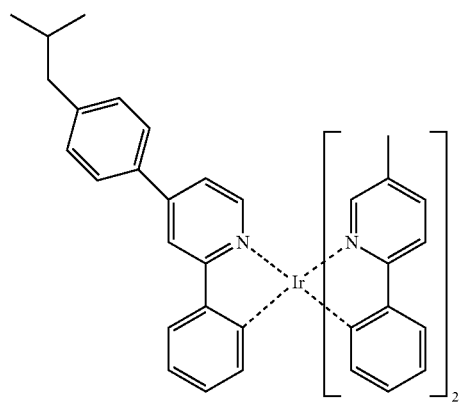
D-136
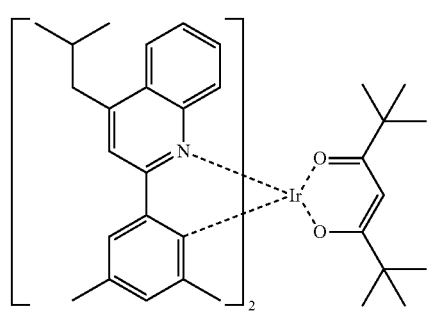
D-137
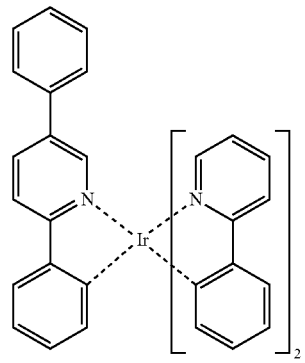
D-138
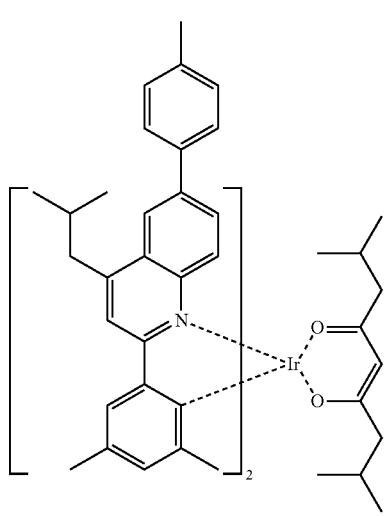
D-139
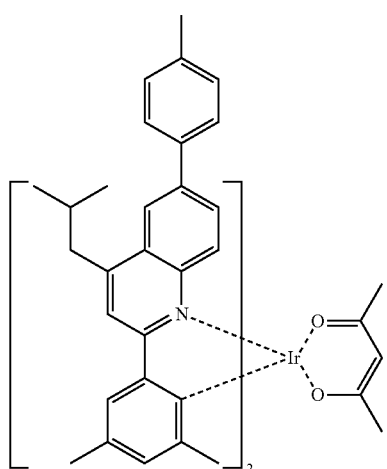
D-140
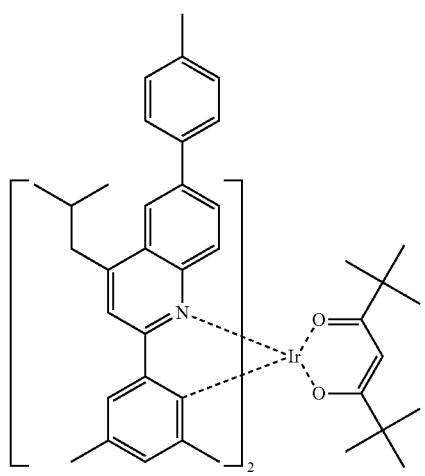
D-141
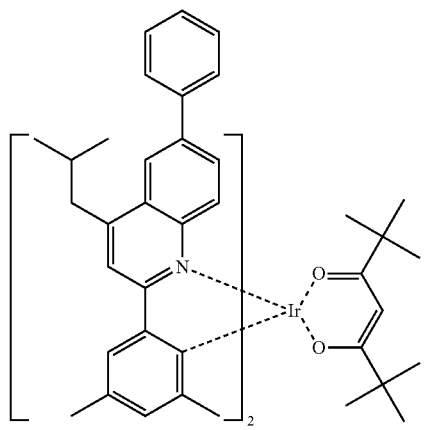

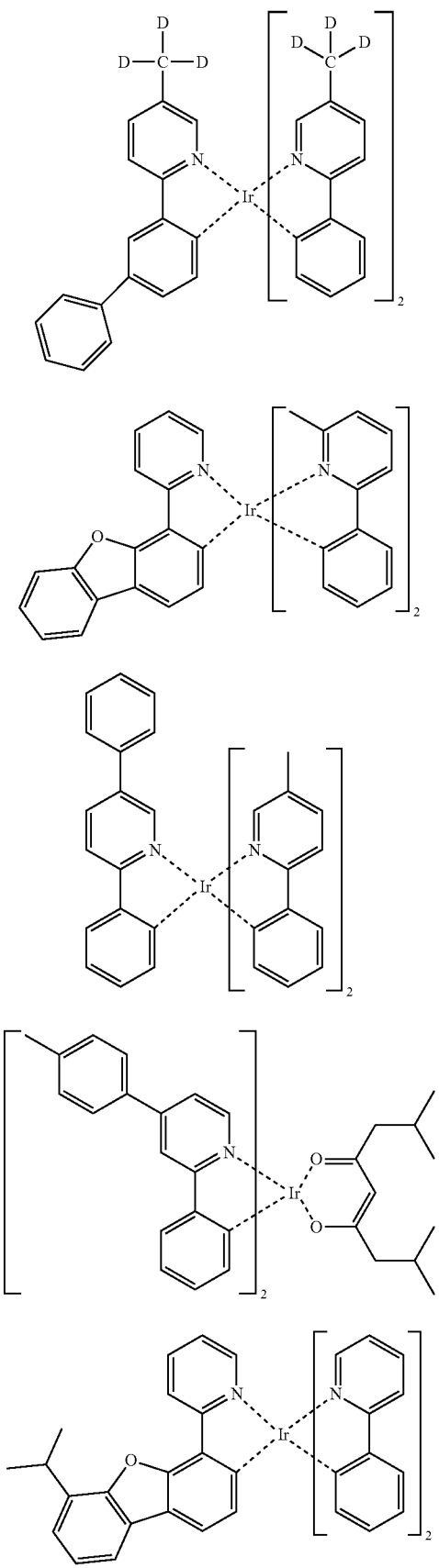

The organic electroluminescent device of the present disclosure may further comprise at least one compound selected from the group consisting of arylamine-based compounds and styrylarylamine-based compounds in the organic layer.

In the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of the d-transition elements of the Periodic Table, or at least one complex compound comprising the metal.

In the organic electroluminescent device of the present disclosure, preferably, at least one layer (hereinafter, "a surface layer") may be placed on an inner surface(s) of one or both electrode(s), selected from a chalcogenide layer, a metal halide layer and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a hole injection layer, a hole transport layer, a hole auxiliary layer, an auxiliary light-emitting layer, or an electron blocking layer, or a combination thereof may be disposed between the anode and the light-emitting layer. The hole injection layer may be composed of two or more layers in order to lower an energy barrier for injecting holes from the anode to a hole transport layer or an electron blocking layer (or a voltage for injecting a hole). Each of the layers may comprise two or more compounds. The hole transport layer or electron blocking layer may be composed of two or more layers. Wherein the hole auxiliary layer or the auxiliary light-emitting layer is disposed between the hole transport layer and the light-emitting layer, and modulates hole mobility. The hole auxiliary layer or the auxiliary light-emitting layer has the effects to provide improved efficiency and lifespan of the organic electroluminescent device.

An electron buffering layer, a hole blocking layer, an electron transport layer, an electron injection layer, or a combination thereof may be disposed between the light-emitting layer and the cathode. The electron buffering layer may be composed of two or more layers in order to control the electron injection and improve characteristics of interface between the light-emitting layer and the electron injection layer. Each of the layers may comprise two or more compounds. The hole blocking layer or electron transport layer may be composed of two or more layers, and each of the layers may comprise two or more compounds.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, any of dry film-forming methods such as vacuum evaporation, sputtering, plasma, and ion plating methods, or wet film-forming methods such as spin coating, dip coating, and flow coating methods can be used. A co-evaporation or a mixture-evaporation is used for forming a film of the first host material and a film of the second host material. The co-evaporation indicates a process for two or more materials to be deposited as a mixture, by introducing each of the two or more materials into respective crucible cells, and applying electric current to the cells for each of the materials to be evaporated. Herein, a mixture-evaporation indicates a process for two or more materials to be deposited as a mixture, by mixing the two or more materials in one crucible cell before the deposition, and applying electric current to the cell for the mixture to be evaporated.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

A display system or a lighting system using the organic electroluminescent device of the present disclosure can be produced.

Hereinafter, for a more in-depth understanding of the present disclosure, the luminescent properties of the organic electroluminescent device comprising the host compound of the present disclosure will be explained.

Hereinafter, the organic electroluminescent compound of the present disclosure, the preparation method and the physical properties of the compound, and the luminescent properties of the organic electroluminescent device comprising the compound will be explained in detail with reference to the following examples.

[EXAMPLE 1] PREPARATION OF COMPOUND H2-2

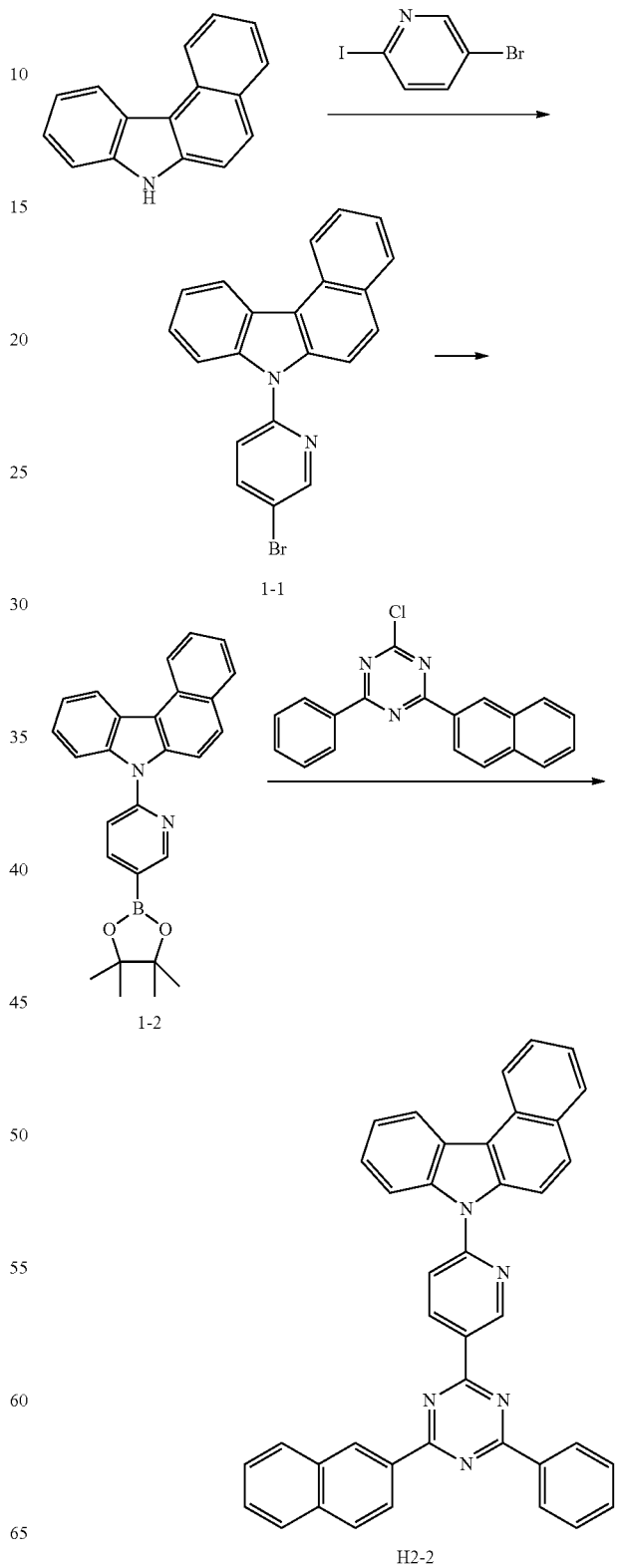

1) Preparation of Compound 1-1

After introducing a compound 7H-benzo[c]carbazole (30 g, 138.1 mmol), 5-bromo-2-iodopyridine (58.8 g, 207.1 mmol), CuI (12.5 g, 65.4 mmol), $K_3PO_4$ (73 g, 345.2 mmol), ethylene diamine (8.3 g, 138.1 mmol), and toluene (600 mL) into a flask, the mixture was stirred under reflux at 120° C. for 4 hours. After completion of the reaction, the mixture was extracted with ethyl acetate and purified water, and the obtained organic layer was concentrated under reduced pressure. The organic layer was subjected to silica gel column chromatography (methylene chloride(MC):hexane (Hex)) to obtain compound 1-1 (16 g, yield: 31%).

2) Preparation of Compound 1-2

After introducing compound 1-1 (16 g, 42.86 mmol), pinacolatodiboron (13.1 g, 51.44 mmol), $PdCl_2 (PPh_3)_2$ (3 g, 4.3 mmol), potassium acetate (KOAc) (10.5 g, 107 mmol), and 1,4-dioxane (200 mL) into a flask, the mixture was stirred under reflux at 120° C. for 2 hours. After completion of the reaction, the mixture was extracted with ethyl acetate and purified water, and the obtained organic layer was dried under reduced pressure. The organic layer was subjected to silica gel column chromatography (MC:Hex) to obtain compound 1-2 (11 g, yield: 61%).

3) Preparation of Compound H2-2

After introducing compound 1-2 (11 g, 26.17 mmol), 2-chloro-4-(naphthalen-2-yl)-6-phenyl-1,3,5-triazine (8.3 g, 26.17 mmol), $Na_2CO_3$ (6.9 g, 65.42 mmol), $Pd(PPh_3)_4$ (1.5 g, 1.3 mmol), tetrahydrofuran (THF) (100 mL), and purified water (30 mL) into a flask, the mixture was stirred under reflux at 120° C. for 4 hours. After completion of the reaction, the mixture was extracted with ethyl acetate and purified water, and the obtained organic layer was concentrated under reduced pressure. The organic layer was subjected to silica gel column chromatography (MC:Hex) to obtain compound H2-2 (6.54 g, yield: 43.1%).

[DEVICE EXAMPLES 1 TO 4] OLED COMPRISING A FIRST HOST COMPOUND AND A SECOND HOST COMPOUND OF THE PRESENT DISCLOSURE AS A HOST

An OLED was produced using the organic electroluminescent compound of the present disclosure as follows. A transparent electrode indium tin oxide (ITO) thin film (10Ω/sq) on a glass substrate for an OLED (Geomatec) was subjected to an ultrasonic washing with acetone, ethanol, and distilled water sequentially, and was then stored in isopropanol. The ITO substrate was then mounted on a substrate holder of a vacuum vapor depositing apparatus. HI-1 was introduced into a cell of said vacuum vapor depositing apparatus, and then the pressure in the chamber of said apparatus was controlled to $10^{-6}$ torr. Thereafter, an electric current was applied to the cell to evaporate the above introduced material, thereby forming a first hole injection layer having a thickness of 80 nm on the ITO substrate. HI-2 was then introduced into another cell of said vacuum vapor depositing apparatus, and evaporated by applying electric current to the cell, thereby forming a second hole injection layer having a thickness of 5 nm on the first hole injection layer. HT-1 was introduced into one cell of the vacuum vapor depositing apparatus, and evaporated by applying electric current to the cell, thereby forming a first hole transport layer having a thickness of 10 nm on the second hole injection layer. HT-3 was introduced into another cell of the vacuum vapor depositing apparatus, and evaporated by applying electric current to the cell, thereby forming a second hole transport layer having a thickness of 60 nm on the first hole transport layer. After forming the hole injection layer and the hole transport layer, a light-emitting layer was deposited thereon as follows. A first host material and a second host material shown in Table 1 below were introduced, as host materials, into a cell of the vacuum vapor depositing apparatus, and compound D-71 was introduced, as a dopant, into another cell. The two host compounds were then evaporated at the same rate of 1:1, so that the dopant was deposited in a doping amount of 3 wt % based on the total amount of the host and dopant to form a light-emitting layer having a thickness of 40 nm on the second hole transport layer. Compounds ET-1 and EI-1 were then introduced into another two cells of the vacuum vapor depositing apparatus, respectively, and evaporated at the same rate of 1:1, thereby forming an electron transport layer having a thickness of 30 nm on the light-emitting layer. After depositing compound EI-1 as an electron injection layer having a thickness of 2 nm on the electron transport layer, an Al cathode having a thickness of 80 nm was then deposited by another vacuum vapor deposition apparatus on the electron injection layer to produce an OLED. Evaluation results of the devices produced in Device Examples 1 to 4 are shown in Table 1 below.

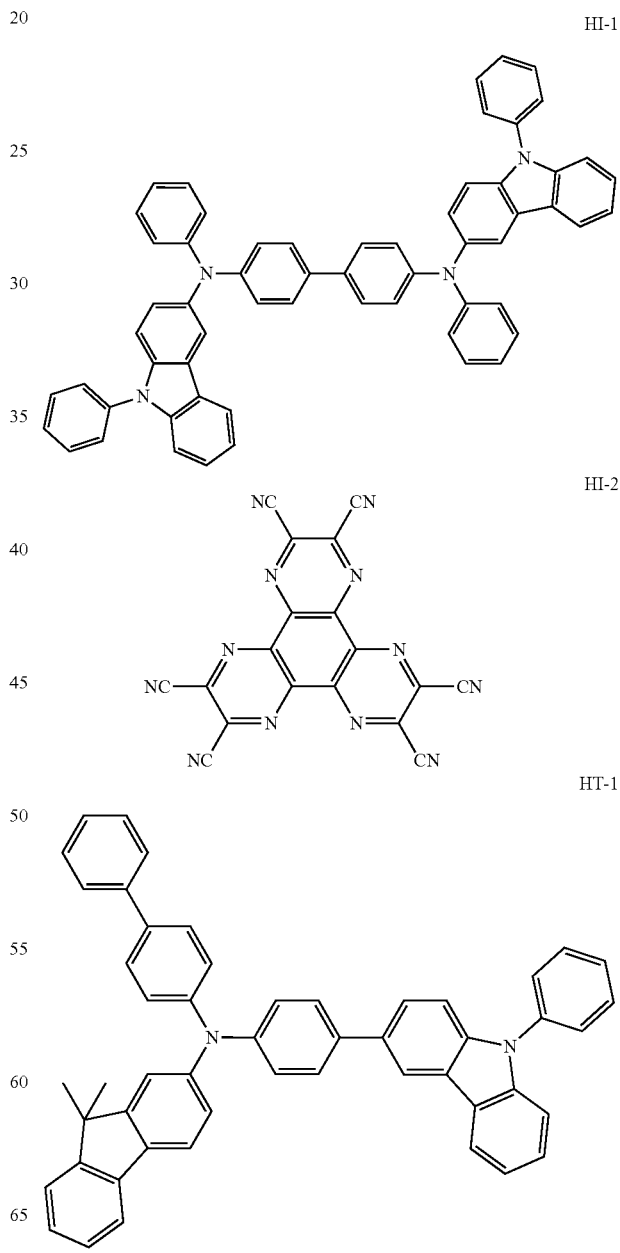

HT-3
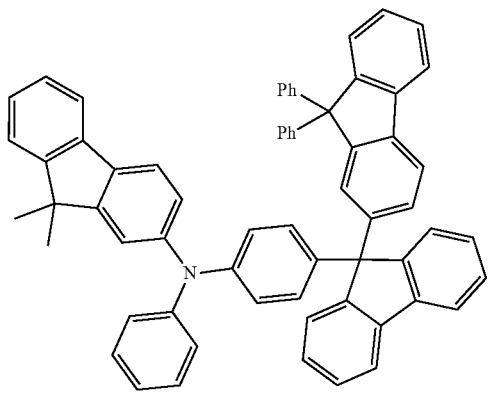
ET-1
EI-1
D-71
TABLE 1
| Device Example No. | The 1st Host | The 2nd Host | Driving Voltage (V) | Efficiency (cd/A) | The Emission Color | T98 Life-span (hr) |
|---|---|---|---|---|---|---|
| Device Example 1 | H1-7 | H2-2 | 3.4 | 29.3 | Red | 76 |
TABLE 1-continued
| Device Example No. | The 1st Host | The 2nd Host | Driving Voltage (V) | Efficiency (cd/A) | The Emission Color | T98 Life-span (hr) |
|---|---|---|---|---|---|---|
| Device Example 2 | H1-81 | H2-2 | 3.8 | 27.8 | Red | 153 |
| Device Example 3 | H1-92 | H2-2 | 3.5 | 27.7 | Red | 56 |
| Device Example 4 | H1-14 | H2-2 | 3.4 | 29.1 | Red | 62 |
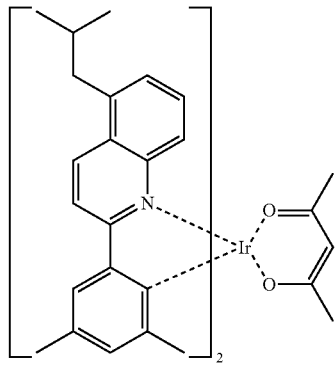
H1-7
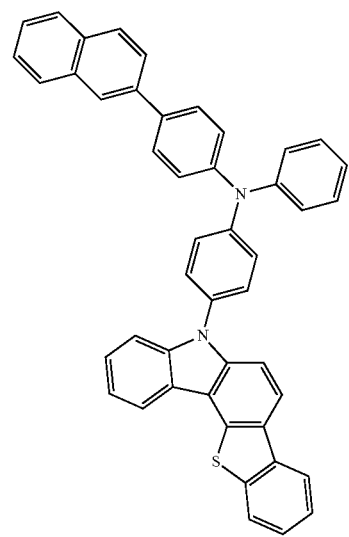
H1-81

TABLE 1-continued

| Device Example No. | The 1st Host | The 2nd Host | Driving Voltage (V) | Efficiency (cd/A) | The Emission Color | T98 Life-span (hr) |
|---|---|---|---|---|---|---|

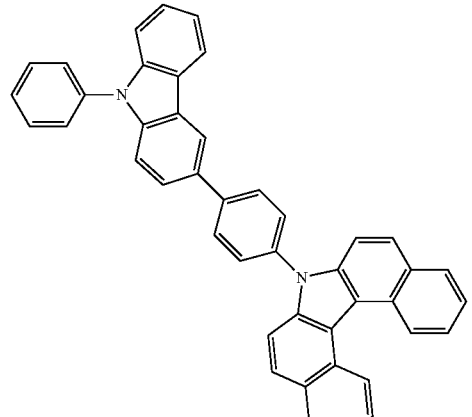

H1-92

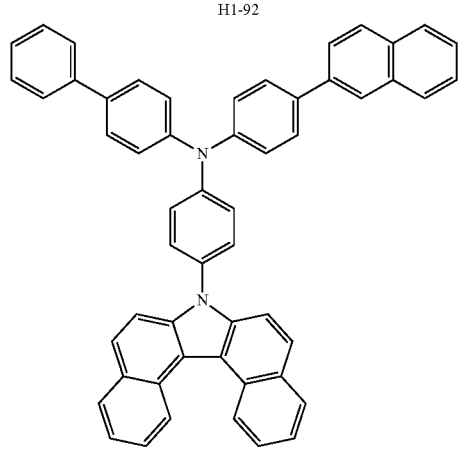

H1-14

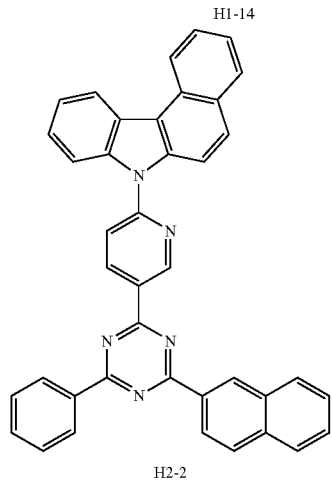

H2-2

[DEVICE EXAMPLES 5 TO 8] OLED COMPRISING A FIRST HOST COMPOUND AND A SECOND HOST COMPOUND OF THE PRESENT DISCLOSURE AS A HOST

In Device Examples 5 to 8, OLEDs were produced in the same manner as in Device Examples 1 to 4, except that a first hole injection layer having a thickness of 90 nm was formed, the doping amount of the dopant was 2 wt %, an electron transport layer having a thickness of 35 nm was deposited, and the first host was changed as shown in Table 2 below. Evaluation results of the devices produced in Device Examples 5 to 8 are shown in Table 2 below.

TABLE 2

| Device Example No. | The 1st Host | The 2nd Host | Driving Voltage (V) | Efficiency (cd/A) | The Emission Color | T98 Life-span (hr) |
|---|---|---|---|---|---|---|
| Device Example 5 | H1-80 | H2-2 | 3.5 | 28.7 | Red | 100 |
| Device Example 6 | H1-90 | H2-2 | 3.6 | 30.3 | Red | 85 |
| Device Example 7 | H1-93 | H2-2 | 3.5 | 29.9 | Red | 82 |
| Device Example 8 | H1-91 | H2-2 | 3.6 | 30.0 | Red | 64 |

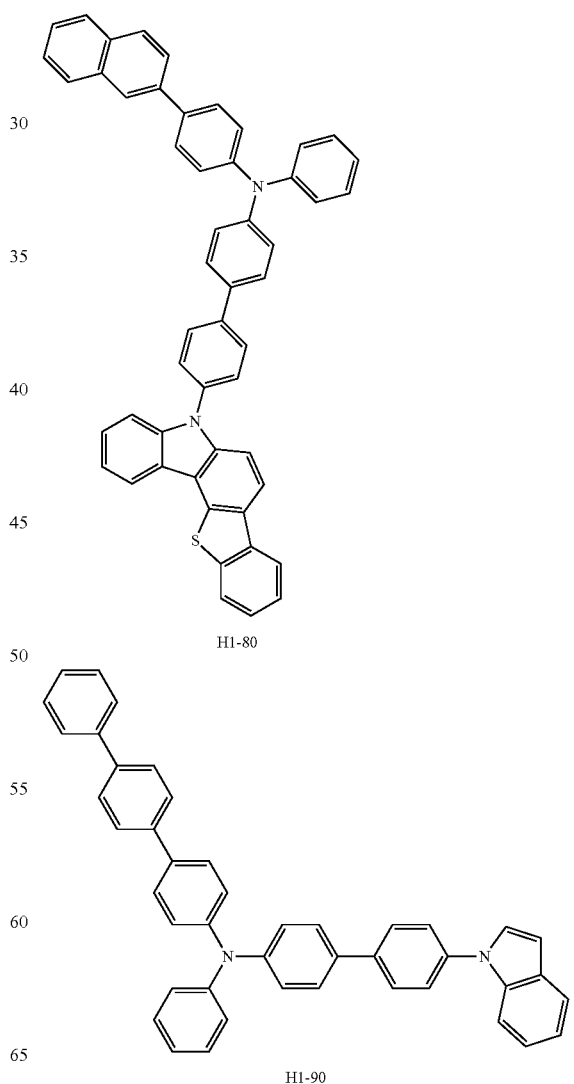

H1-80

H1-90

TABLE 2-continued

| Device Example No. | The 1st Host | The 2nd Host | Driving Voltage (V) | Efficiency (cd/A) | The Emission Color | T98 Lifespan (hr) |
|---|---|---|---|---|---|---|

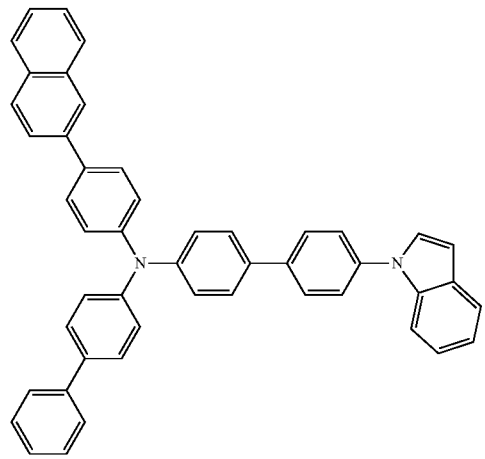

H1-91

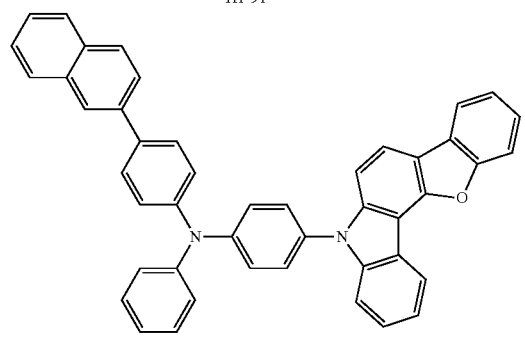

H1-93

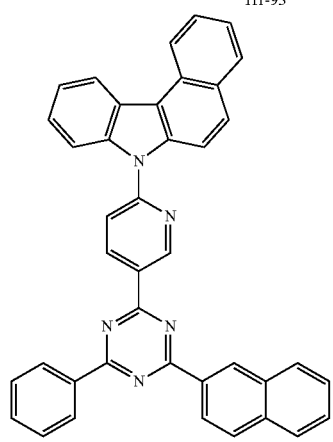

H2-2

[COMPARATIVE DEVICE EXAMPLE 1] OLED COMPRISING A CONVENTIONAL ORGANIC ELECTROLUMINESCENT COMPOUND

An OLED was produced in the same manner as in Device Examples 1 to 4, except that the first host shown in Table 3 below was employed as a host for a light-emitting layer and the second host was not employed.

TABLE 3

| Device Example No. | The 1st Host | The 2nd Host | Driving Voltage (V) | Efficiency (cd/A) | The Emission Color | T98 Lifespan (hr) |
|---|---|---|---|---|---|---|
| Comparative Device Example 1 | H1-92 | — | 8.1 | 13.6 | Red | X |

*X indicates that lifespan of a device was too short to be measured.

[COMPARATIVE DEVICE EXAMPLE 2] OLED COMPRISING A CONVENTIONAL ORGANIC ELECTROLUMINESCENT COMPOUND

An OLED was produced in the same manner as in Device Examples 1 to 4, except that the second host shown in Table 4 below was employed as a host for a light-emitting layer and the first host was not employed.

TABLE 4

| Device Example No. | The 1st Host | The 2nd Host | Driving Voltage (V) | Efficiency (cd/A) | The Emission Color | T98 Lifespan (hr) |
|---|---|---|---|---|---|---|
| Comparative Device Example 2 | — | H2-2 | 3.3 | 24.9 | Red | 7 |

[COMPARATIVE DEVICE EXAMPLE 3] OLED COMPRISING A CONVENTIONAL ORGANIC ELECTROLUMINESCENT COMPOUND

An OLED was produced in the same manner as in Device Examples 1 to 4, except that the first host and the second host shown in Table 5 below were employed as a host for a light-emitting layer.

TABLE 5

| Device Example No. | The 1st Host | The 2nd Host | Driving Voltage (V) | Efficiency (cd/A) | The Emission Color | T98 Lifespan (hr) |
|---|---|---|---|---|---|---|
| Comparative Device Example 3 | H1-7 | Compound A | 3.5 | 31.1 | Red | 40 |

TABLE 5-continued

| Device Example No. | The 1st Host | The 2nd Host | Driving Voltage (V) | Efficiency (cd/A) | The Emission Color | T98 Lifespan (hr) |
|---|---|---|---|---|---|---|

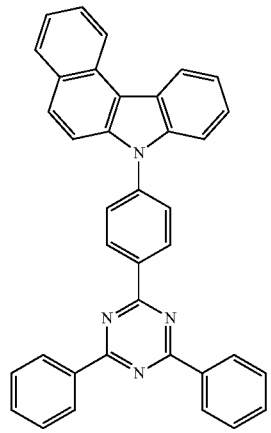

Compound A

By using a specific combination of two or more host compounds according to the present disclosure, the organic electroluminescent device of the present disclosure has luminous efficiency at least equivalent to or higher than conventional devices and has lifespan longer than conventional devices.

The invention claimed is:

1. A host material that comprises one or more first host compounds and one or more second host compounds wherein the first host compound is represented by the following formula 1 and the second host compound is represented by the following formula 2:

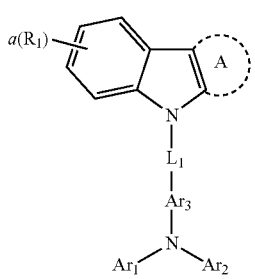

(1)

wherein $L_1$ represents a single bond or a substituted or unsubstituted (C6-C30)arylene, A represents hydrogen, a substituted or unsubstituted phenyl, a substituted or unsubstituted naphthyl, a substituted or unsubstituted fluorenyl, a substituted or unsubstituted dibenzothiophenyl, or a substituted or unsubstituted dibenzofuranyl, $Ar_1$, $Ar_2$, and $Ar_3$, each independently, represent a substituted or unsubstituted (C6-C30)aryl(ene), or a substituted or unsubstituted 3- to 30-membered heteroaryl(ene); or $Ar_2$ and $Ar_3$ may be linked to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur, $R_1$ represents deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or $R_1$ may be linked to an adjacent substituent(s) to form a substituted or unsubstituted 3 to 30-membered, mono- or polycyclic, alicyclic or aromatic ring, or a combination of the alicyclic ring and the aromatic ring, wherein the heteroaryl(ene) contains one or more heteroatoms selected from the group consisting of B, N, O, S, Si, and P, a represents an integer of 0 to 4, and when a is an integer of 2 or more, each of $R_1$ may be the same or different;

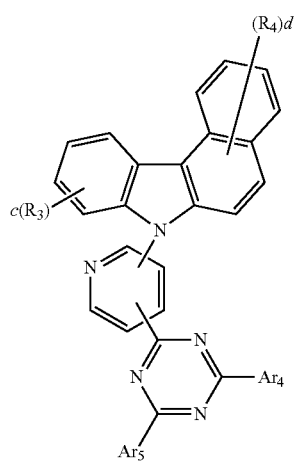

(2)

wherein $Ar_4$ and $Ar_5$, each independently, represent a substituted or unsubstituted (C6-C30)aryl, a substituted or unsubstituted (C3-C30)cycloalkyl, or a substituted or unsubstituted 3- to 30-membered heteroaryl, $R_3$ and $R_4$, each independently, represent deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino, wherein the heteroaryl contains one or more heteroatoms selected from the group consisting of B, N, O, S, Si, and P, and c represents an integer of 0 to 4; d represents an integer of 0 to 6; and when c or d is an integer of 2 or more, each of $R_3$ or $R_4$ may be the same or different.

2. The host material according to claim 1, wherein formula 2 is represented by any one of the following formulae 12 to 16:

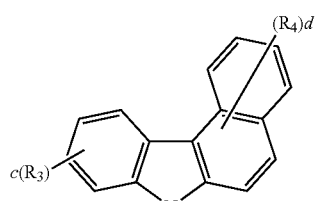
(12)

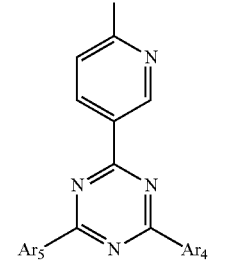
(13)

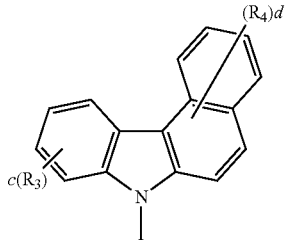
(14)

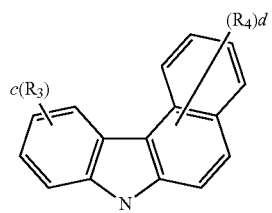
(15)

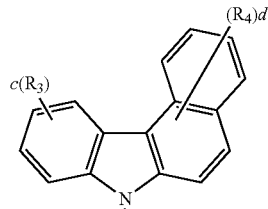
(16)

wherein $Ar_4$, $Ar_5$, $R_3$, $R_4$, c, and d are as defined in claim 1.

3. The host material according to claim 1, wherein the first host compound of formula 1 is selected from the group consisting of:

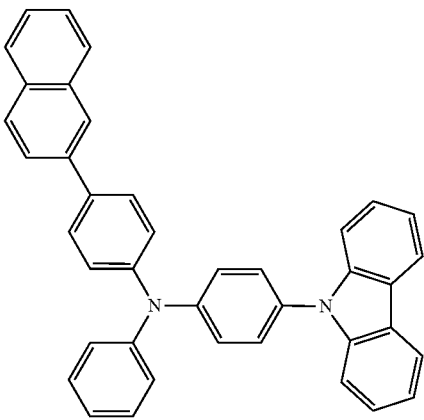
H1-1

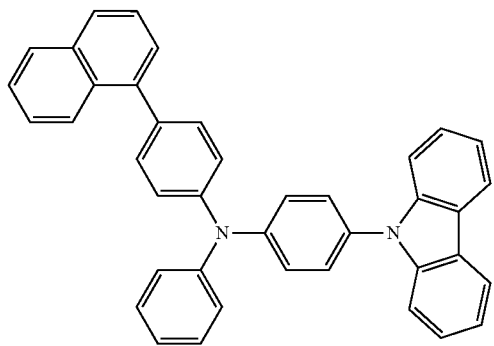
H1-2
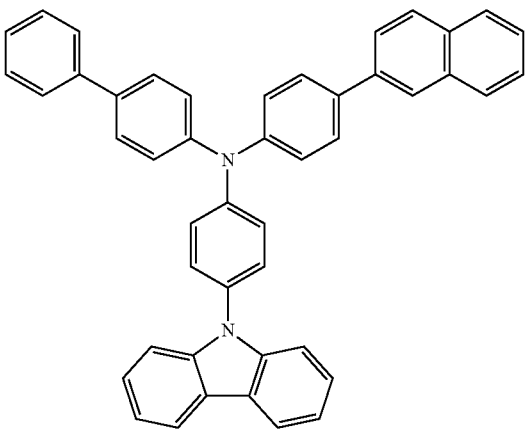
H1-6
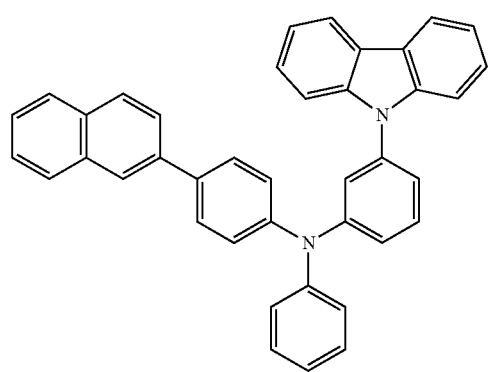
H1-3
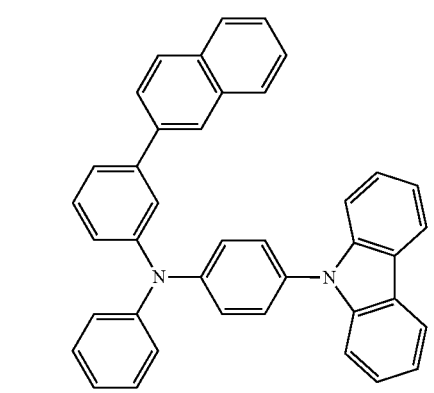
H1-4
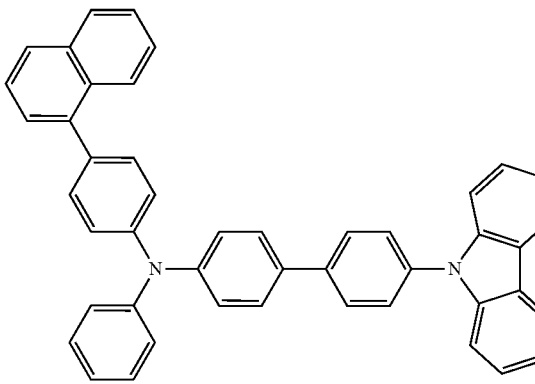
H1-7
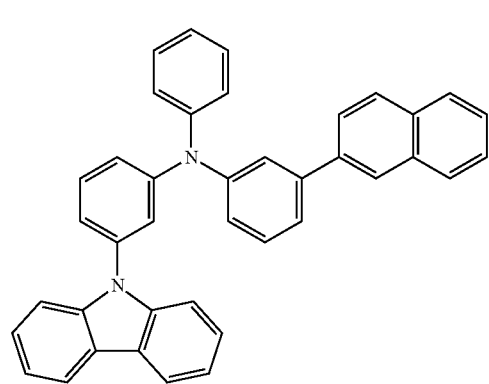
H1-5
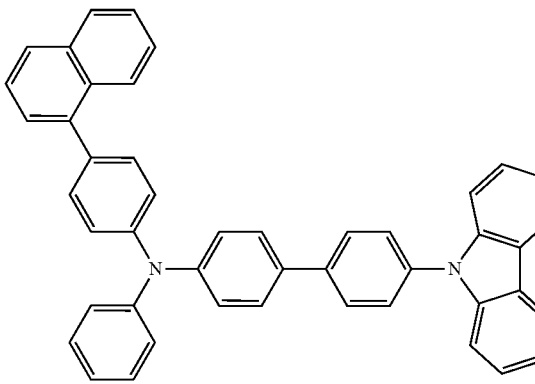
H1-8

H1-9
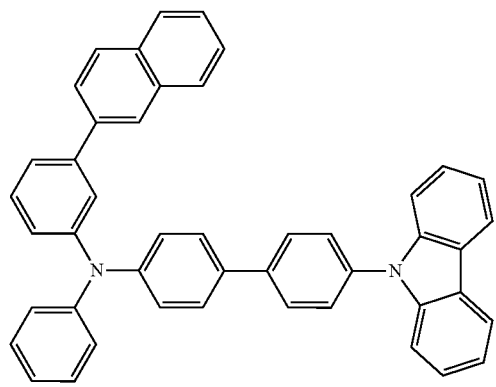
H1-10
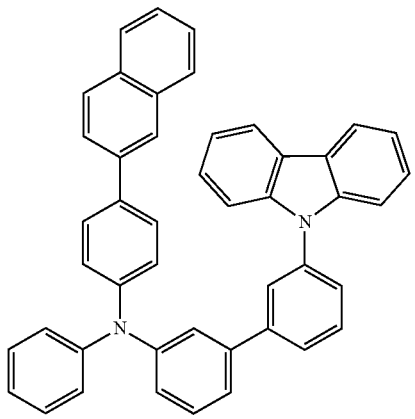
H1-11
H1-12
H1-13
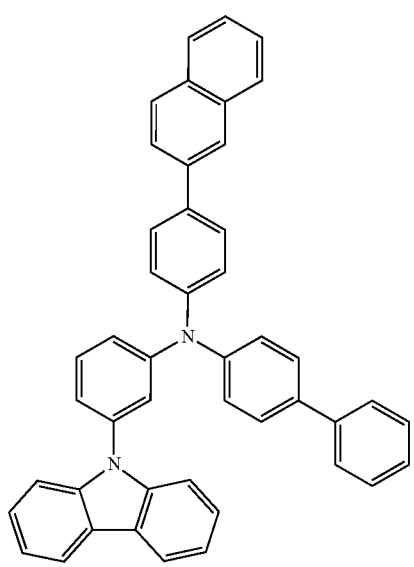
H1-14
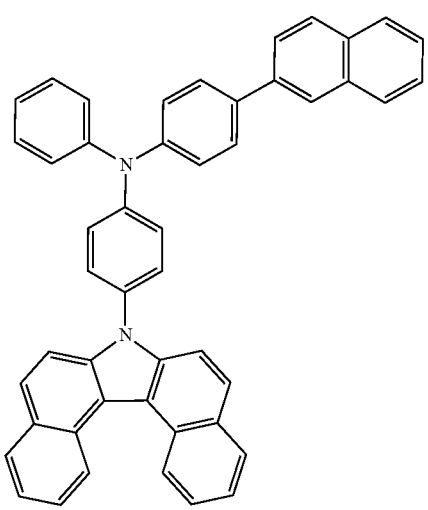

H1-15
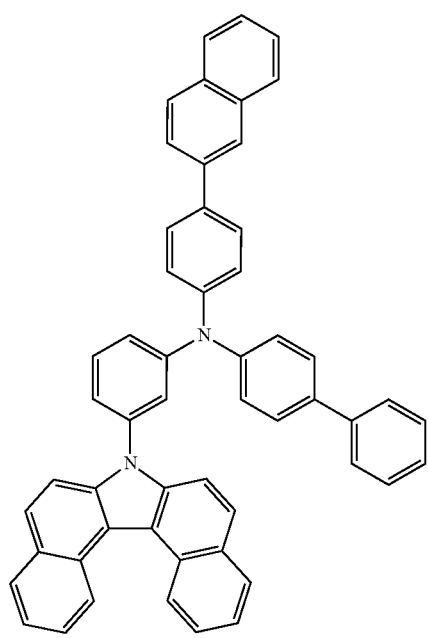
H1-17
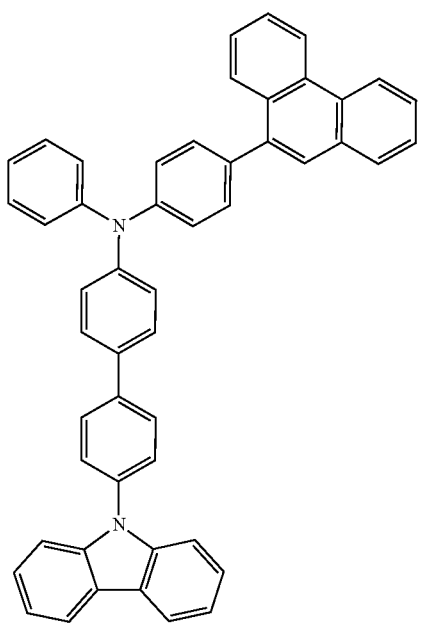
H1-16
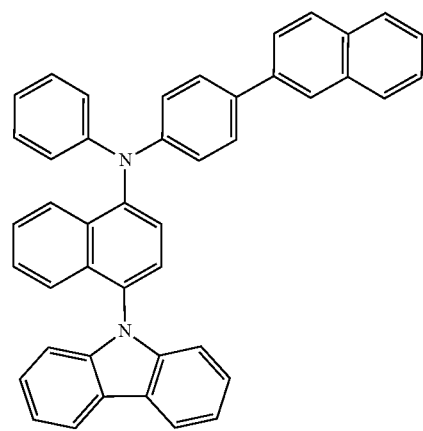
H1-18
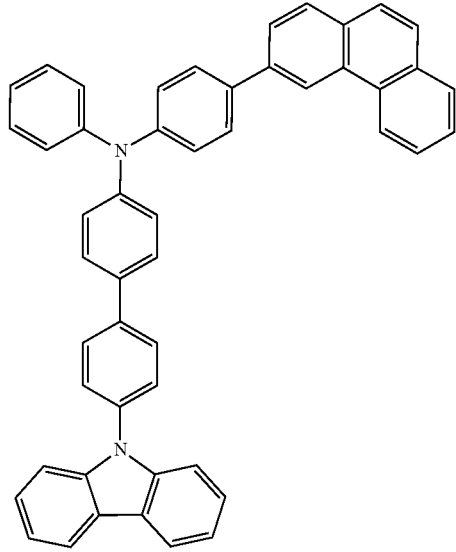

H1-19
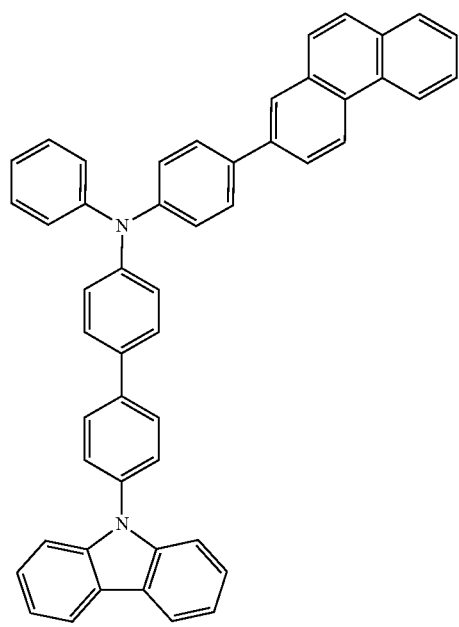
H1-20
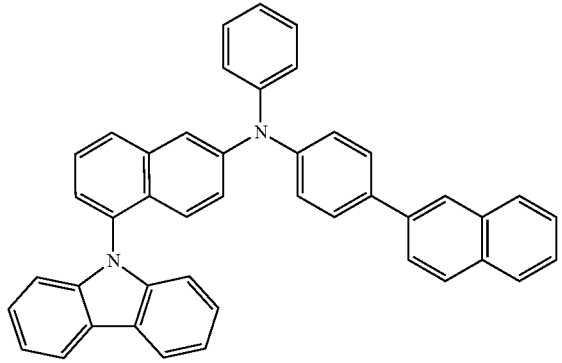
H1-21
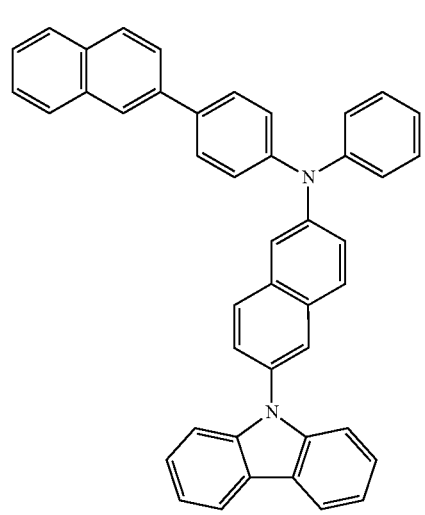
H1-22
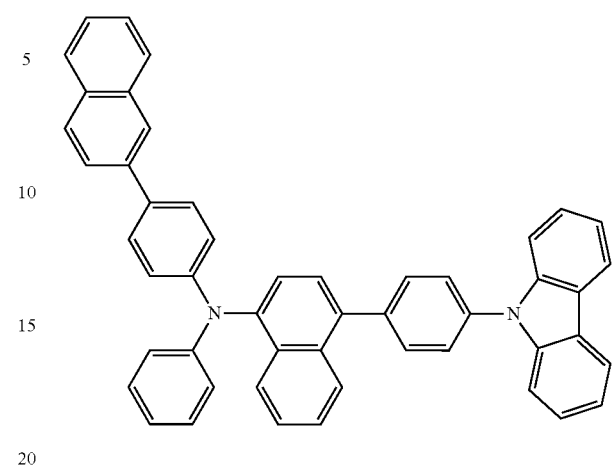
H1-23
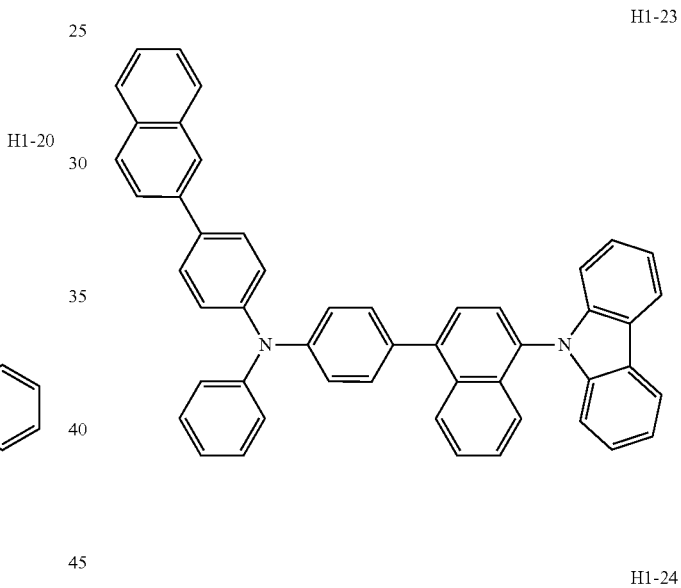
H1-24
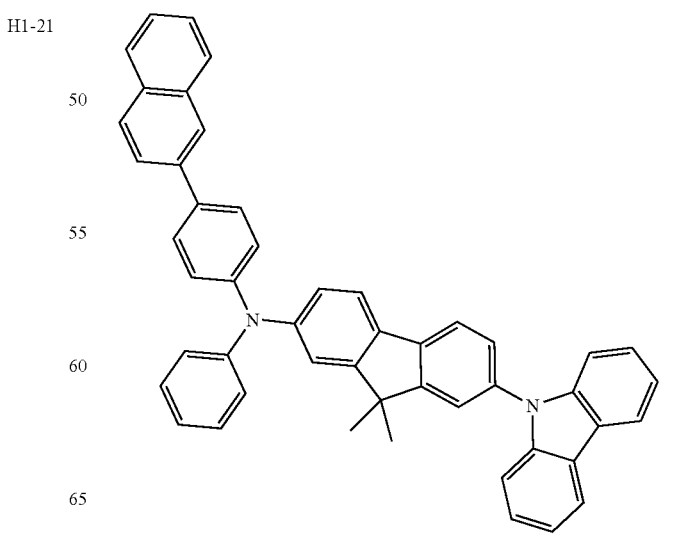

127
-continued
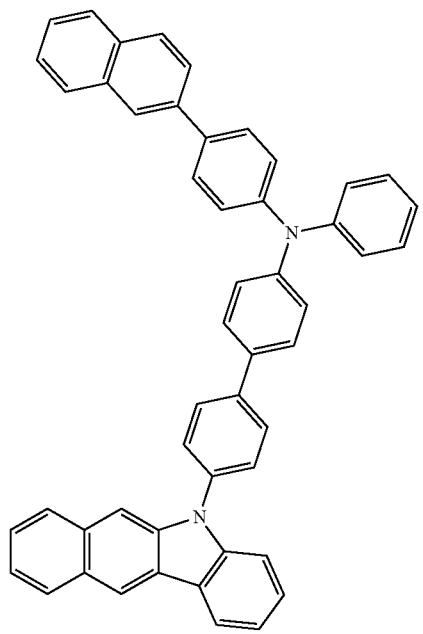
H1-25
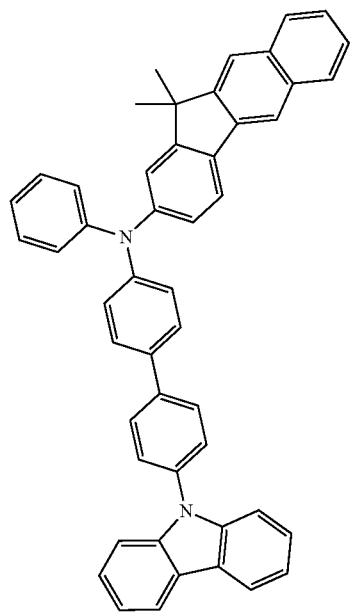
H1-26
128
-continued
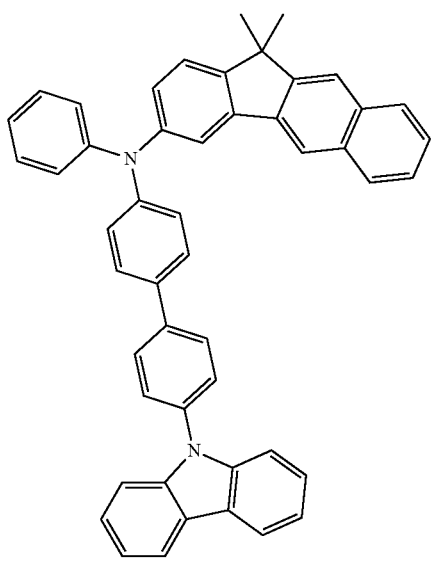
H1-27
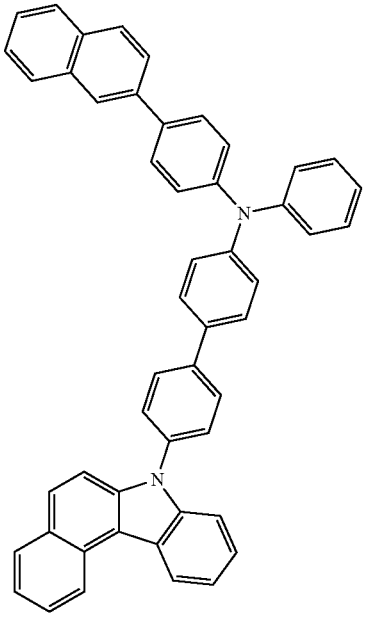
H1-28

-continued
H1-29
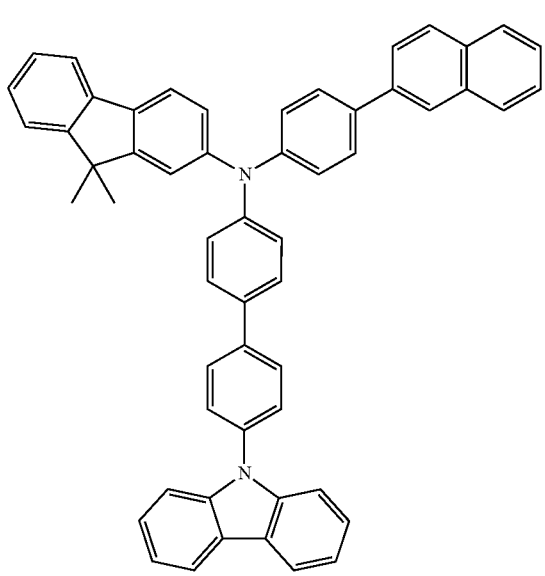
H1-30
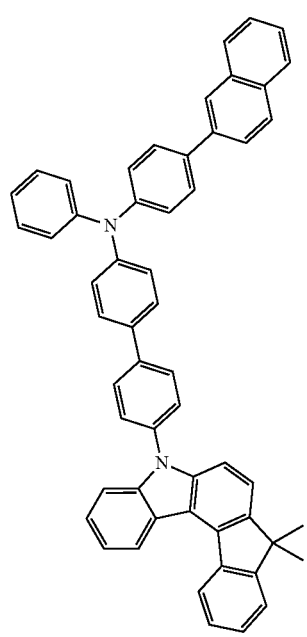
H1-31
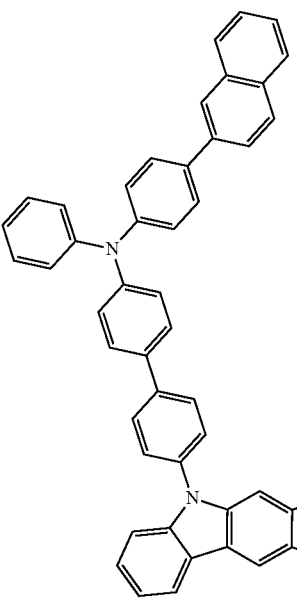
H1-32
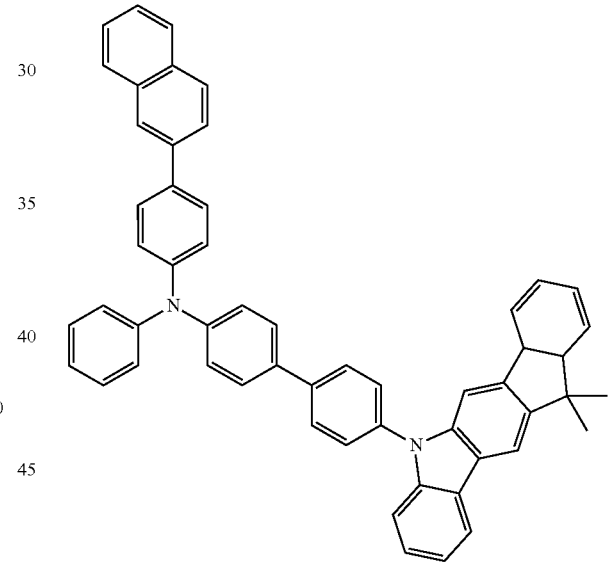
H1-33
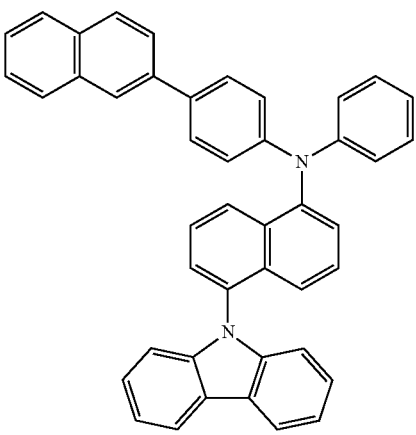

H1-34
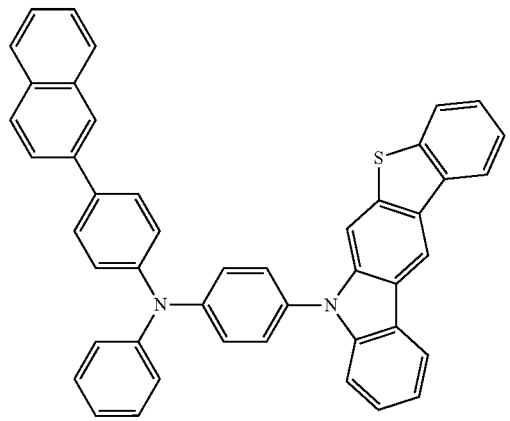
H1-35
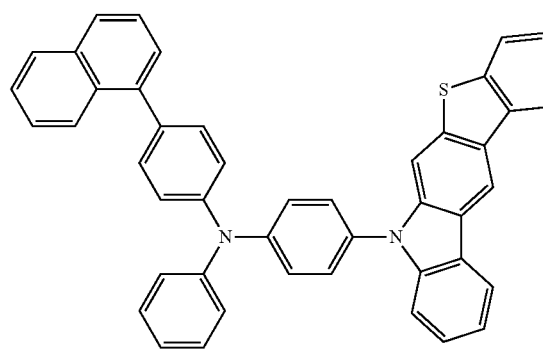
H1-36
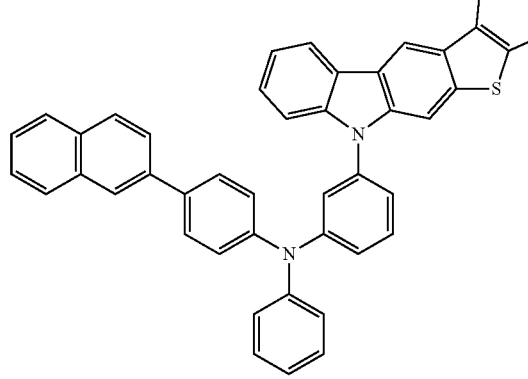
H1-37
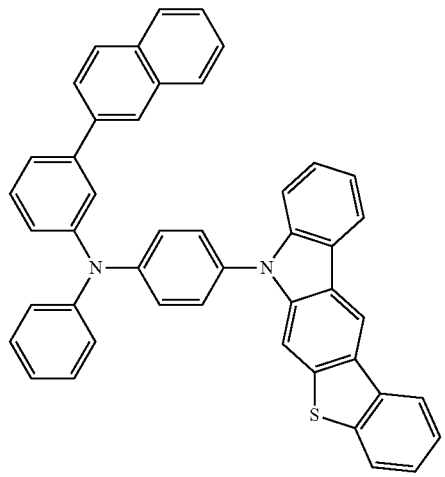
H1-38
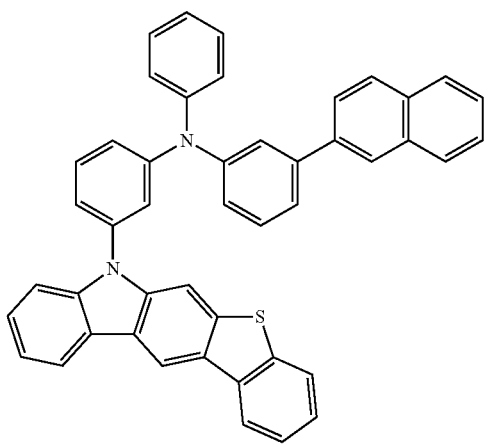
H1-39
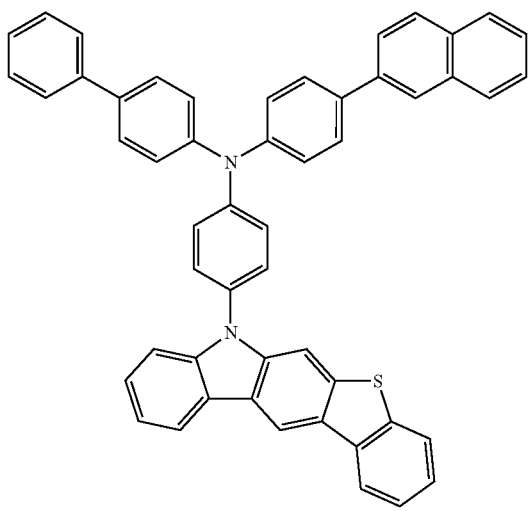

H1-40
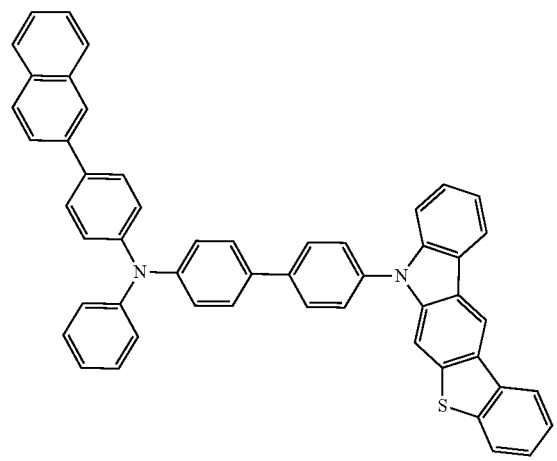
H1-41
H1-42
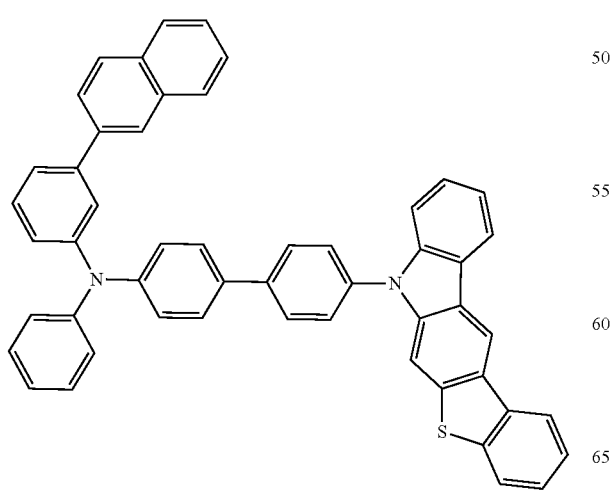
H1-43
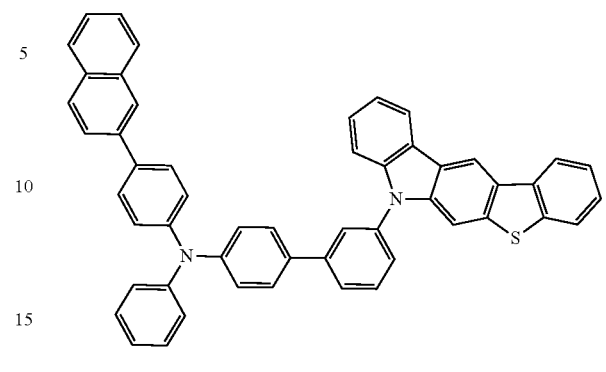
H1-44
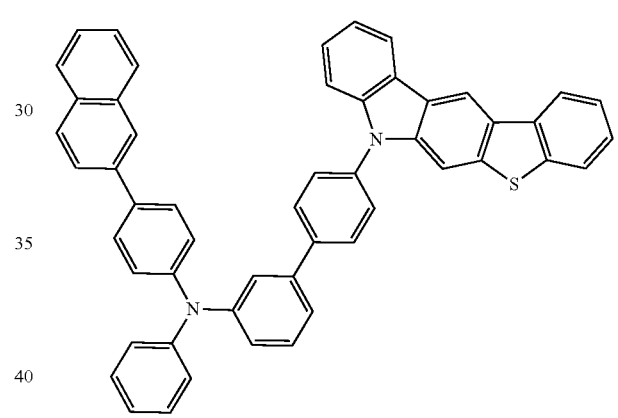
H1-45
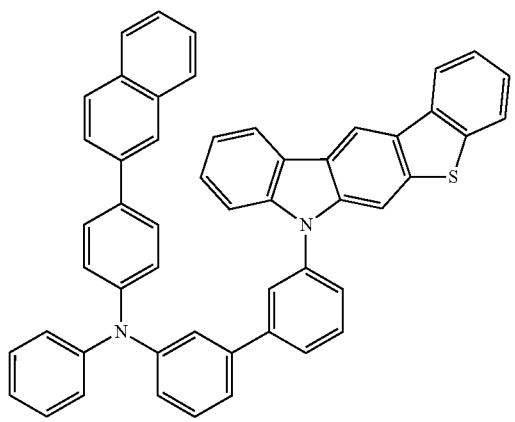

H1-46
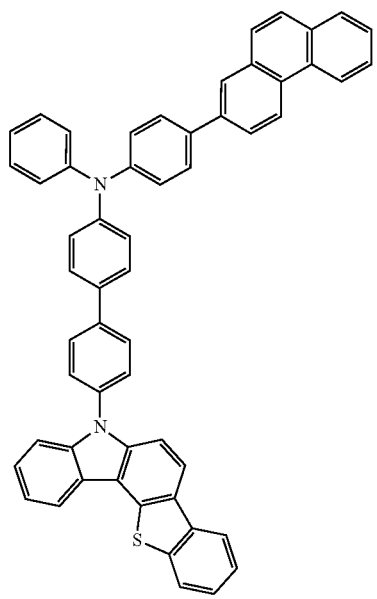
H1-47
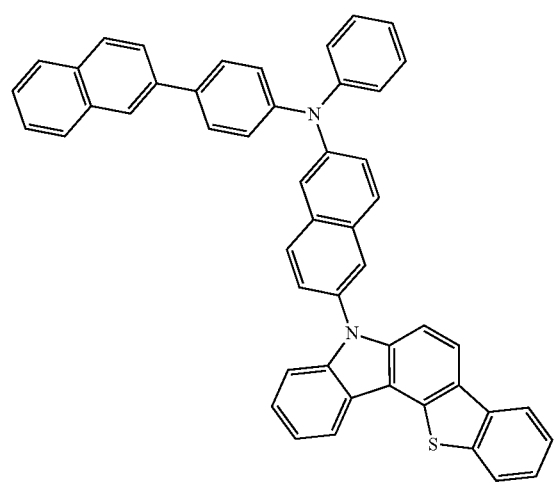
H1-48
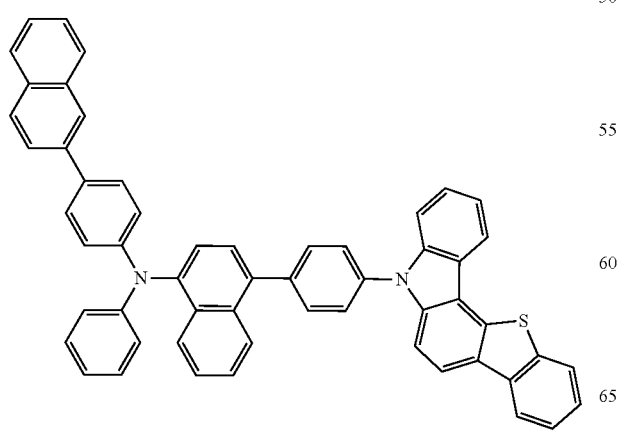
H1-49
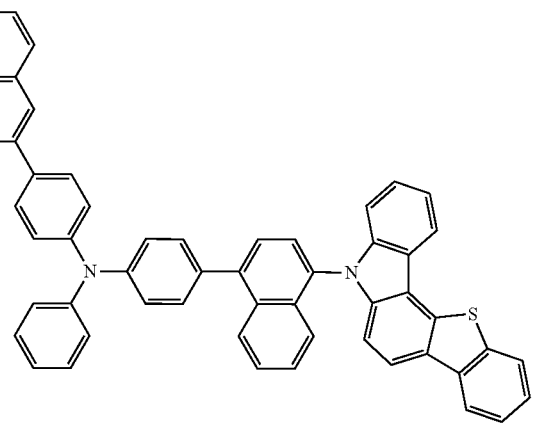
H1-50
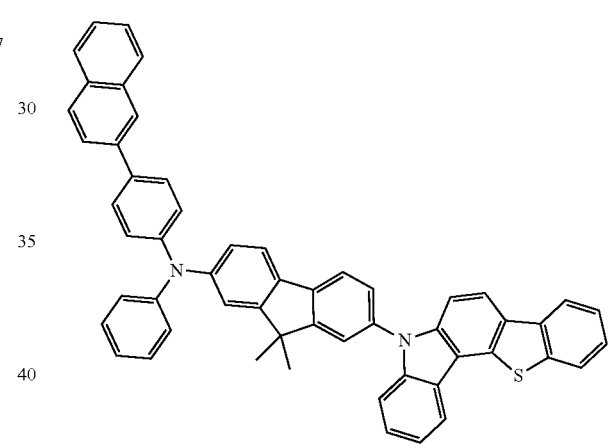
H1-51
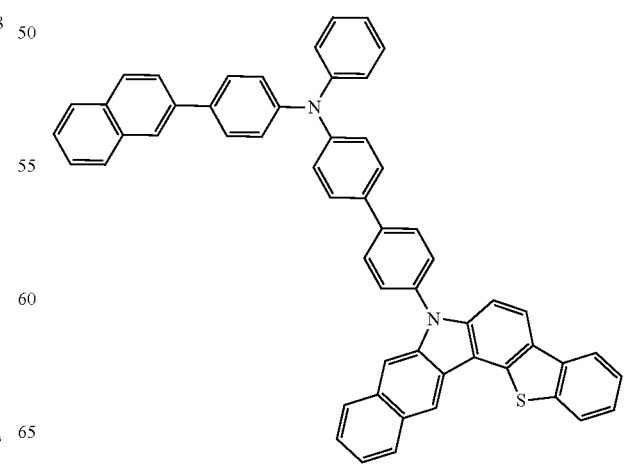

H1-52
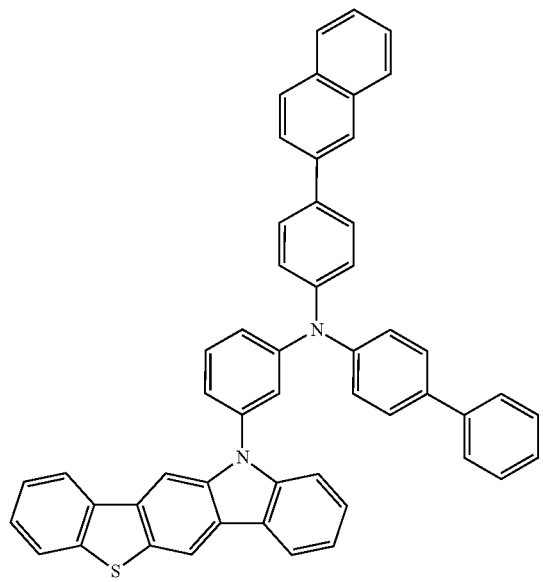
H1-53
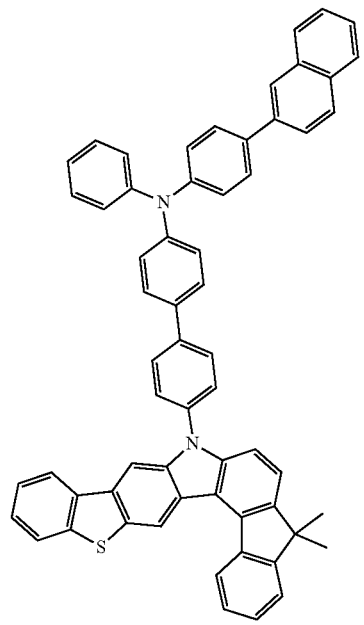
H1-54
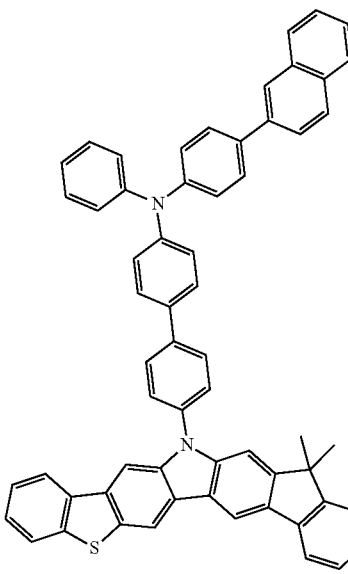
H1-55
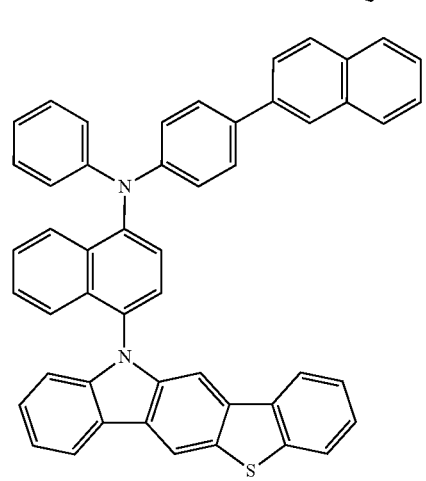
H1-56
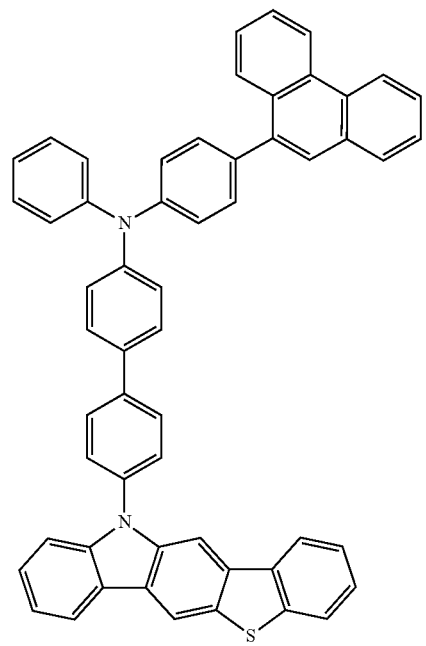

H1-57
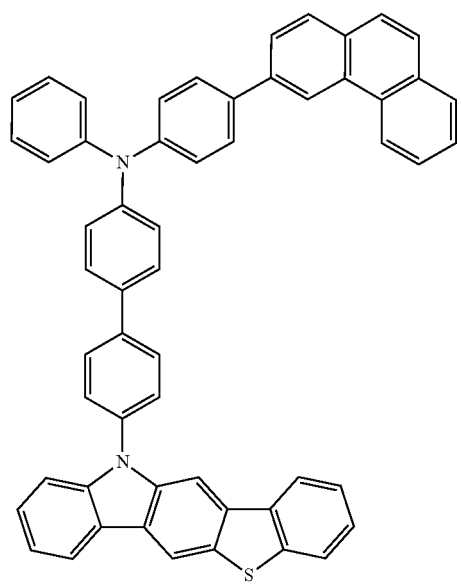
H1-58
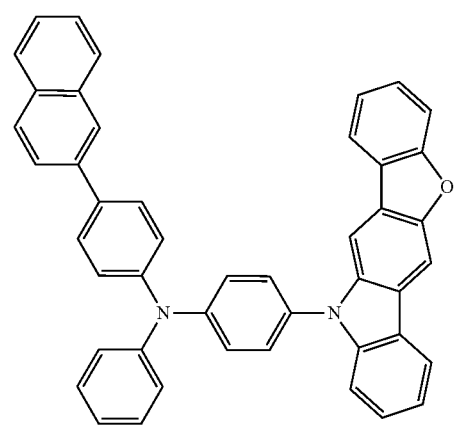
H1-59
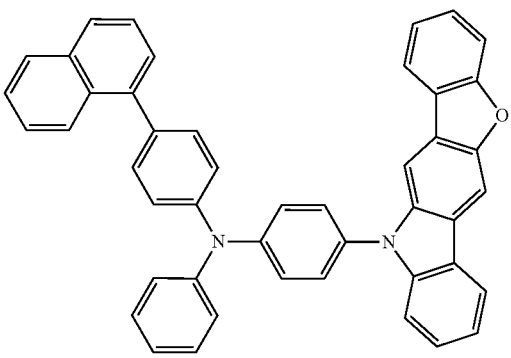
H1-60
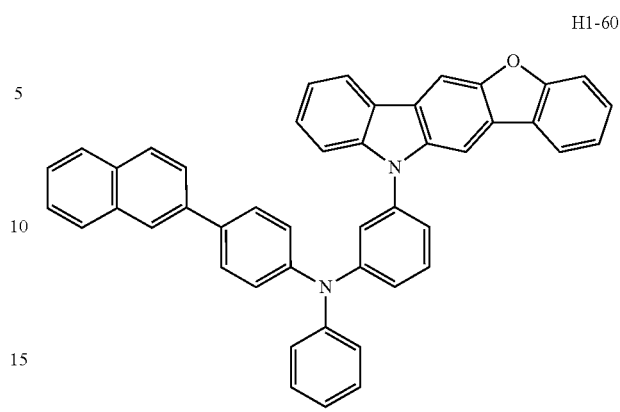
H1-61
H1-62
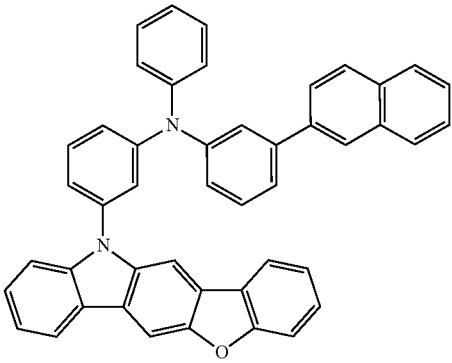

H1-63
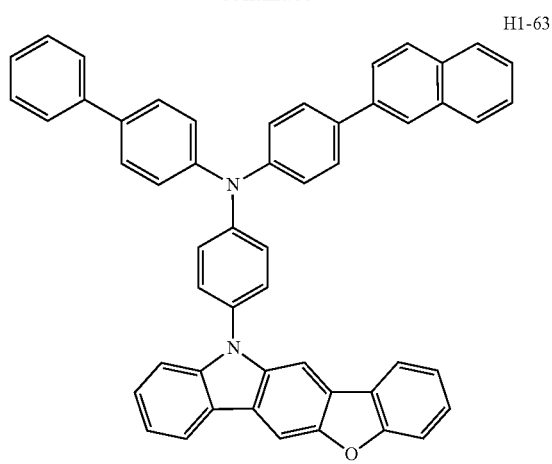
H1-66
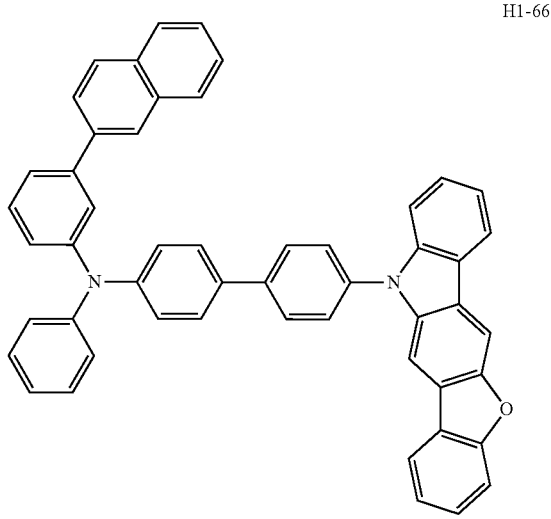
H1-64
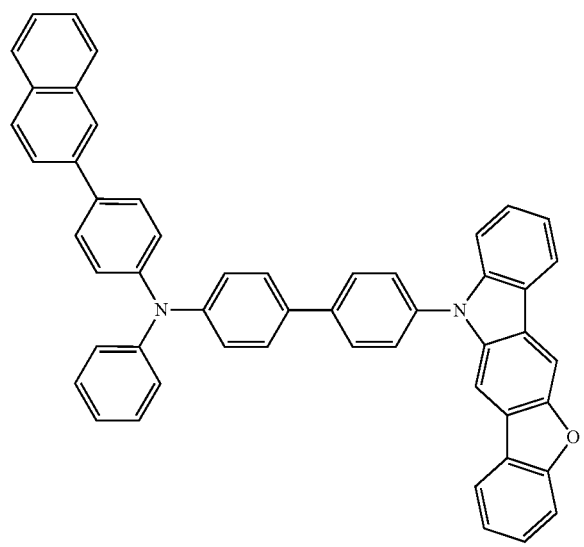
H1-67
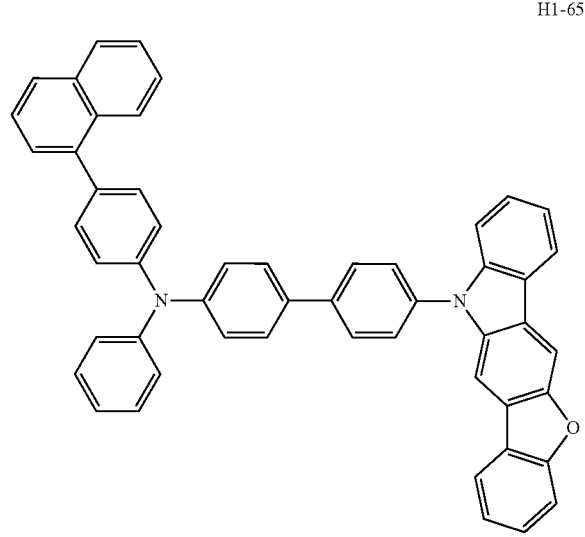
H1-65
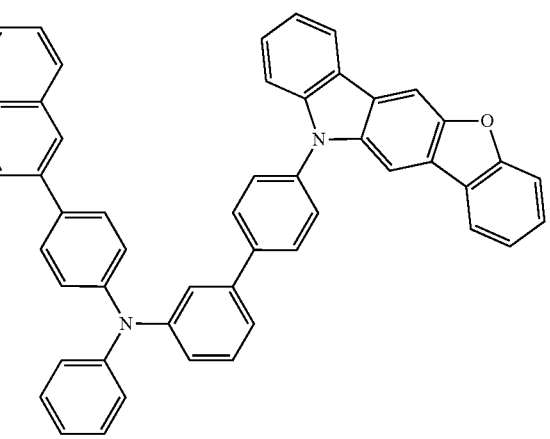
H1-68

H1-69
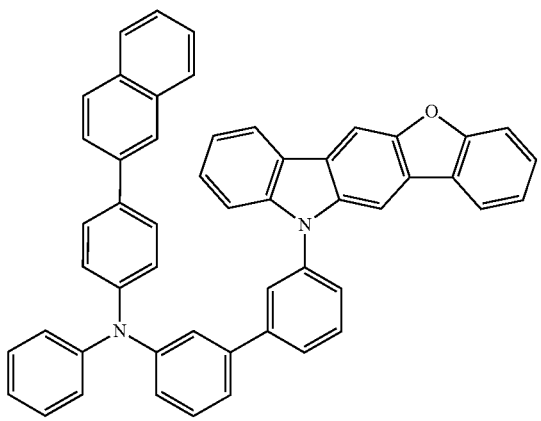
H1-71
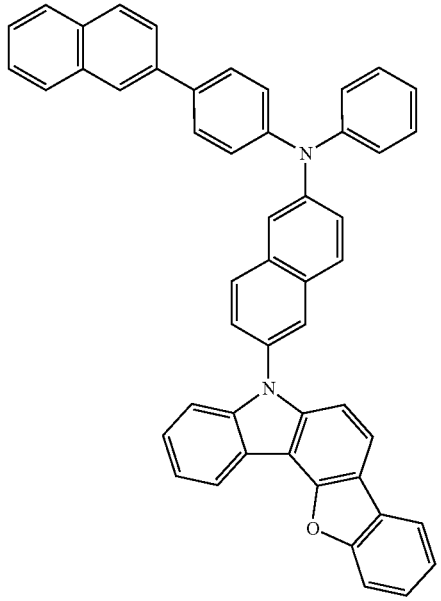
H1-70
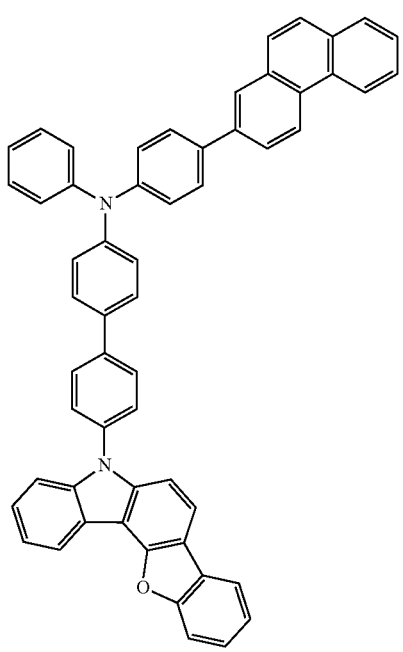
H1-72
H1-73
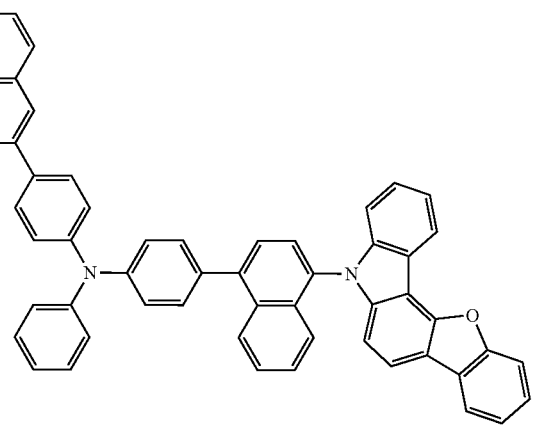

H1-74
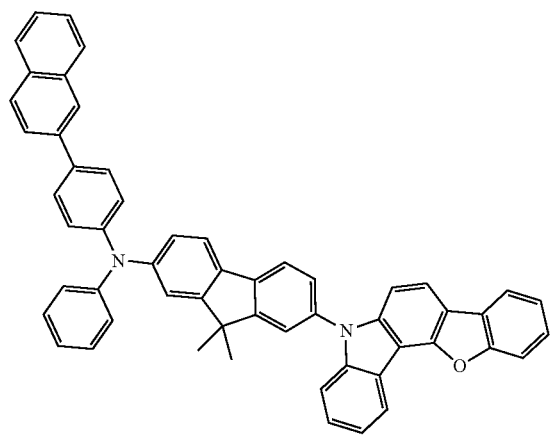
H1-75
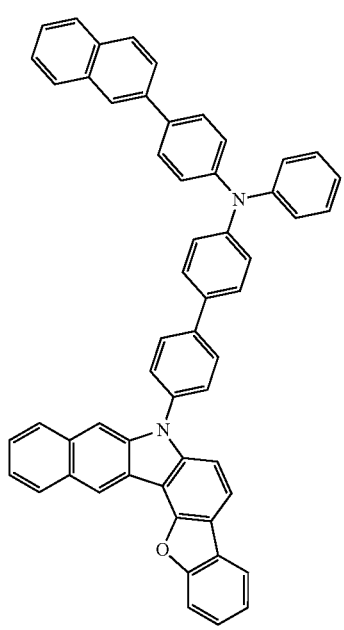
H1-76
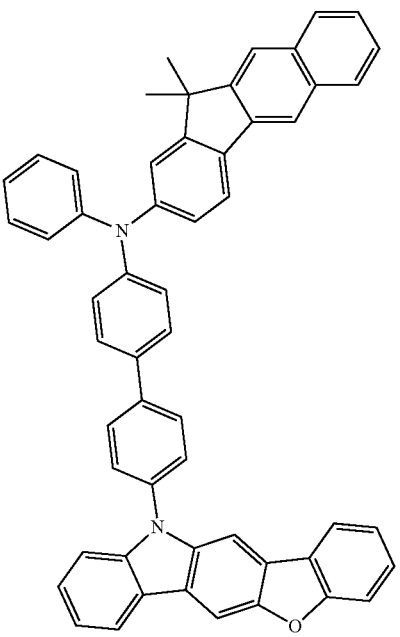
H1-77
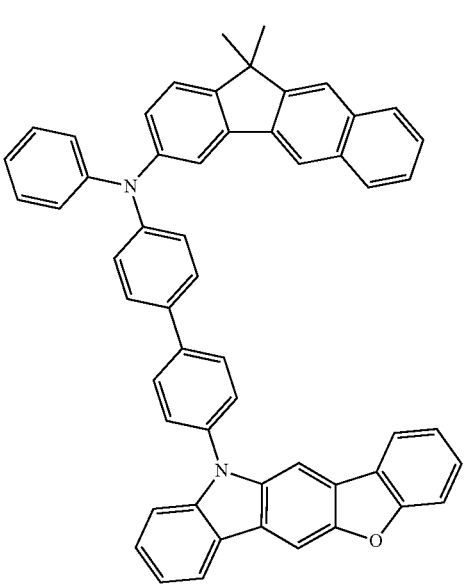

H1-78
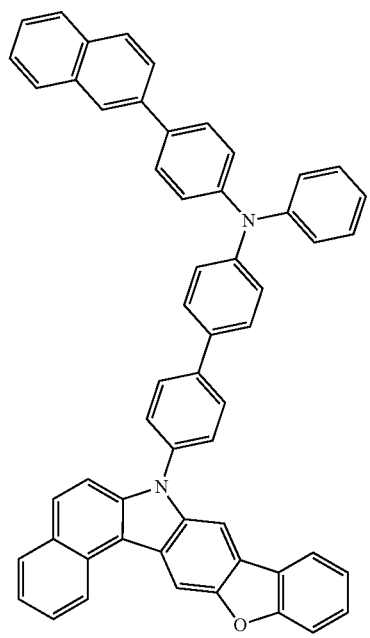
H1-80
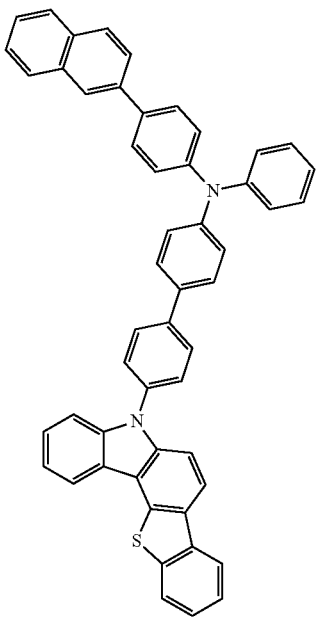
H1-79
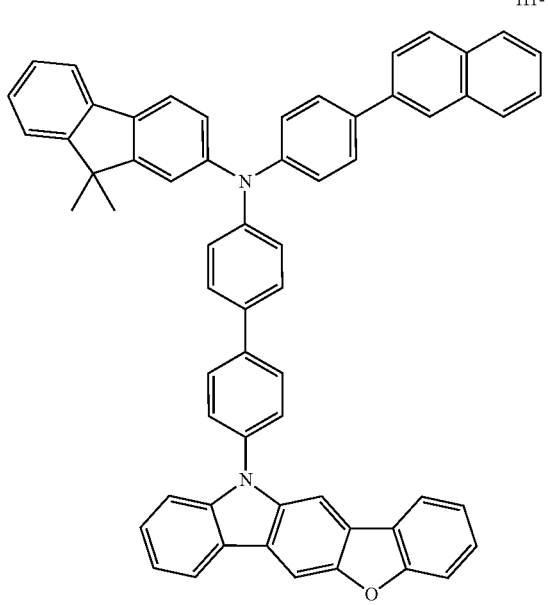
H1-81
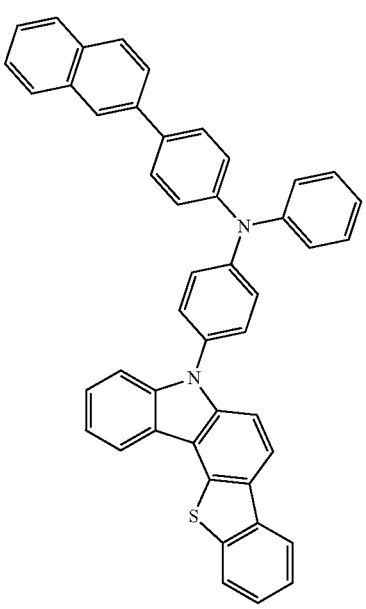

H1-82
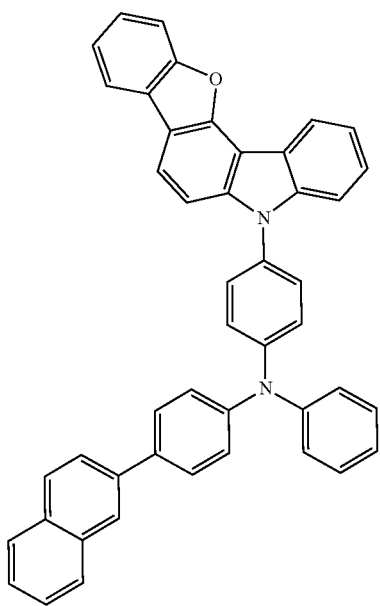
H1-84
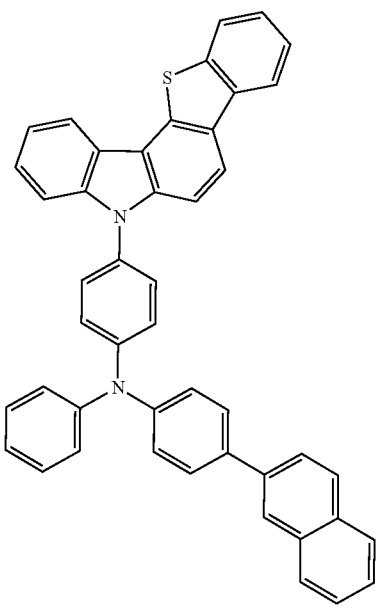
H1-85
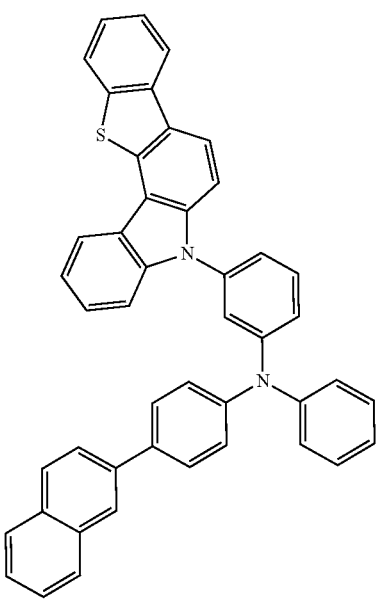
H1-83
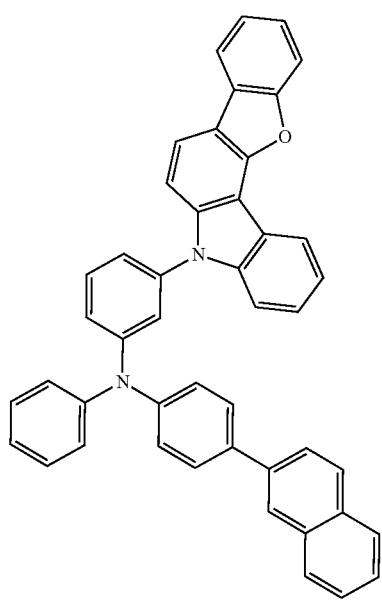
H1-86
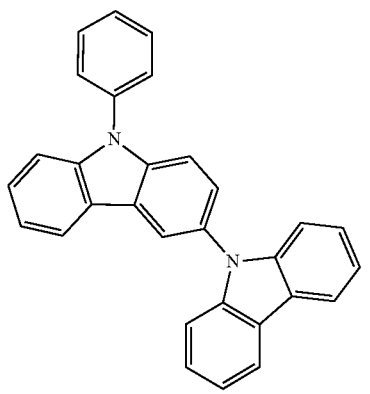

H1-87
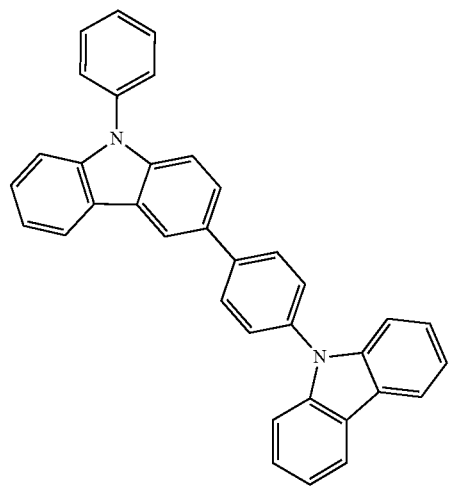
H1-88
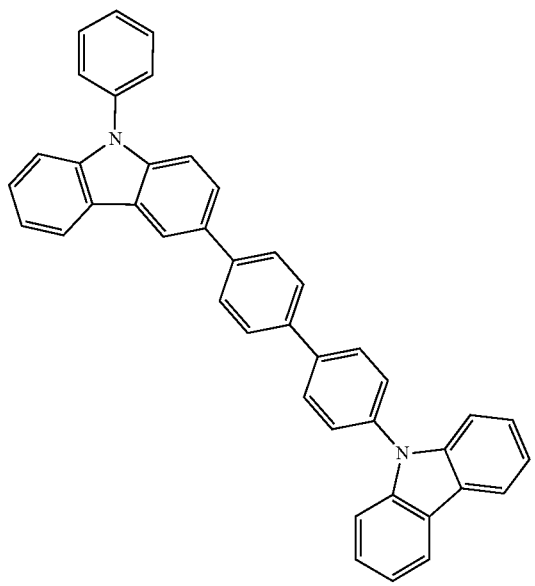
H1-89
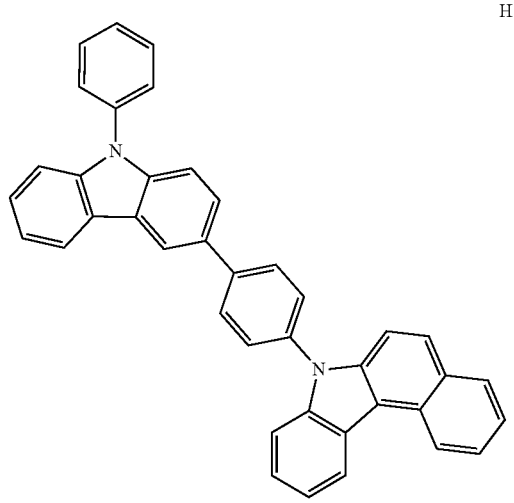
H1-90
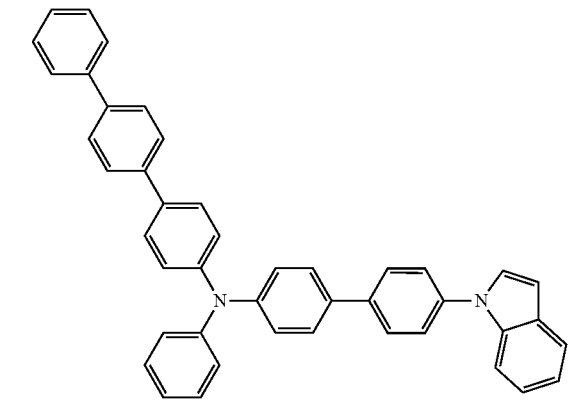
H1-91
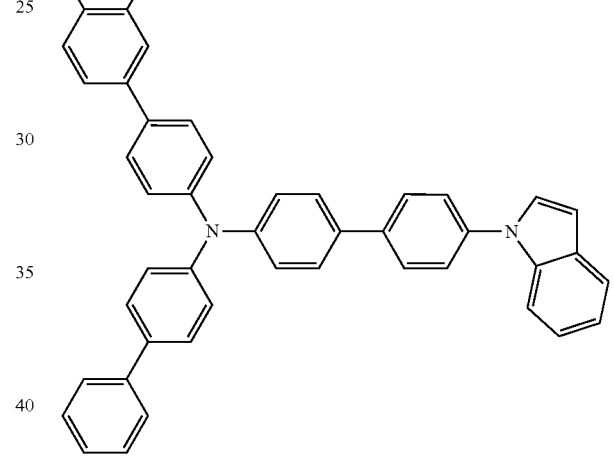
H1-92
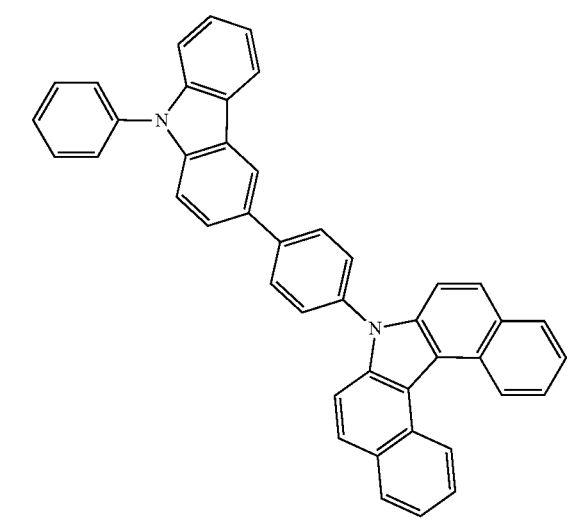

H1-93
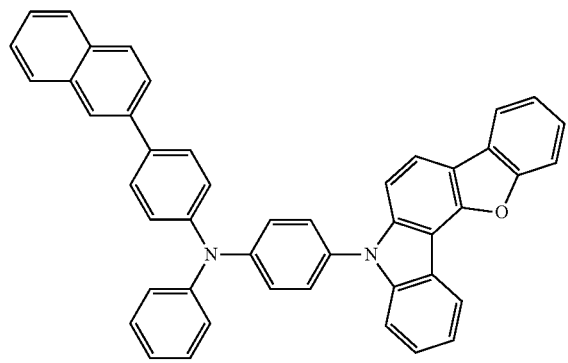
H2-2
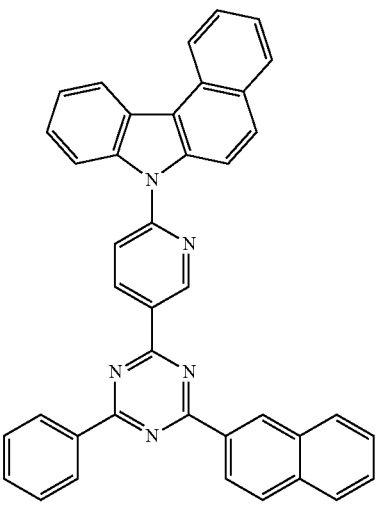
H1-94
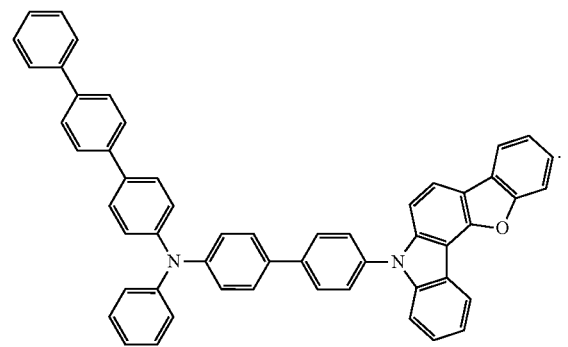
4. The host material according to claim 1, wherein the second host compound of formula 2 is selected from the group consisting of:
H2-3
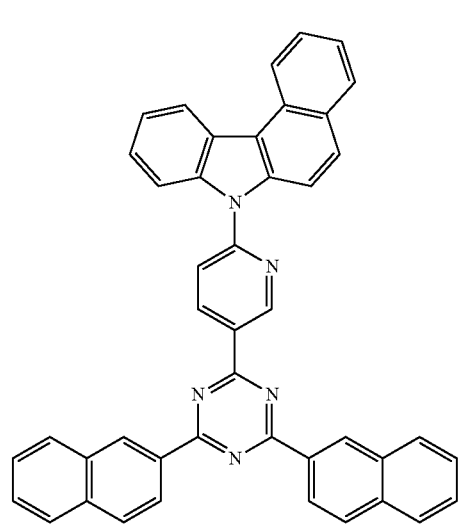
H2-1
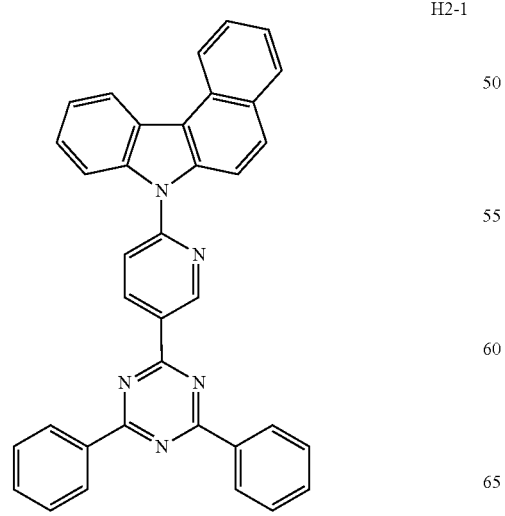
H2-4
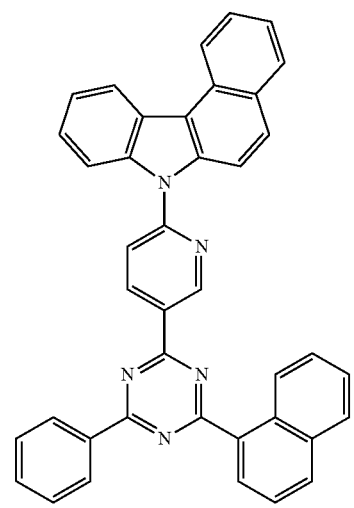

-continued
H2-5
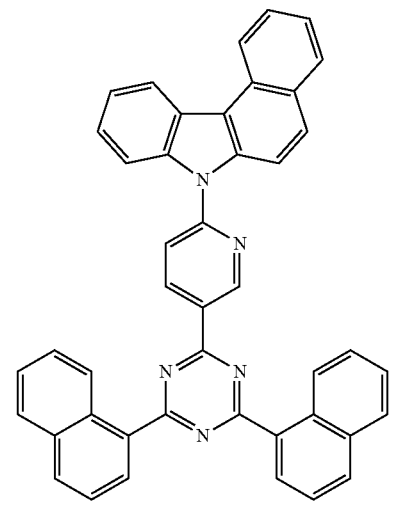
H2-6
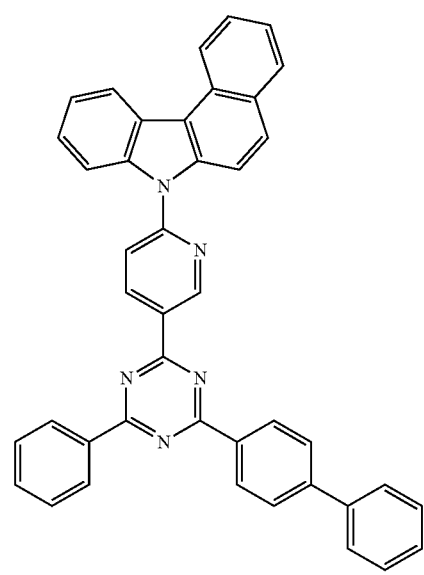
H2-7
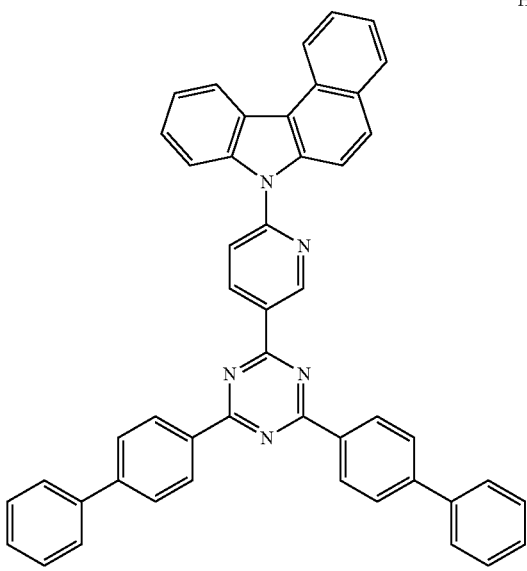
-continued
H2-8
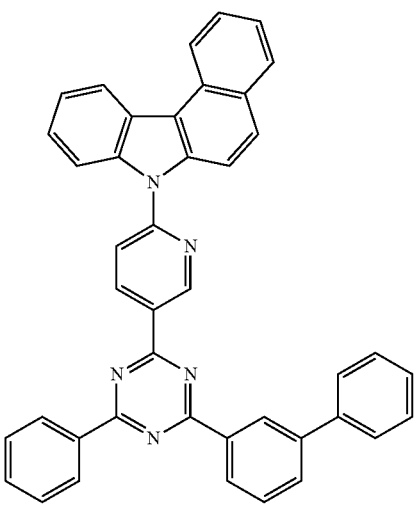
H2-9
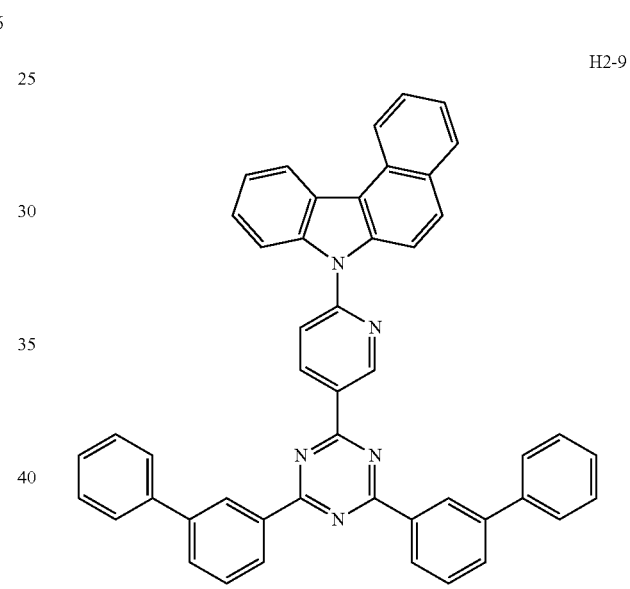
H2-10
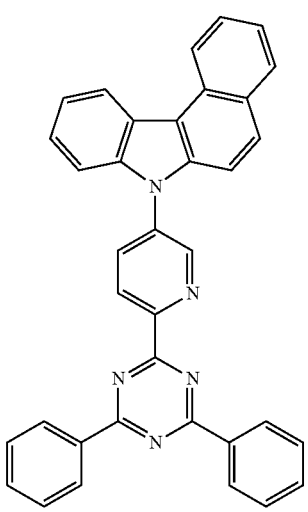

-continued
H2-11
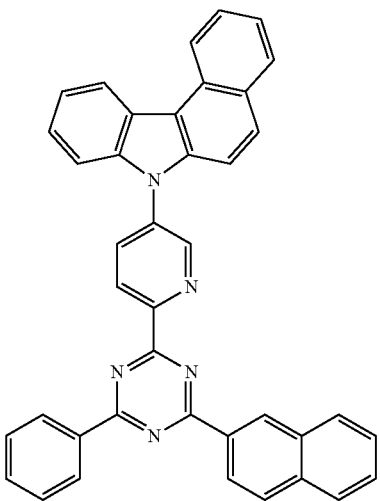
H2-12
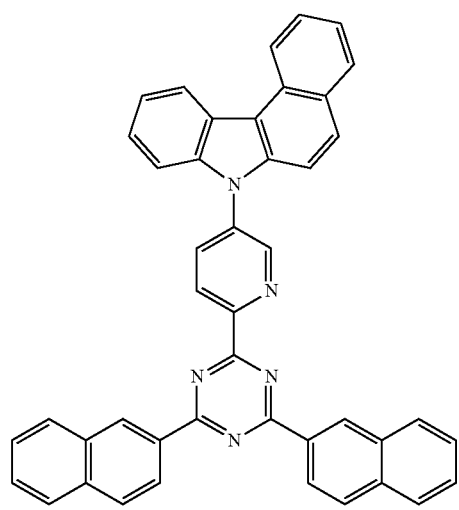
H2-13
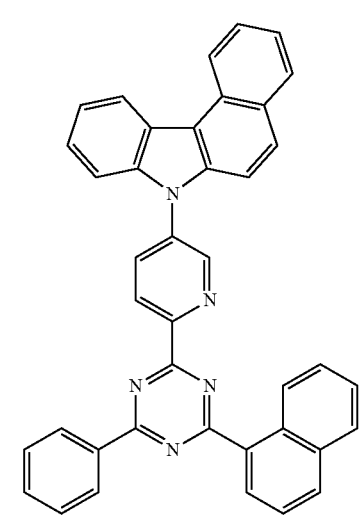
-continued
H2-14
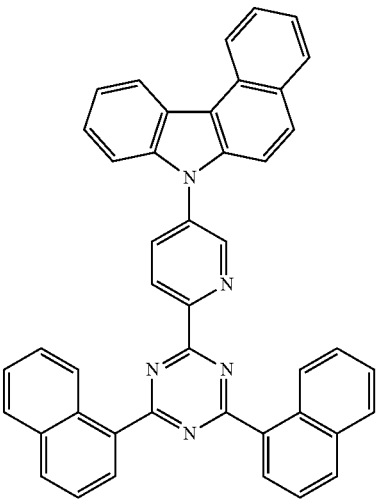
H2-15
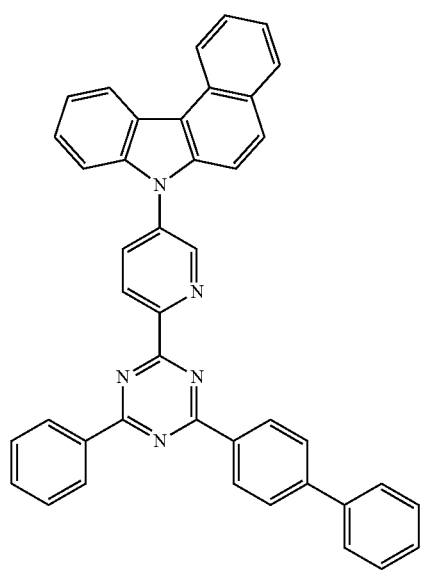
H2-16
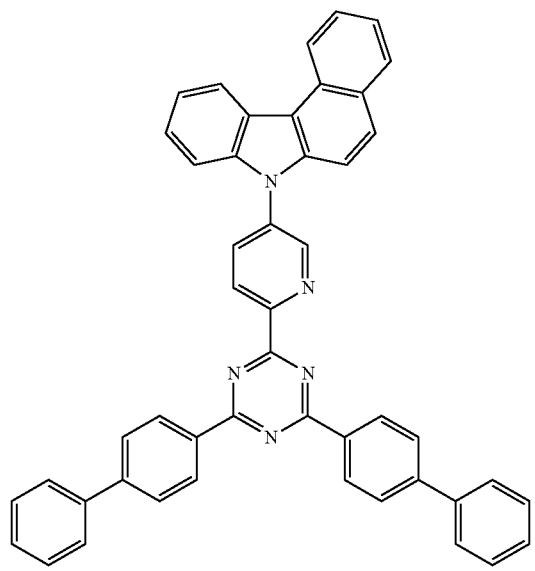

H2-17
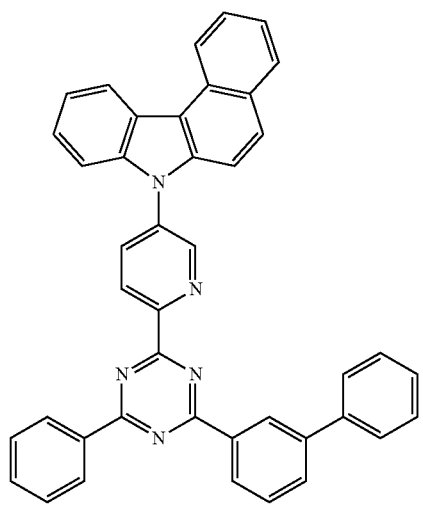
H2-18
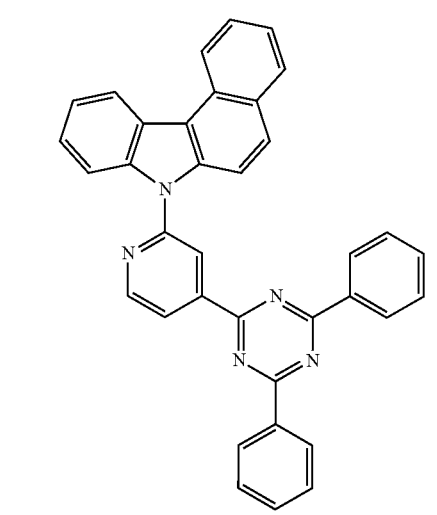
H2-19
H2-20
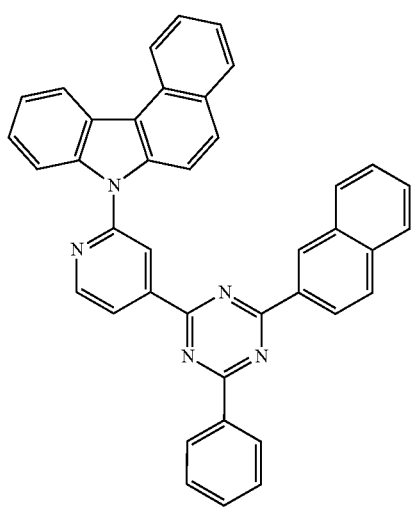
H2-21
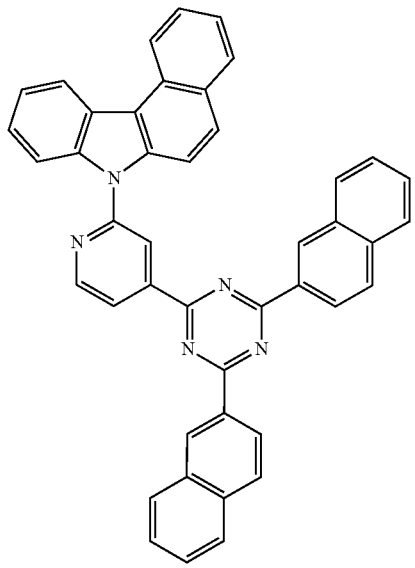
H2-22

H2-23
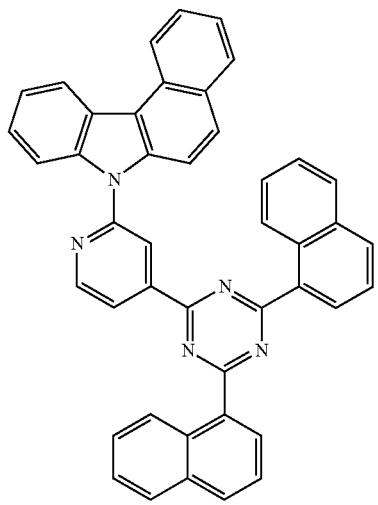
H2-24
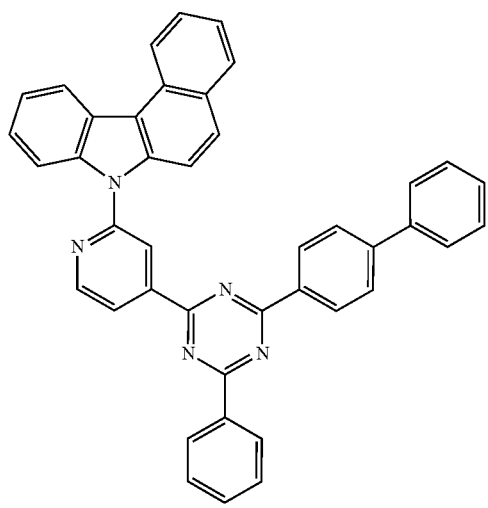
H2-25
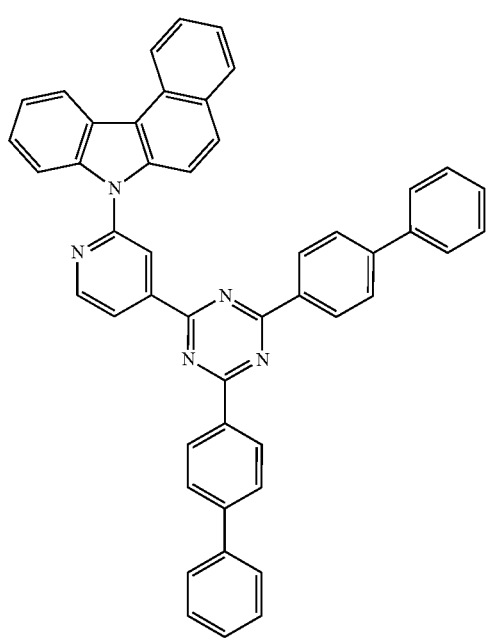
H2-26
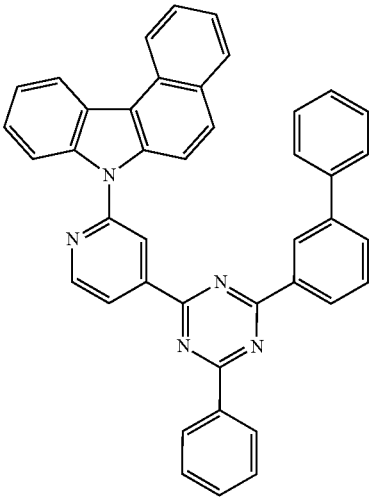
H2-27
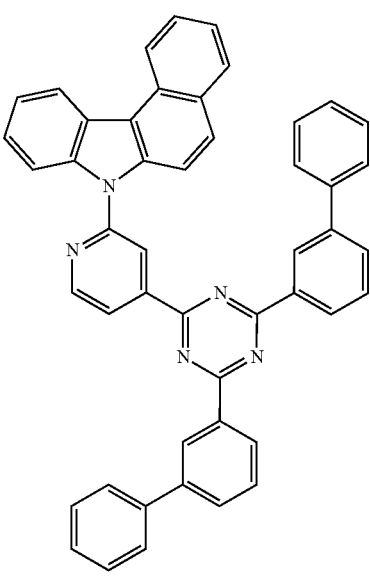
H2-28

H2-29
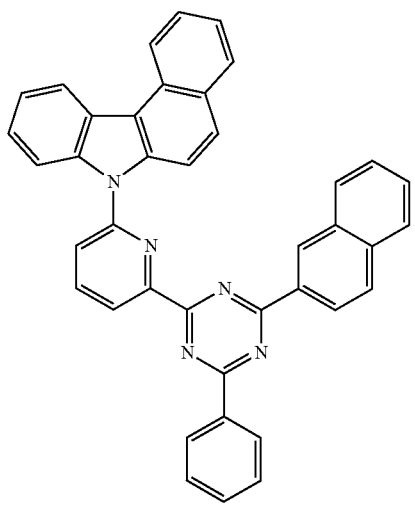
H2-30
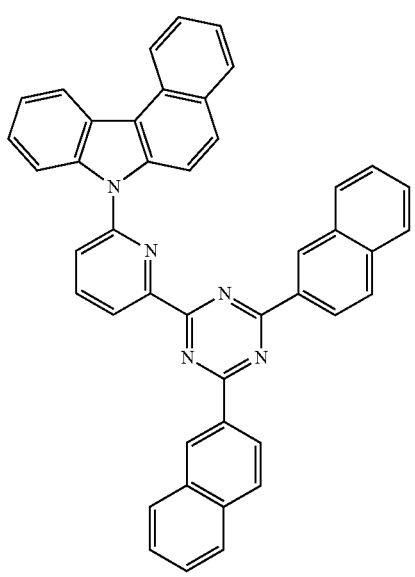
H2-31
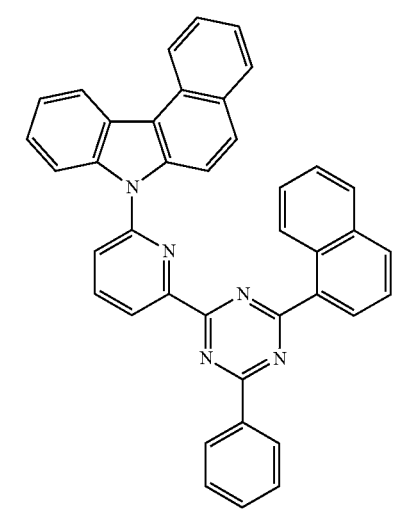
H2-32
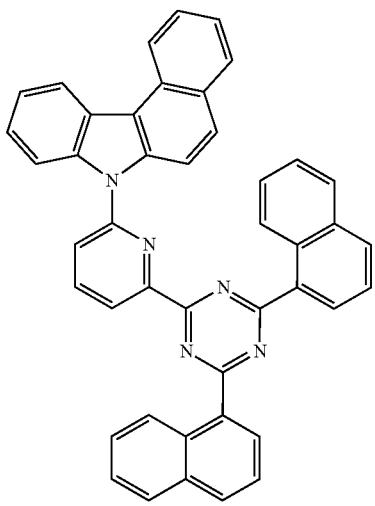
H2-33
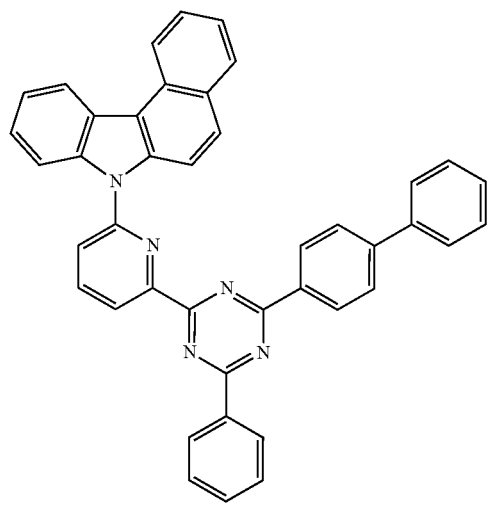
H2-34
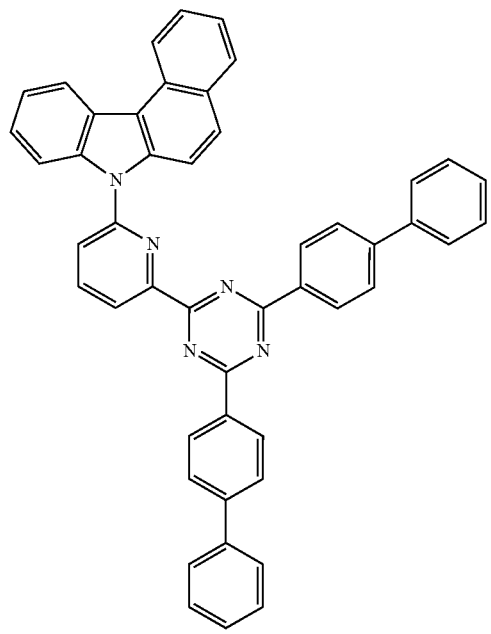

H2-35
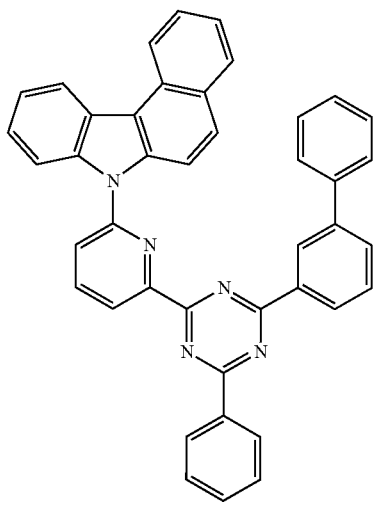
H2-36
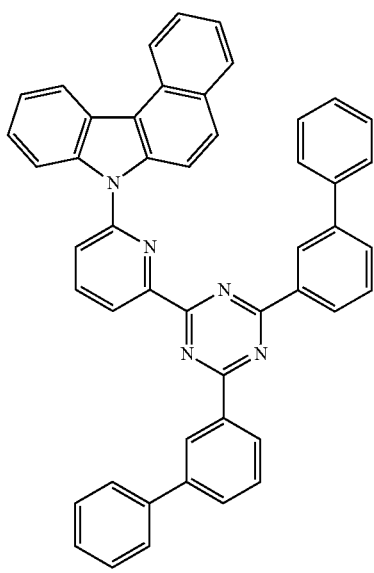
H2-37
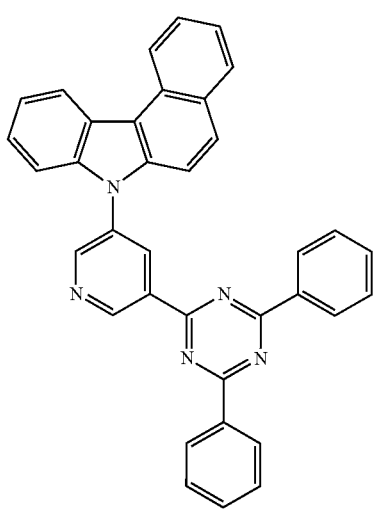
H2-38
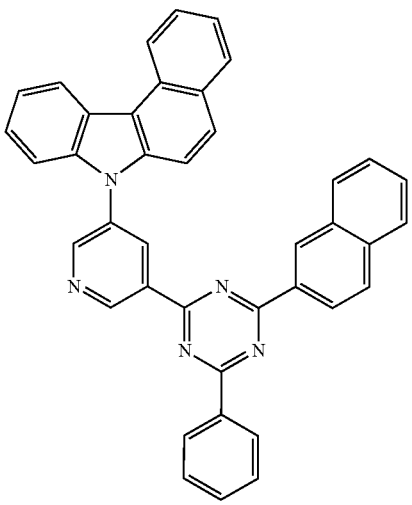
H2-39
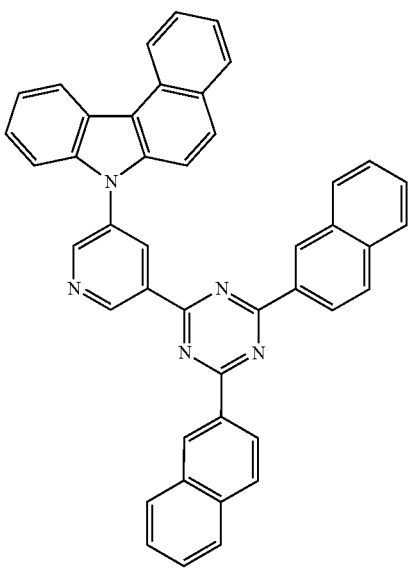
H2-40
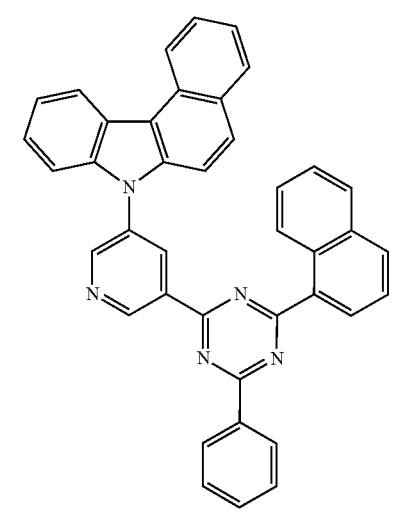

H2-41
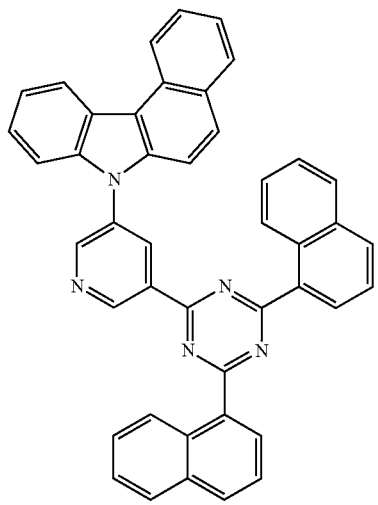
H2-42
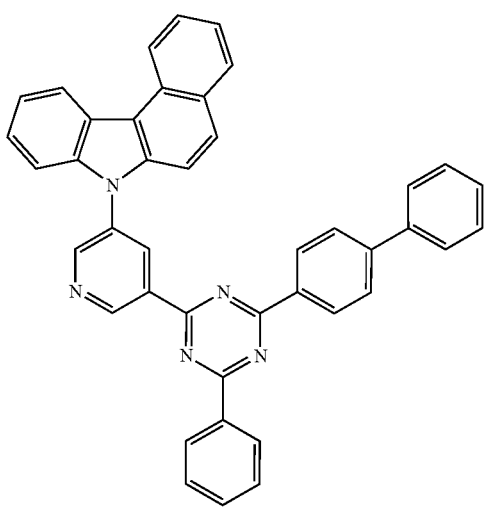
H2-43
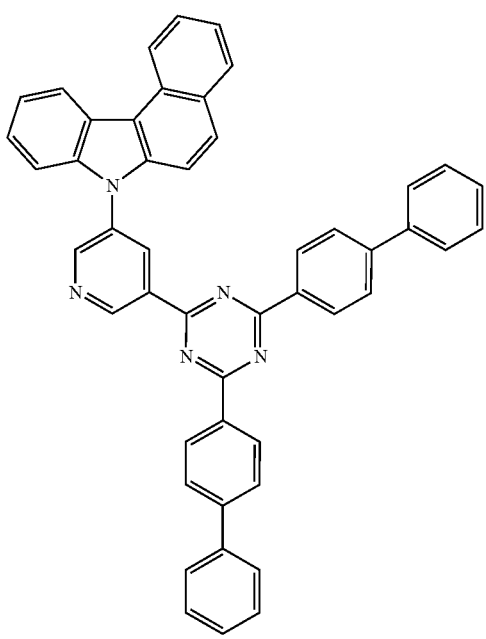
H2-44
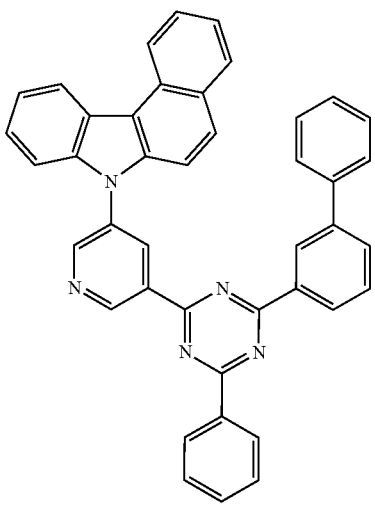
H2-45
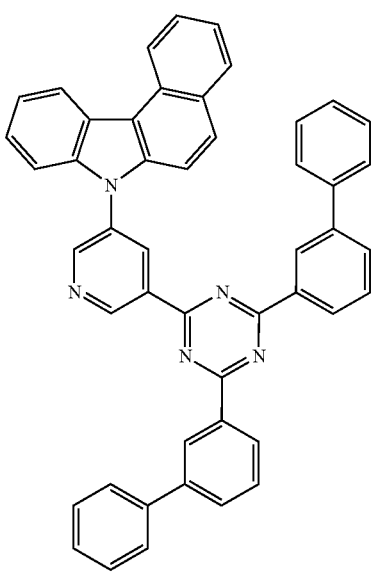
H2-46
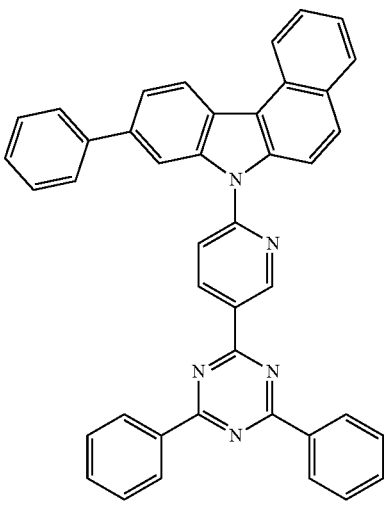

H2-47
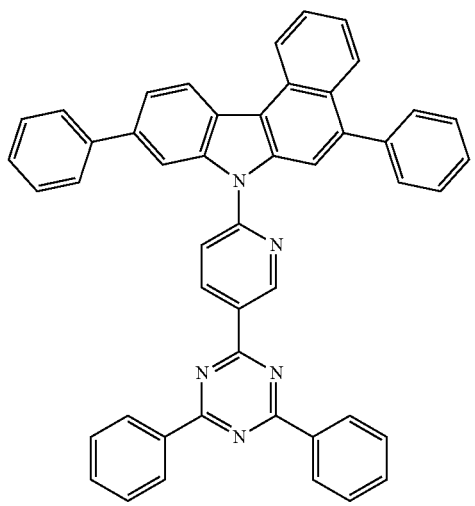
H2-50
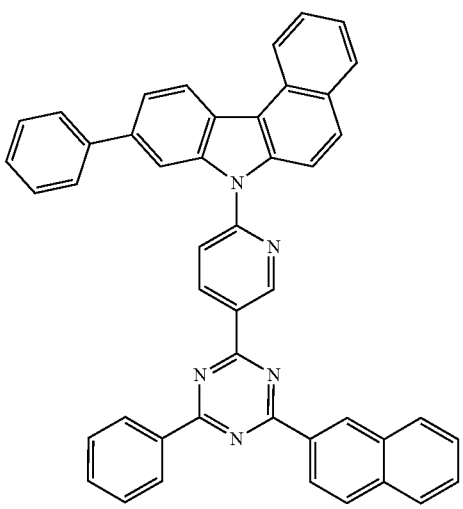
H2-48
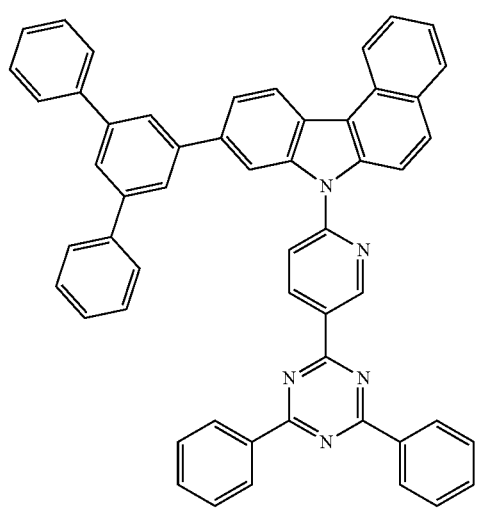
H2-51
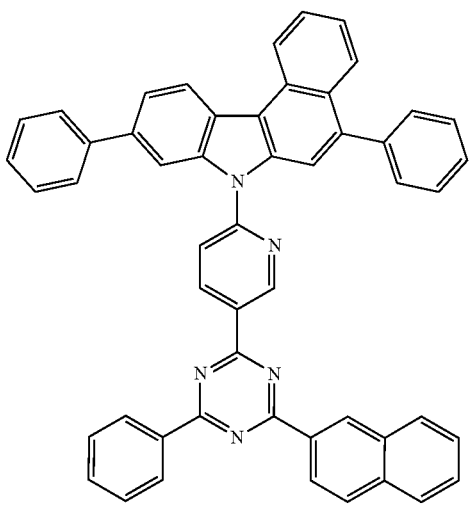
H2-49
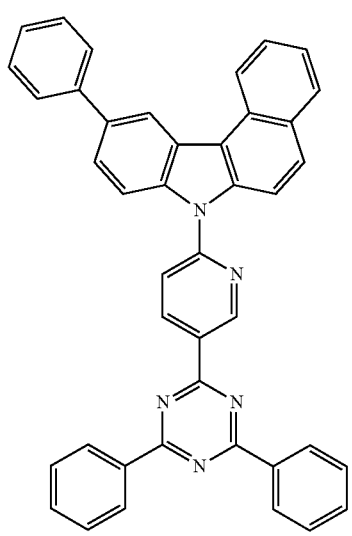
H2-52
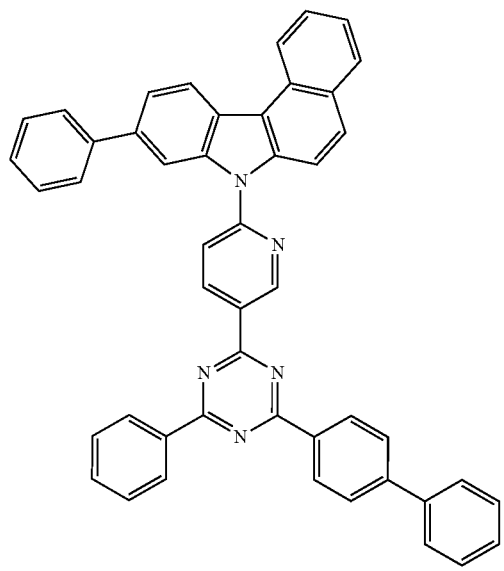

-continued
H2-53
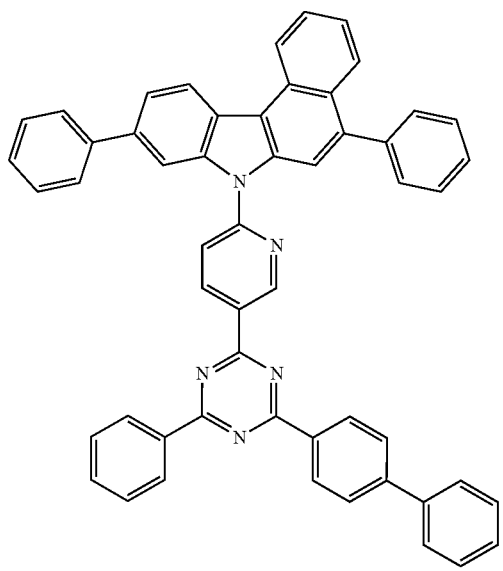
H2-54
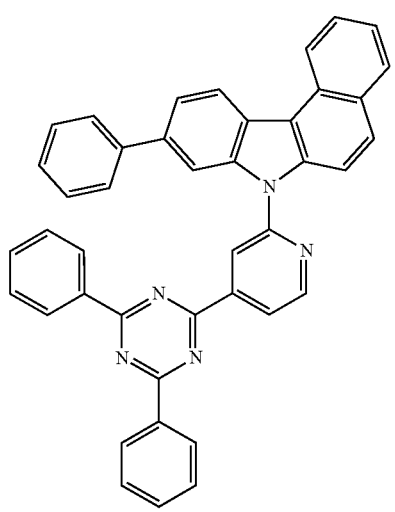
H2-55
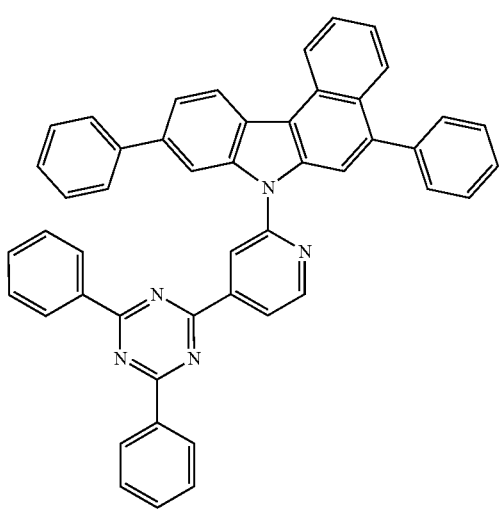
-continued
H2-56
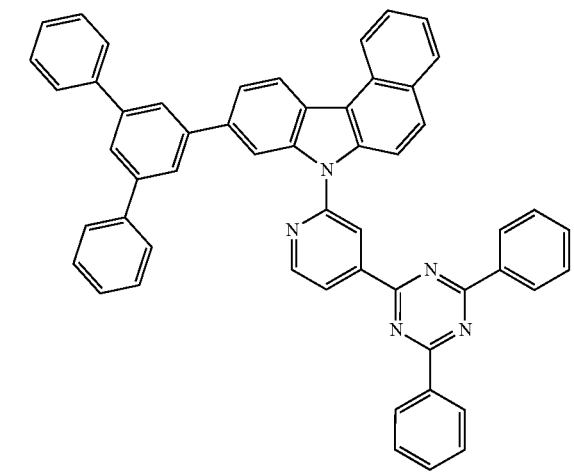
H2-57
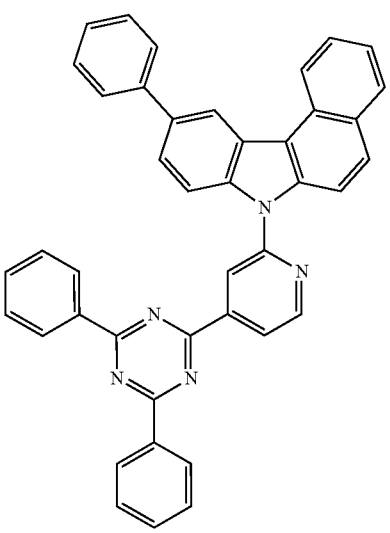
H2-58

-continued
H2-59
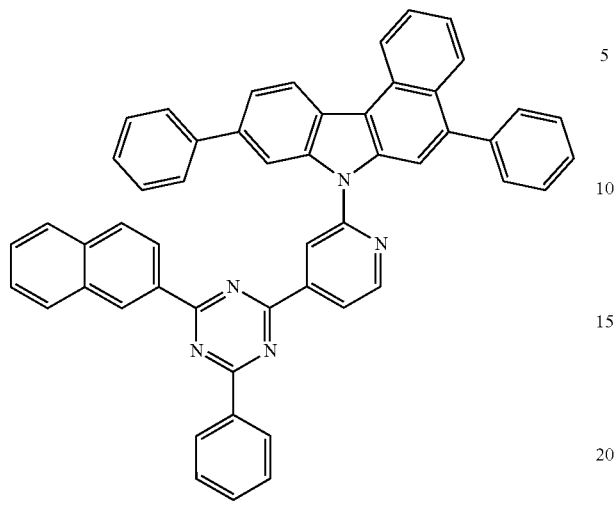
H2-60
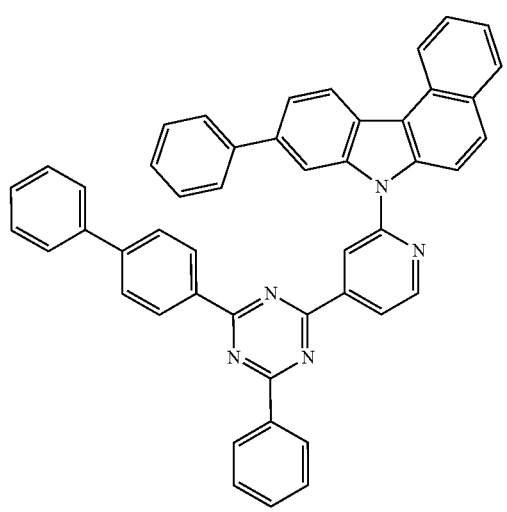
H2-61
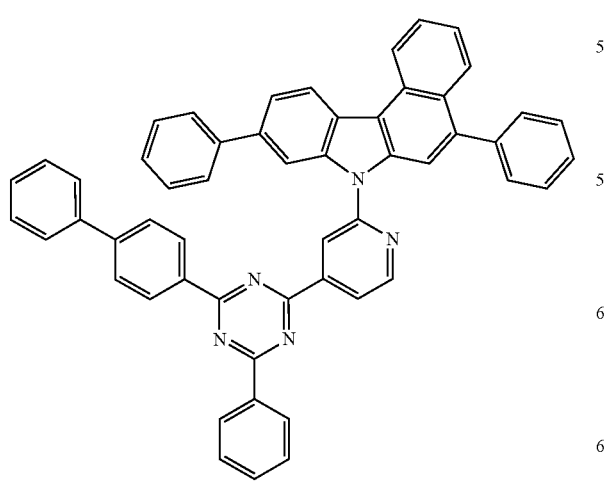
-continued
H2-62
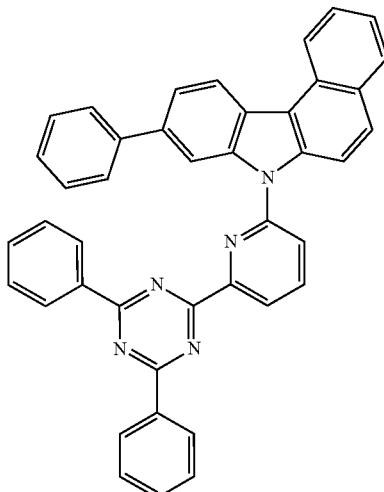
H2-63
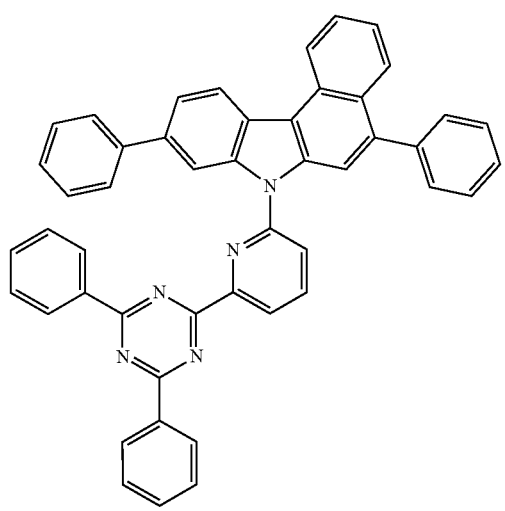
H2-64
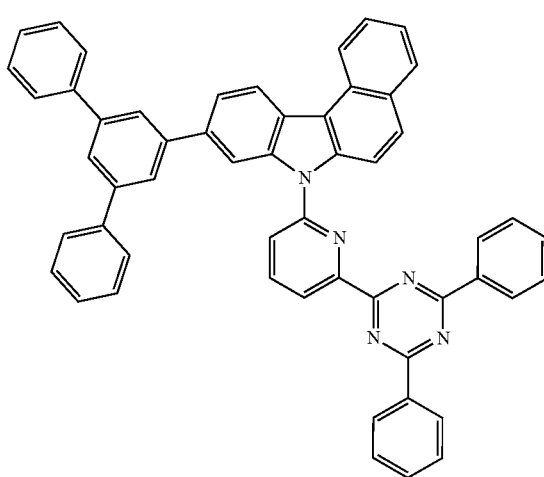

H2-65
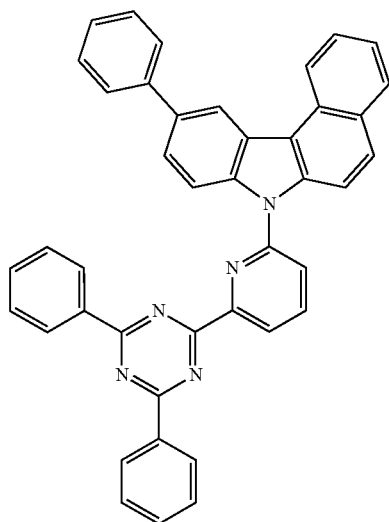
H2-66
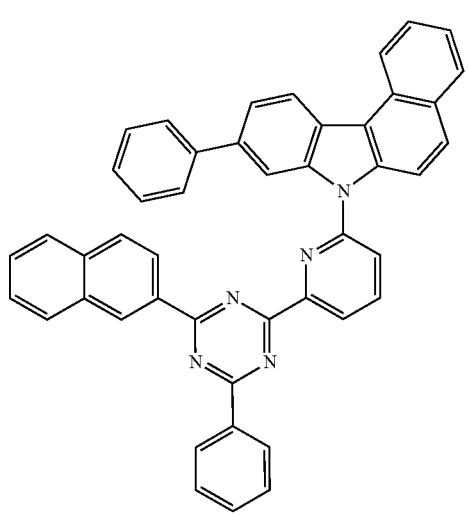
H2-67
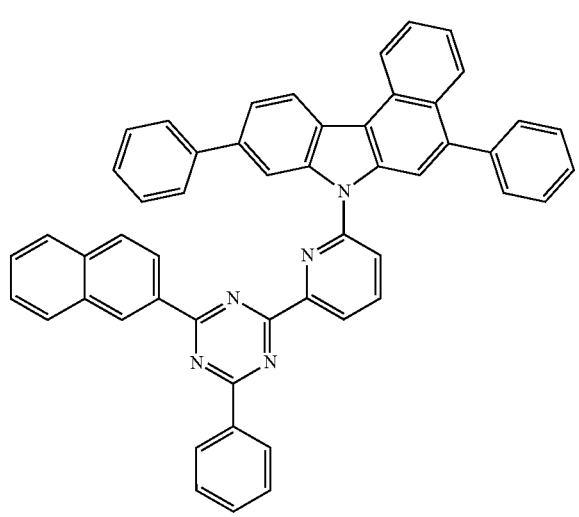
H2-68
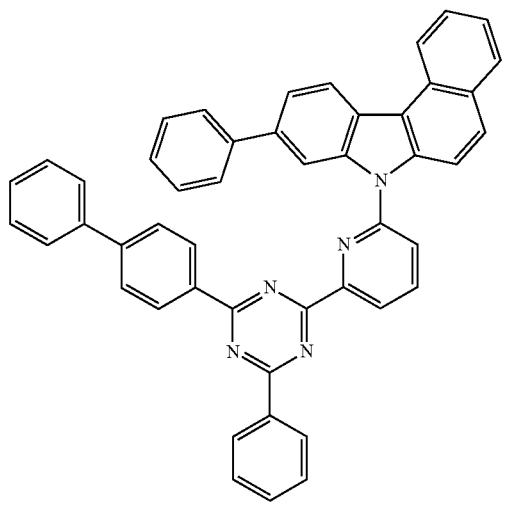
H2-69
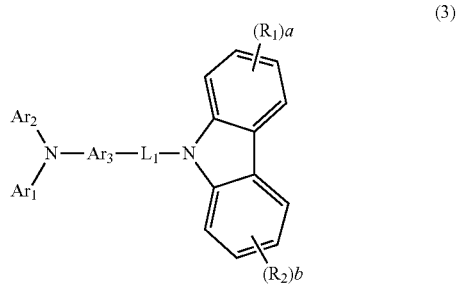
5. The host material according to claim 1, wherein formula 1 is represented by any one of the following formulae 3 to 7:
$$\text{(3)}$$

-continued (4)
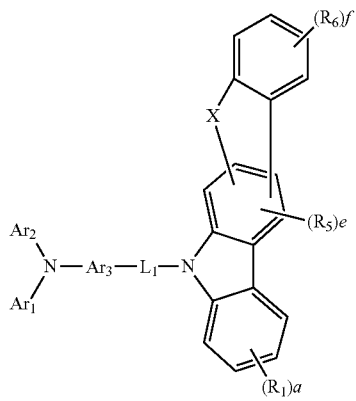

(5)
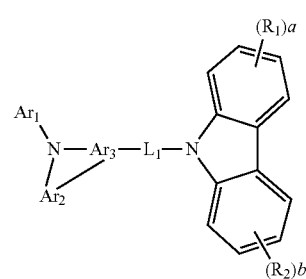

(6)
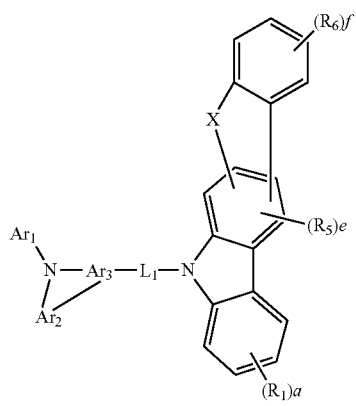

(7)
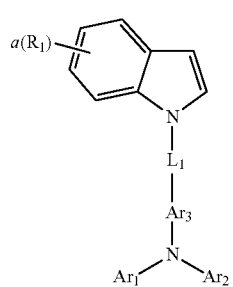

wherein

Ar₁, Ar₂, and Ar₃, each independently, represent a substituted or unsubstituted (C6-C30)aryl(ene), or a substituted or unsubstituted 3 to 30-membered heteroaryl(ene);

X represents S, O or $CR_7R_8$;

$R_2$ and $R_5$ to $R_8$, each independently, represent deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or $R_2$ and $R_5$ to $R_8$, each independently, are linked to an adjacent substituent(s) to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur;

b and f, each independently, represent an integer of 0 to 4, and e represents an integer of 0 to 2; when each of b or f represents an integer of 2 or more, or when e represents an integer of 2, each of $R_2$, $R_5$, or $R_6$ may be the same or different; and $L_1$, $R_1$, and a are as defined in claim 1.

6. The host material according to claim 5, wherein formula 3 is represented by any one of the following formulae 8 to 10:

(8)
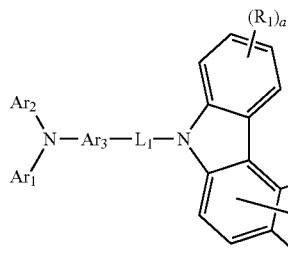

(9)
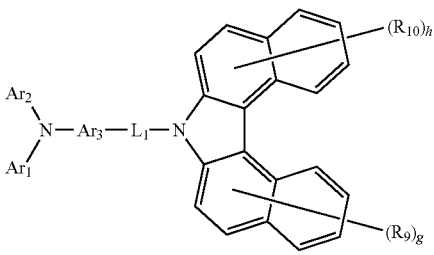

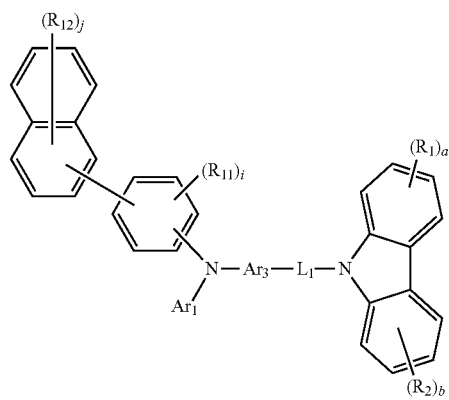 (10)

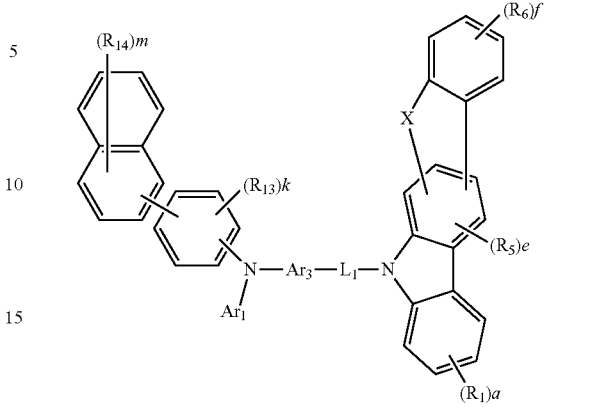 (11)

wherein $R_9$ to $R_{12}$, each independently, represent deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or $R_9$ to $R_{12}$, each independently, may be linked to an adjacent substituent(s) to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur;

the heteroaryl contains one or more heteroatoms selected from the group consisting of B, N, O, S, Si, and P;

g and h, each independently, represent an integer of 0 to 6; i represents an integer of 0 to 4; j represents an integer of 0 to 7; when each of g, h, i or j represents an integer of 2 or more, each of $R_9$, $R_{10}$, $R_{11}$ or $R_{12}$ may be the same or different; and $L_1$, $R_1$, $R_2$, $Ar_1$, $Ar_2$, $Ar_3$, a, and b are as defined in claim 5.

7. The host material according to claim 5, wherein formula 4 is represented by the following formula 11:

wherein $R_{13}$ and $R_{14}$, each independently, represent deuterium, a halogen, a cyano, a substituted or unsubstituted (C1-C30)alkyl, a substituted or unsubstituted (C2-C30) alkenyl, a substituted or unsubstituted (C2-C30)alkynyl, a substituted or unsubstituted (C3-C30)cycloalkyl, a substituted or unsubstituted (C6-C30)aryl, a substituted or unsubstituted 3- to 30-membered heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, or a substituted or unsubstituted mono- or di-(C6-C30)arylamino; or $R_{13}$ and $R_{14}$, each independently, may be linked to an adjacent substituent(s) to form a substituted or unsubstituted 3 to 30-membered, mono- or polycyclic, alicyclic or aromatic ring, or a combination of the alicyclic ring and the aromatic ring, whose carbon atom(s) may be replaced with at least one heteroatom selected from the group consisting of nitrogen, oxygen, and sulfur;

the heteroaryl contains one or more heteroatoms selected from the group consisting of B, N, O, S, Si, and P;

k represents an integer of 0 to 4, and m represents an integer of 0 to 7; when each of k or m represents an integer of 2 or more, each of $R_{13}$ or $R_{14}$ may be the same or different; and $L_1$, $R_1$, $R_5$, $R_6$, $Ar_1$, $Ar_3$, a, e, and f are as defined in claim 5.

8. An organic electroluminescent device comprising an anode, a cathode, and at least one light-emitting layer disposed between the anode and cathode, wherein the light-emitting layer comprises a host and a dopant, and the host comprises the host material according to claim 1.

* * * * *